US009457062B2

(12) United States Patent
Johnson et al.

(10) Patent No.: US 9,457,062 B2
(45) Date of Patent: *Oct. 4, 2016

(54) CHAPERONIN 10-INDUCED IMMUNOMODULATION

(75) Inventors: Barbara J. Johnson, Queensland (AU); Caroline A. Dobbin, Queensland (AU); Dean J. Naylor, Queensland (AU); Linda A. Ward, Queensland (AU); Inge E. A. Flesch, Queensland (AU); Christopher B. Howard, Queensland (AU)

(73) Assignee: CBIO LIMITED, Queensland (AU)

(*) Notice: Subject to any disclaimer, the term of this patent is extended or adjusted under 35 U.S.C. 154(b) by 1047 days.

This patent is subject to a terminal disclaimer.

(21) Appl. No.: 11/995,524

(22) PCT Filed: Jul. 11, 2006

(86) PCT No.: PCT/AU2006/000980
§ 371 (c)(1),
(2), (4) Date: Jul. 28, 2008

(87) PCT Pub. No.: WO2007/006095
PCT Pub. Date: Jan. 18, 2007

(65) Prior Publication Data
US 2009/0047240 A1    Feb. 19, 2009

(30) Foreign Application Priority Data

Jul. 11, 2005 (AU) ................................ 2005903675
Feb. 9, 2006 (AU) ................................ 2006900631

(51) Int. Cl.
*A61K 38/17* (2006.01)
*C07K 14/47* (2006.01)
*A61K 38/21* (2006.01)
*C07K 16/18* (2006.01)

(52) U.S. Cl.
CPC ......... *A61K 38/1709* (2013.01); *A61K 38/212* (2013.01); *A61K 38/215* (2013.01); *C07K 16/18* (2013.01)

(58) Field of Classification Search
None
See application file for complete search history.

(56) References Cited

U.S. PATENT DOCUMENTS 6,117,421 A * 9/2000 Morton et al. ............. 424/78.06
2006/0198834 A1* 9/2006 Hill et al. ................... 424/94.63

FOREIGN PATENT DOCUMENTS

WO   WO 2004/041300    * 5/2004
WO   WO-2004/041300 A1   5/2004
WO   WO-2005/067959 A1   7/2005

OTHER PUBLICATIONS

Vanags, Therapeutic efficacy and safety of chaperonin 10 in patients with rheumatoid arthritis: a double-blind randomised trial, 2006, Lancet, vol. 368, pp. 855-863.*
Schwandner et al. Peptidoglycan- and lipoteichoic acid-induced cell activation is mediated by toll-like receptor 2. J Biol Chem. Jun. 18, 1999;274(25):17406-9.*
Nilsen et al. Lipopolysaccharide and double-stranded RNA up-regulate toll-like receptor 2 independently of myeloid differentiation factor 88. J Biol Chem. Sep. 17, 2004;279(38):39727-35. Epub Jun. 9, 2004.*
Broadley, S. A. et al. (Nov. 8, 2005). "Phase Ia and Ib Clinical Trials of Chaperonin 10 in Healthy Volunteers and Patients with Multiple Sclerosis," Poster Abstract 0487, *Journal of the Neurological Sciences* 238(Supplement 1):S223.
Dobbin, C. et al. (2005). "Heat Shock Protein 10 Modulates Innate Immunity Through Interaction with Multiple Toll-like Receptor Family Members," Abstract 248, *Tissue Antigens* 66:433-434.
International Preliminary Report on Patentability completed Oct. 24, 2007, for PCT Application No. PCT/AU2006/000980 filed Jul. 11, 2006, 5 pages.
International Search Report mailed Dec. 22, 2006, for PCT Application No. PCT/AU2006/000980 filed Jul. 11, 2006, 3 pages.
Johnson, B. J. et al. (Feb. 11, 2005). "Heat Shock Protein 10 Inhibits Lipopolysaccharide-Induced Inflammatory Mediator Production," *The Journal of Biological Chemistry* 280(6):4037-4047.
Vanags, D. (Sep. 2, 2006). "Therapeutic Efficacy and Safety of Chaperonin 10 in Patients with Rheumatoid Arthritis: a Double-Blind Randomised Trial," *The Lancet* 368: 855-863.
European Search Report received for European Patent Application No. 06752688.9, mailed on Jul. 22, 2009, 8 pages.
Office Action received for New Zealand Patent Application No. 565731, mailed on Dec. 2, 2009, 2 pages.
Office Action received for New Zealand Patent Application No. 565731, mailed on Jun. 14, 2011, 3 pages.
Office Action received for Philippines Patent Application No. 1-2008-500318, mailed on Aug. 10, 2011, 2 pages.
Office Action received for Singapore Patent Application No. 200800214-9, mailed on Nov. 2, 2009, 10 pages.
Written Opinion received for Singapore Patent Application No. 200800214-9, mailed on Feb. 3, 2009, 11 pages.
Office Action received for Australian Patent Application No. 2006269824, mailed on Mar. 24, 2011, 3 pages.
Office Action received for Chinese Patent Application No. 200680031144.7, issued on Nov. 1, 2010, 9 pages (5 pages of English Translation and 4 pages of Office Action).
Office Action received for Chinese Patent Application No. 200680031144.7, 8 pages (4 pages of English Translation and 4 pages of Office Action).

* cited by examiner

*Primary Examiner* — David Romeo
(74) *Attorney, Agent, or Firm* — Ditthavong & Steiner, P.C.

(57) ABSTRACT

The present invention relates to methods for modulating Toll-like receptor signalling in a subject, or in at least one cell, tissue or organ thereof, methods for treating or preventing a disease or condition in a subject, methods for modulating the production and/or secretion of one or more immunomodulators in a subject, or at least one cell, tissue or organ thereof, wherein said methods involve the administration of chaperonin 10, and wherein the chaperonin 10 associates with a Toll-like receptor in an activation cluster. Also contemplated are associated compositions and uses thereof.

4 Claims, 41 Drawing Sheets

CHAPERONIN 10-INDUCED IMMUNOMODULATION

CROSS REFERENCE TO RELATED APPLICATIONS

This application is a U.S. National Phase patent application of PCT/AU2006/000980, filed Jul. 11, 2006, which claims priority to Australian Patent Application No. 2005903675 filed Jul. 11, 2005 and Australian Patent Application No. 2006900631, filed Feb. 9, 2006, the contents of which are hereby incorporated by reference in the present disclosure in their entirety.

FIELD OF THE INVENTION

The present invention relates generally to the use of chaperonin 10 in the modulation of Toll-like receptor signalling, in particular TLR2, TLR3, TLR4, TLR7 and TLR9 signalling, and to methods and compositions for the treatment of diseases, including but not limited to viral and bacterial infections, inflammatory diseases and autoimmune diseases, via chaperonin 10-induced modulation of such signalling.

BACKGROUND OF THE INVENTION

A central component of host defence systems against invading bacterial, fungal, yeast and viral pathogens involves the successful recognition of the pathogen, or components thereof, by cellular receptors which induce a signalling cascade resulting in stimulation of the immune system and the production of various cytokines. One family of receptors which plays a key role in this line of defence is the Toll-like receptor (TLR) family. TLRs are expressed on immune cells including monocytes, macrophages, dendritic cells, B cells and granulocytes, and a variety of other cell types including endothelium and epithelium. TLR activation by pathogens, or by molecules derived therefrom, induces intracellular signalling that primarily results in activation of the transcription factor NF-κB (Beg, 2002, *Trends Immunol* 23:509-12.) and modulation of cytokine production. However, a series of other pathways can also be triggered, including p38 mitogen activated kinase, c-Jun-N-terminal kinase and extracellular signal related kinase pathways (Flohe et al., 2003, *J Immunol* 170:2340-2348; Triantafilou and Triantafilou, 2002, *Trends Immunol* 23:301-304).

Type I interferons, principally IFNα and IFNβ, are major contributors in the immune response to bacterial and viral infections. The primary source of type I interferons following such infections are plasmacytoid dendritic cells (PDCs), a specialised subpopulation of peripheral blood mononuclear cells. PDCs express the Toll-like receptors TLR7 and TLR9 and it is TLR7/TLR9 stimulation that is responsible for PDC activation and the production of large quantities of type I interferons.

A range of pathogen-derived factors are capable of selectively stimulating different TLRs. One of the best characterised of these is lipopolysaccharide (LPS), a glycolipid derived from the outer membrane of Gram-negative bacteria, which is an agonist of TLR4. TLR2 recognizes lipoteichoic acid (LTA), petidoglycan (PGN) and lipopeptide, TLR3 recognises double-stranded RNA, typically of viral origin; TLR 7 recognises viral single-stranded RNA and TLR9 recognises unmethylated CpG dinucleotides, typically within bacterial and viral DNA. TLRs can also be stimulated by a variety of synthetic agonists, for example polyI:C (polyinosinic-polysytidilic acid) in the case of TLR3, imidazoquinolines such as resiquimod (R848) and imiquimod in the case of TLR7 and CpG-rich oligonucleotides in the case of TLR9.

The elucidation of mechanisms for the modulation of TLR signalling and modulation of TLR-stimulated cytokine and chemokine production will provide avenues for the development of therapeutic approaches to the treatment of a variety of diseases and conditions, including viral and bacterial diseases.

Mammalian chaperonin 10 (Cpn10), also known as heat shock protein 10 (Hsp 10), is typically characterised as a mitochondrial 'molecular chaperone' protein involved in protein folding together with chaperonin 60 (Cpn60; Hsp60). Cpn10 is a homologue of the bacterial protein GroES. GroES and Cpn10 oligomerise into seven member rings that bind as a lid onto a barrel-like structure that comprises fourteen GroEL or seven Hsp60 molecules, which tether denatured proteins to the complex. Cpn10 is also frequently found at the cell surface (Belles et al, 1999, *Infect Immun* 67:4191-4200) and in the extracellular fluid (Shin et al, 2003, *J Biol Chem* 278: 7607-7616).

However Cpn10 has also been shown to possess immunosuppressive activity in experimental autoimmune encephalomyelitis, delayed type hypersensitivity and allograft rejection models (Zhang et al., 2003, *J Neurol Sci* 212:37-46; Morton et al., 2000, *Immunol Cell Biol* 78:603-607).

Previously, the present inventors have also demonstrated that in the presence of TLR4 and TLR2 agonists (LPS and PAM$_3$CysSK$_4$, respectively), Cpn10 reduces TLR4- and TLR2-stimulated NF-κB activation, reduces TNF-α and RANTES secretion, whilst increasing IL-10 secretion in a dose-dependent manner (Johnson et al., 2005, *J Biol Chem* 280:4037-4047; International Patent Application No. PCT/AU2005/000041; WO2005/067959, the disclosures of which are incorporated herein by reference).

The inventors have now surprisingly found that Cpn10 also modulates signalling by TLR3, TLR7 and TLR9. Cpn10 is shown herein to dose-responsively enhance the production of IFNα and IFNβ in the presence of a TLR3-specific ligand, and to reduce NF-kB activation in the presence of TLR7- and TLR9-specific ligands. Moreover, the inventors have surprisingly shown that Cpn10, but not Cpn60 or GroES, associates with TLRs in activation clusters at the cell surface, with such activation clusters modulating TLR signalling.

SUMMARY OF THE INVENTION

According to a first aspect of the present invention, there is provided a method for modulating Toll-like receptor signalling in a subject, or in at least one cell, tissue or organ thereof, wherein said method comprises administering an effective amount of chaperonin 10, wherein Toll-like receptor signalling involves association of the chaperonin 10 with a Toll-like receptor in an activation cluster.

According to a second aspect of the present invention, there is provided a method for modulating Toll-like receptor signalling in a subject, or in at least one cell, tissue or organ thereof, wherein said method comprises administering an effective amount of at least one antagonist of chaperonin 10, wherein Toll-like receptor signalling involves association of the chaperonin 10 with a Toll-like receptor in an activation cluster, and wherein the antagonist prevents chaperonin 10 associating with a Toll-like receptor in an activation cluster, and/or prevents signalling by the activation cluster.

The activation cluster may be located on the surface of a cell.

The activation cluster may comprise chaperonin 10, a Toll-like receptor, and optionally, at least one other molecule. The at least one other molecule may comprise a Toll-like receptor agonist.

In one embodiment, the activation cluster comprises chaperonin 10, TLR2 and lipoteichoic acid (LTA).

In an additional embodiment, the activation cluster comprises chaperonin 10, TLR3 and double-stranded RNA.

In another embodiment, the activation cluster comprises chaperonin 10, TLR4 and LPS.

In a further embodiment, the activation cluster comprises chaperonin 10, TLR7 and single-stranded RNA.

In a still further embodiment, the activation cluster comprises chaperonin 10, TLR9 and DNA comprising a CpG motif.

The chaperonin 10 may be a naturally-derived, recombinantly produced or synthetically produced chaperonin 10. The chaperonin 10 may be of eukaryotic origin. The chaperonin 10 may be human chaperonin 10.

The chaperonin 10 may comprise the polypeptide sequence as set forth in SEQ ID NO:1, SEQ ID NO:2 or SEQ ID NO:3. The chaperonin 10 may be acetylated or non-acetylated.

The chaperonin 10 may be administered in the form of a polynucleotide encoding chaperonin 10. The polynucleotide encoding chaperonin 10 may be located in a genetic construct, operably linked to a promoter. The polynucleotide may comprise the sequence as set forth in SEQ ID NO:4.

The method may further comprise the administration of at least one additional agent. The agent may be an immunomodulator. The immunomodulator may be a type I interferon such as IFNα or IFNβ.

According to a third aspect of the present invention there is provided a method for treating or preventing a disease or condition in a subject, wherein said method comprises administering to the subject an effective amount of chaperonin 10, wherein the chaperonin 10 associates with a Toll-like receptor in an activation cluster, and wherein formation of the activation cluster is associated with initiation, enhancement and/or maintenance of an immune response to the disease or condition.

According to a fourth aspect of the present invention there is provided a method for the treatment or prevention of a disorder in the subject, wherein said method comprises administering to the subject an effective amount of at least one antagonist of chaperonin 10, wherein the antagonist prevents chaperonin 10 associating with a Toll-like receptor in an activation cluster, and/or prevents signalling by the activation cluster, and wherein formation of the activation cluster is associated with establishment and/or progression of the disease or condition.

The disease or condition may be selected from the group comprising viral, fungal, yeast or bacterial infections, acute or chronic inflammatory diseases including septic shock, inflammatory bowel disease, arthritis, psoriasis, heart disease, atherosclerosis, chronic pulmonary disease, cachexia, multiple sclerosis, GVHD and cancer.

In one embodiment, the chaperonin 10 regulates LTA-induced TLR2 signalling. The chaperonin 10 may modulate TLR2-induced immunomodulator production and/or secretion.

In an additional embodiment, the chaperonin 10 regulates double-stranded RNA-induced TLR3 signalling. The chaperonin 10 may modulate TLR3-induced immunomodulator production and/or secretion.

In another embodiment, the chaperonin 10 regulates LPS-induced TLR4 signalling. The chaperonin 10 may modulate TLR4-induced immunomodulator production and/or secretion.

In a further embodiment, the chaperonin 10 regulates viral single-stranded RNA-induced TLR7 signalling. The chaperonin 10 may modulate TLR7-induced immunomodulator production and/or secretion.

In a still further embodiment, the chaperonin 10 regulates CpG motif-induced TLR9 signalling. The chaperonin 10 may modulate TLR9-induced immunomodulator production and/or secretion.

The chaperonin 10 may be a naturally-derived, recombinantly produced or synthetically produced chaperonin 10. The chaperonin 10 may be of eukaryotic origin. The chaperonin 10 may be human chaperonin 10.

The chaperonin 10 may comprise the polypeptide sequence as set forth in SEQ ID NO:1, SEQ ID NO:2 or SEQ ID NO:3. The chaperonin 10 may be acetylated or non-acetylated.

The chaperonin 10 may be administered in the form of a polynucleotide encoding chaperonin 10. The polynucleotide encoding chaperonin 10 may be located in a genetic construct, operably linked to a promoter. The polynucleotide may comprise the sequence as set forth in SEQ ID NO:4.

The method may further comprise the administration of at least one additional agent. The agent may be an immunomodulator. The immunomodulator may be a type I interferon such as IFNα or IFNβ.

According to a fifth aspect of the present invention there is provided a composition when used for the treatment or prevention of a disease or condition, the composition comprising chaperonin 10 together with at least one pharmaceutically acceptable carrier, diluent or adjuvant, wherein the chaperonin 10 associates with a Toll-like receptor in an activation cluster, and wherein formation of the activation cluster is associated with initiation, enhancement and/or maintenance of an immune response to the disease or condition.

The composition may further comprise at least one agonist of a Toll-like receptor. The composition may further comprise at least one immunomodulator such as a type I interferon.

According to a sixth aspect of the present invention there is provided a composition when used for the treatment or prevention of a disease or condition, the composition comprising at least one antagonist of chaperonin 10, wherein the antagonist prevents chaperonin 10 associating with a Toll-like receptor in an activation cluster, and/or prevents signalling by the activation cluster, and wherein formation of the activation cluster is associated with establishment and/or progression of the disease or condition.

According to a seventh aspect of the present invention there is provided the use of chaperonin 10 for the manufacture of a medicament for the treatment or prevention of a disease or condition, wherein the chaperonin 10 associates with a Toll-like receptor in an activation cluster, and wherein formation of the activation cluster is associated with initiation, enhancement and/or maintenance of an immune response to the disease or condition.

According to an eighth aspect of the present invention there is provided the use of an antagonist of chaperonin 10 for the manufacture of a medicament for the treatment or prevention of a disease or condition, wherein the antagonist prevents chaperonin 10 associating with a Toll-like receptor in an activation cluster, and/or prevents signalling by the activation cluster, and wherein formation of the activation cluster is associated with establishment and/or progression of the disease or condition.

According to a ninth aspect of the present invention there is provided a method for modulating the production and/or secretion of one or more immunomodulators in a subject, or at least one cell, tissue or organ thereof, wherein said method comprises administering an effective amount of chaperonin 10, wherein the chaperonin 10 associates with a Toll-like receptor in an activation cluster, and wherein formation of the activation cluster is associated with modulation of the production and/or secretion of the one or more immunomodulators.

According to a tenth aspect of the present invention there is provided a method for modulating the production and/or secretion of one or more immunomodulators in a subject, or at least one cell, tissue or organ thereof, wherein said method comprises administering an effective amount of an antagonist of chaperonin 10, wherein the antagonist prevents chaperonin 10 associating with a Toll-like receptor in an activation cluster, and/or prevents signalling by the activation cluster, and wherein formation of the activation cluster is associated with modulation of the production and/or secretion of the one or more immunomodulators.

The immunomodulator may be, for example, TNF-α, IL-1β, IL-6, IL-10, IL-12 or a type I interferon. The type I interferon may be IFNα or IFNβ.

The above aspects and embodiments contemplate the use of wild-type and modified forms of chaperonin 10, as well as full-length chaperonin 10 polypeptides and fragments or derivatives thereof retaining immunomodulatory activity.

DEFINITIONS

In the context of this specification, the term "comprising" means "including principally, but not necessarily solely". Furthermore, variations of the word "comprising", such as "comprise" and "comprises", have correspondingly varied meanings.

As used herein the terms "treatment", "treating" and variations thereof, refer to any and all uses which remedy a disease state or symptoms, prevent the establishment of disease, or otherwise prevent, hinder, retard, ameliorate or reverse the progression of disease or other undesirable symptoms in any way whatsoever.

As used herein the term "effective amount" includes within its meaning a non-toxic but sufficient amount of an agent or compound to provide the desired therapeutic or prophylactic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

The term "polypeptide" means a polymer made up of amino acids linked together by peptide bonds. The terms "polypeptide" and "protein" are used interchangeably herein, although for the purposes of the present invention a "polypeptide" may constitute a portion of a full length protein. Polypeptides may also include, but are not limited to, fragments, analogues, variants and derivatives thereof. Such fragments, analogues, variants and derivatives thereof may share a particular structural and/or functional similarity with the polypeptide.

The term "polynucleotide" as used herein refers to a single- or double-stranded polymer of deoxyribonucleotide, ribonucleotide bases or known analogues or natural nucleotides, or mixtures thereof. Within the scope of the term "polynucleotide" is included the reverse complement of the polynucleotide, and fragments, analogues, variants and derivatives of the polynucleotide, as well as any other polynucleotide that hybridizes to the polynucleotide under conditions of high stringency.

As used herein the terms "modulating", "modulates" and variations thereof refer to increasing or decreasing the level of activity, production, secretion or functioning of a molecule in the presence of a particular modulatory molecule or agent of the invention compared to the level of activity, production, secretion or other functioning thereof in the absence of the modulatory molecule or agent. These terms do not imply quantification of the increase or decrease. The modulation may be of any magnitude sufficient to produce the desired result and may be direct or indirect.

The term "immunomodulator" as used herein includes, but is not limited to, a molecular mediator secreted by one or more cell types and which plays a role in the initiation, activation, maintenance, enhancement, maturation, inhibition, suppression or augmentation of an immune response.

The term "activation cluster" as used herein refers to an association of molecules that function to produce a biological signal. Typically, the biological signal may comprise modulation of an immune response, and in particular may involve modulation of Toll-like receptor signalling as part of this modulation process. An activation cluster may associate, for example, on the surface of a cell or within endosomes, and may comprise, for example, chaperonin 10 together with a Toll-like receptor agonist and a Toll-like receptor. Other molecules may also associate as part of an activation cluster, including, but not limited to, CD14.

BRIEF DESCRIPTION OF THE DRAWINGS

The present invention will now be described, by way of non-limiting example only, with reference to the accompanying drawings.

Figure 5A:
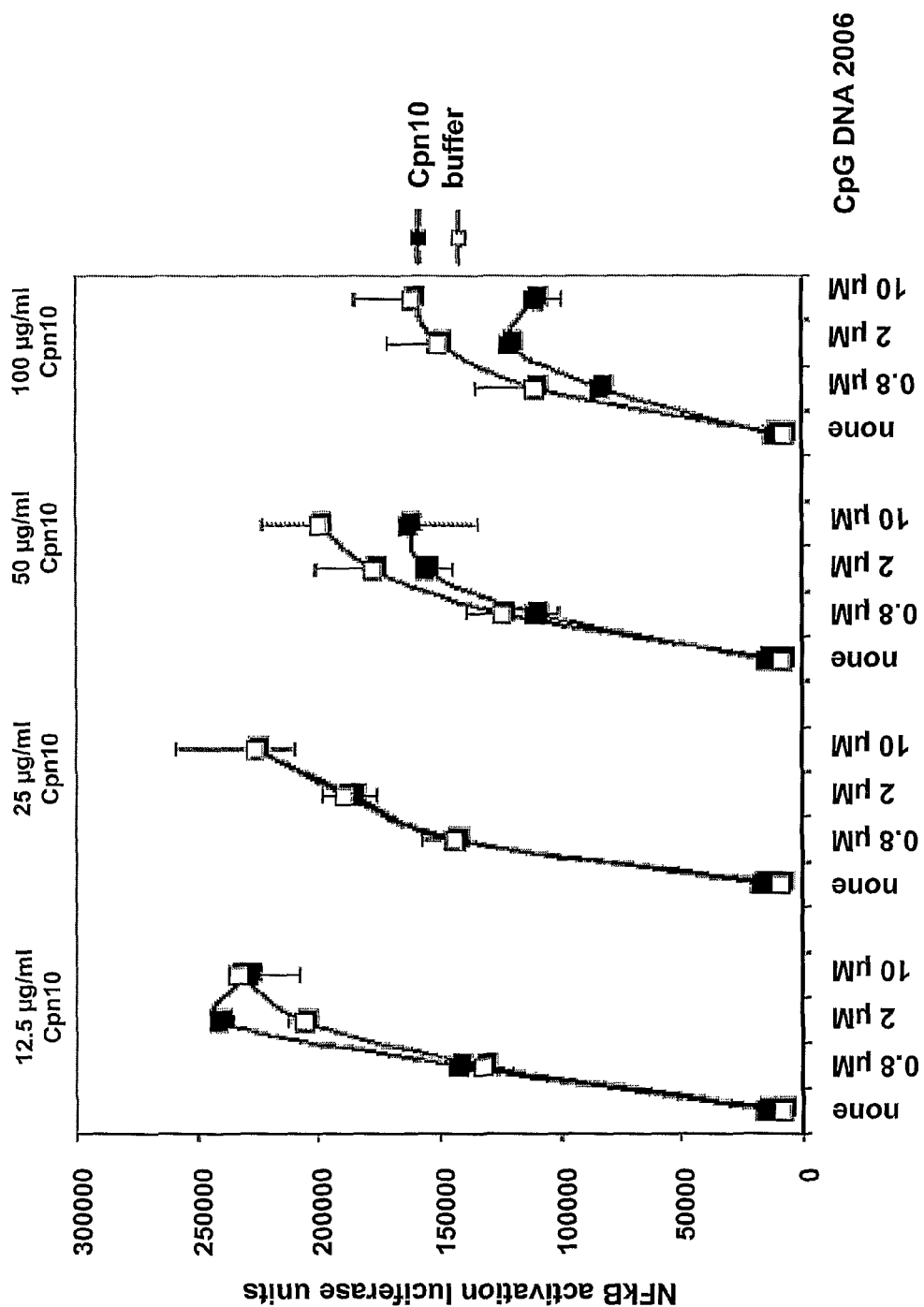
Figure 5B:
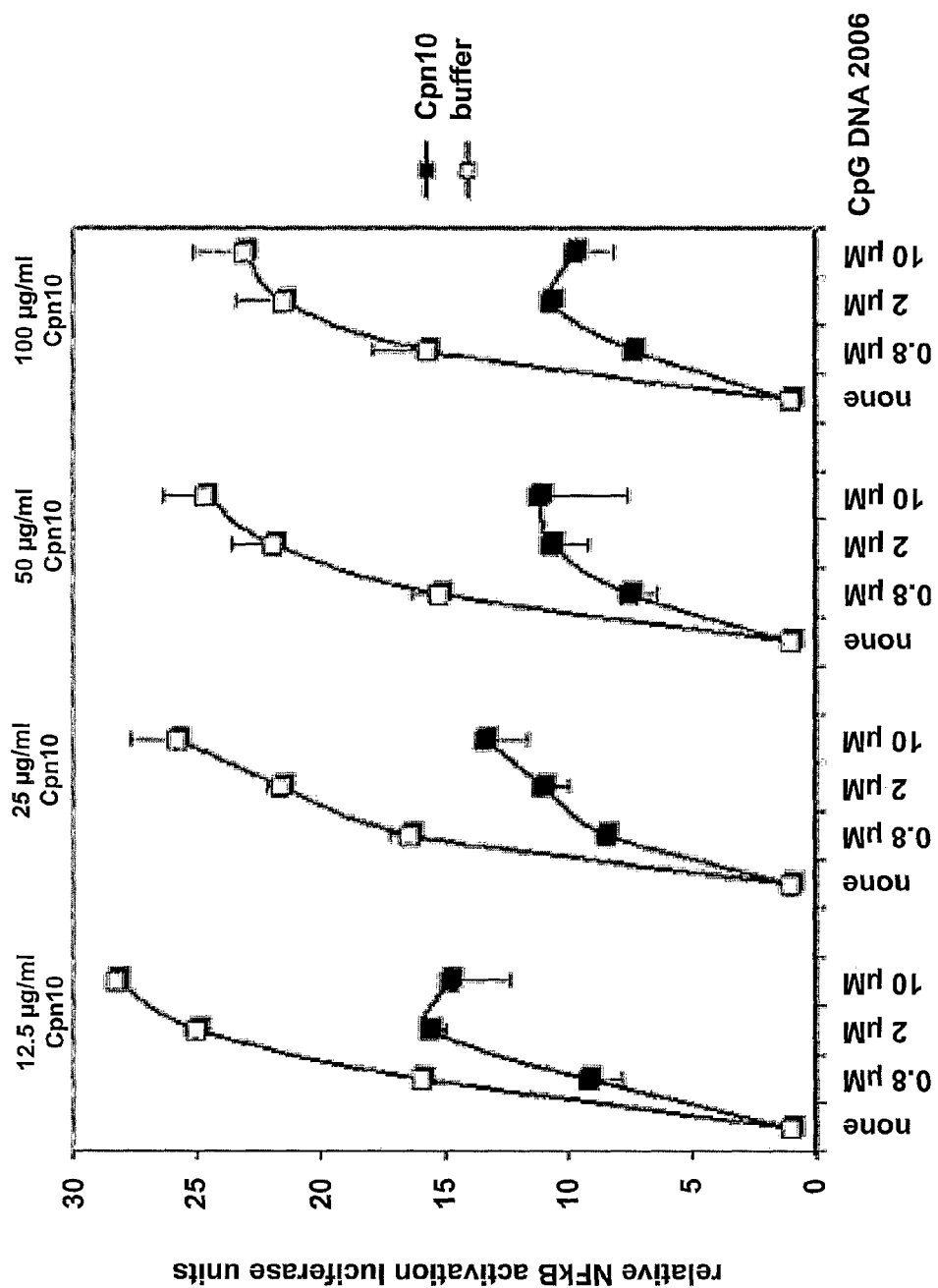

FIG. 5. Effect of recombinant human Cpn10 concentration (12.5 µg/ml, 25 µg/ml, 50 µg/ml and 100 µg/ml) on NF-κB activation (presented as A, luciferase units and B, relative luciferase units) in HE 93 cells transfected with TLR9-expressing construct and an NF-κB-luciferase reporter construct in the presence of CpG DNA (Cpn10 added simultaneously with agonist).

FIG. 6. A. TNF-α release (ng/ml) from human peripheral blood mononuclear cells (PBMCs) stimulated with re-purified lipopolysaccharide (LPS) and in the presence of varying concentrations of recombinant human Cpn10 (1 µg/ml, 10 µg/ml or 50 µg/ml) or in the absence of Cpn10 (added simultaneously with agonist). B. As for A, except PBMCs were first depleted of plasmacytoid dendritic cells (PDCs).

FIG. 7. A. IL-10 release (ng/ml) from human peripheral blood mononuclear cells (PBMCs) stimulated with re-purified lipopolysaccharide (LPS) and in the presence of varying concentrations of recombinant human Cpn10 (1 µg/ml, 10 µg/ml or 50 µg/ml) or in the absence of Cpn10. B. As for A, except PBMCs were first depleted of plasmacytoid dendritic cells (PDCs).

Figure 8:
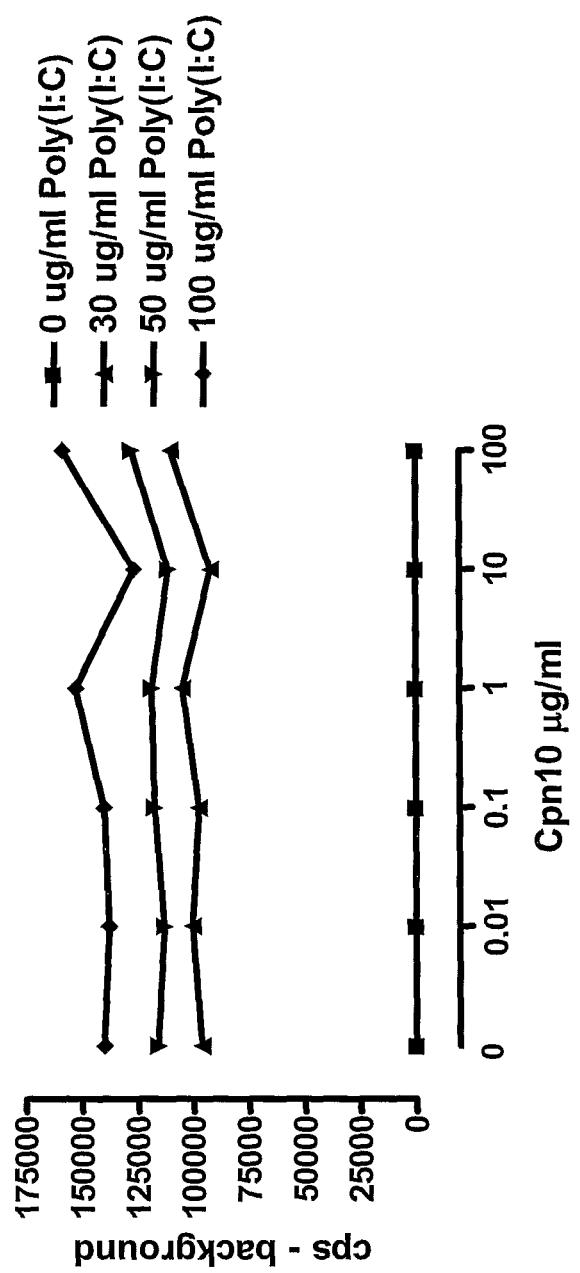

FIG. 8. Cpn10 does not reduce NF-κB activation through Poly(I:C) in the RAW264-pNifty2-LUC cell line.

Figure 9:
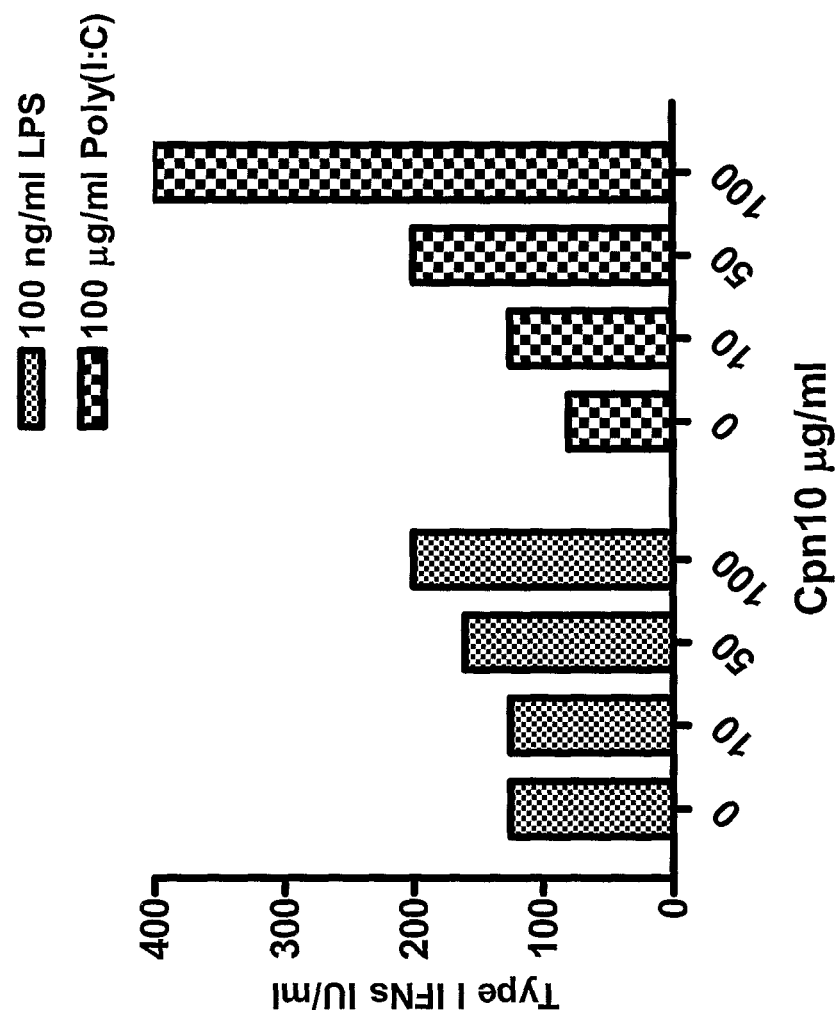

FIG. 9. Cpn10 dose-responsively promotes production of Type I IFNs in RAW264.7 cells stimulated by LPS (predominantly IFN-β) or Poly(I:C) (predominantly IFN-α) for 24 hours.

Figure 10:
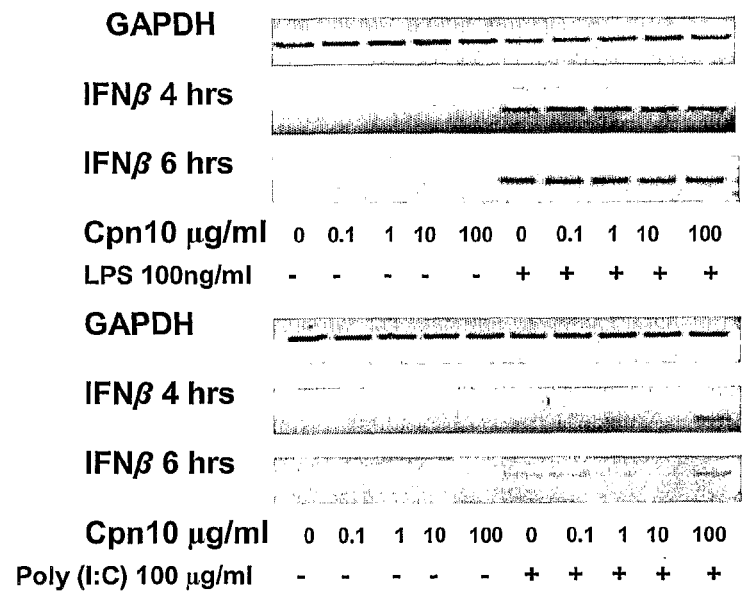

FIG. 10. Cpn10 dose-responsively promotes production of IFNβ at the transcriptional level in RAW264.7 cells stimulated with Poly(I:C). Potentiation of IFNβ in the presence of Cpn10 is also seen in RAW264.7 cells stimulated with LPS.

Figure 11:
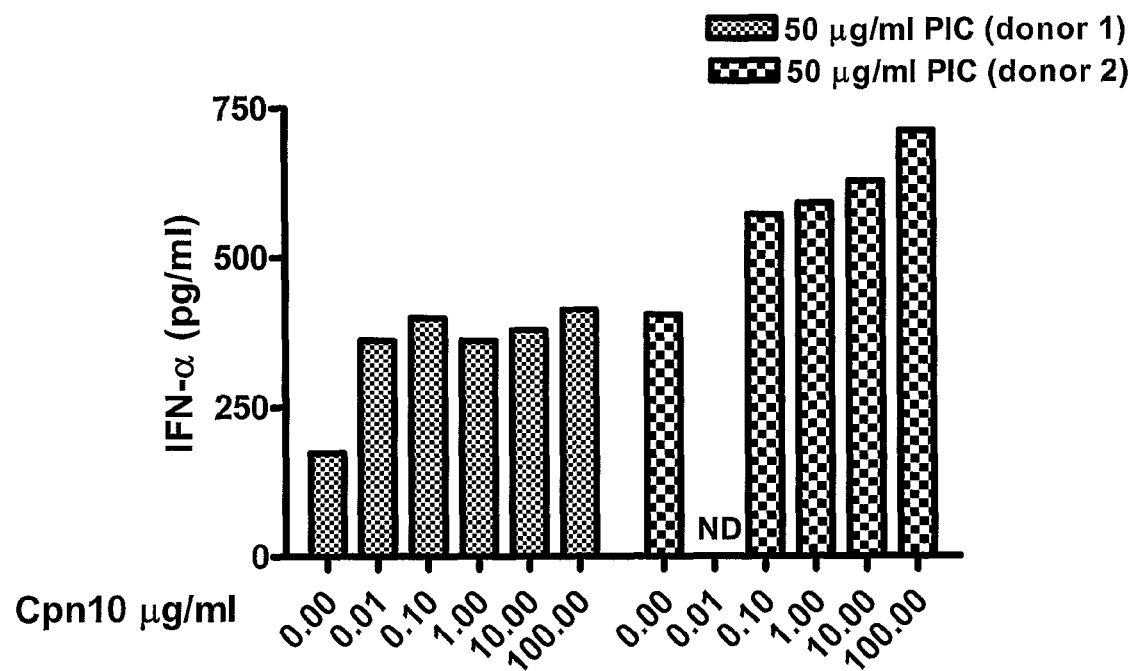

FIG. 11. Human PBMC from two different donors stimulated with 50 µg/ml Poly(I:C) produce increased levels of IFN-α in the presence of Cpn10.

Figure 12:
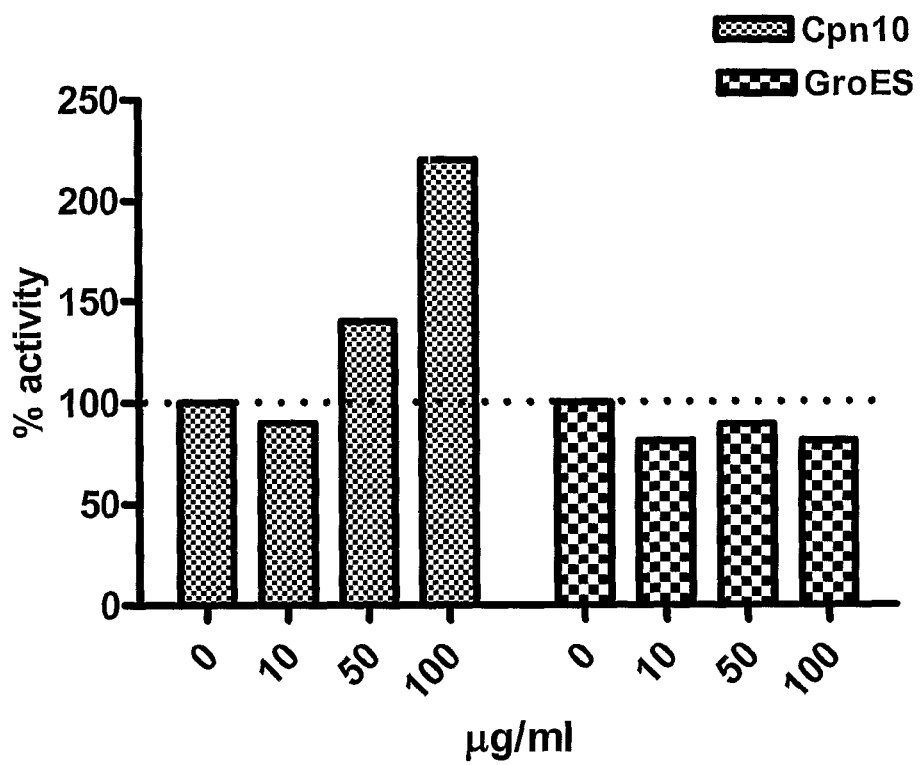

FIG. 12. Cpn10, but not GroES, induces a dose-responsive increase in Poly(I:C)-induced IFN-β.

Figure 13:
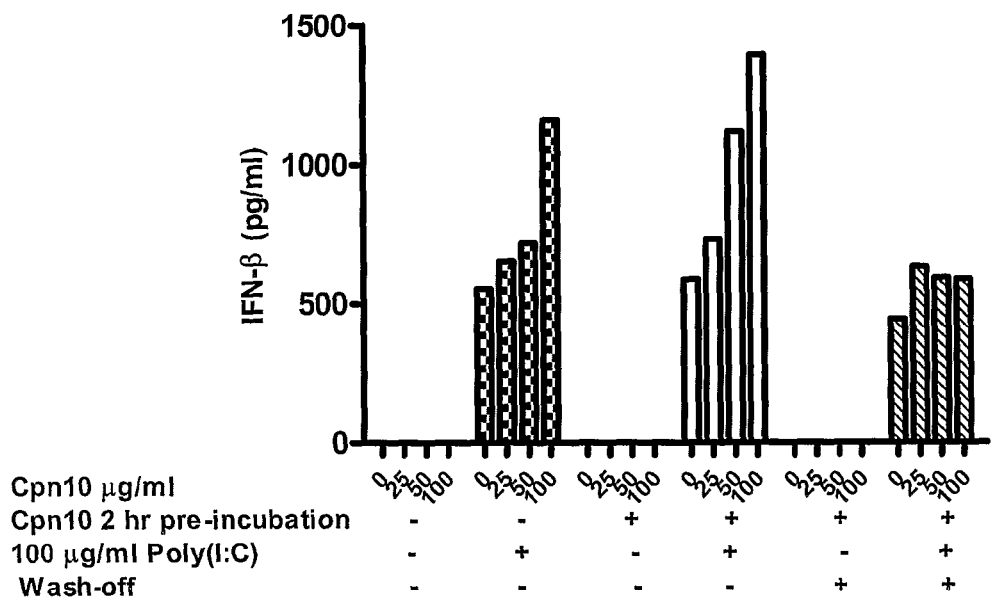

FIG. 13. Cpn10 pre-incubation followed by wash reduces the Cpn10 dose-responsive increase in Poly(I:C)-induced IFN-β production.

Figure 14:
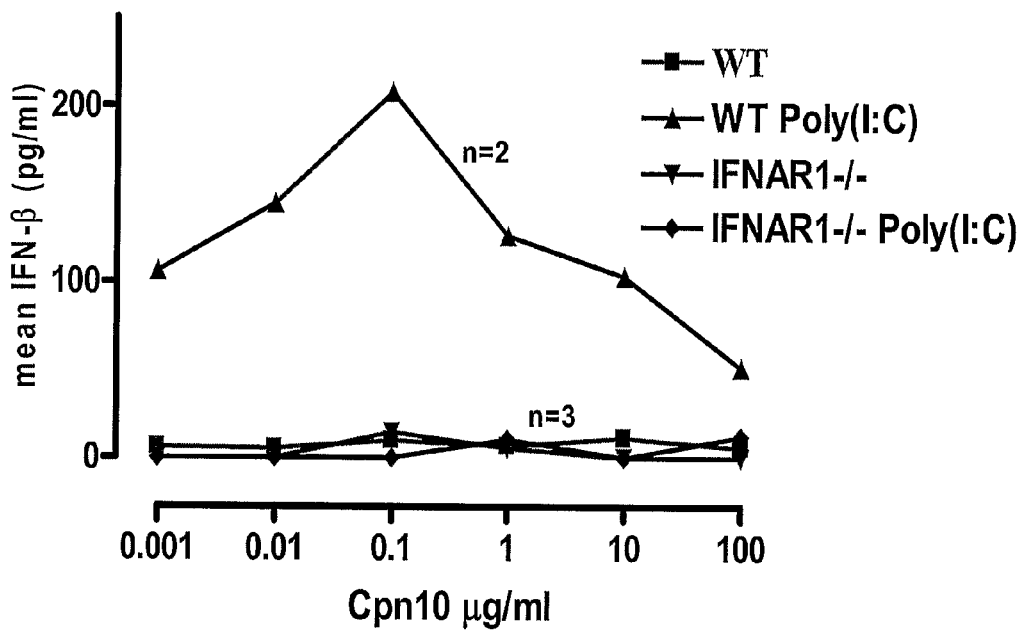

FIG. 14. Cpn10 does not potentiate an IFNβ response in BMM from IFNAR1−/− mice.

Figure 15:
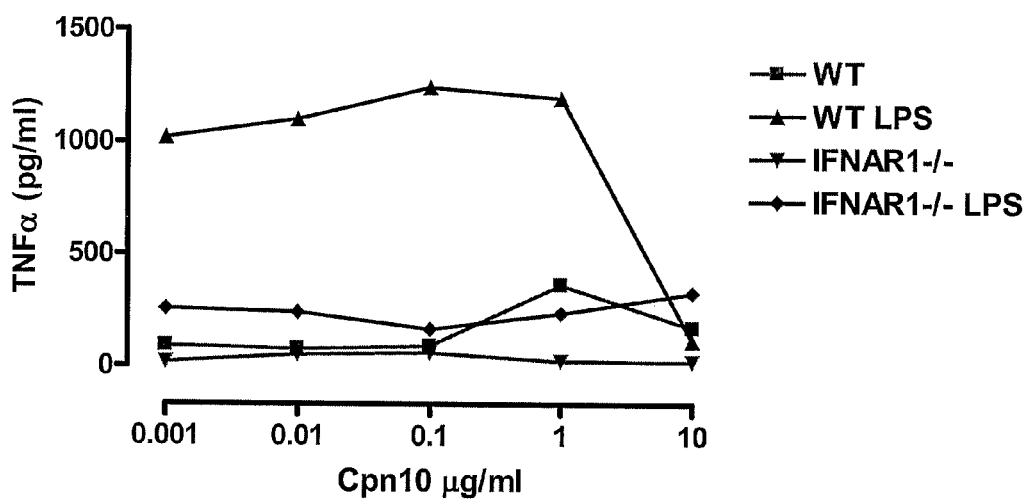

FIG. 15. Macrophage priming through the type I interferon pathway is required for Cpn10 modulation of a TLR4 response (n=2).

Figure 16:
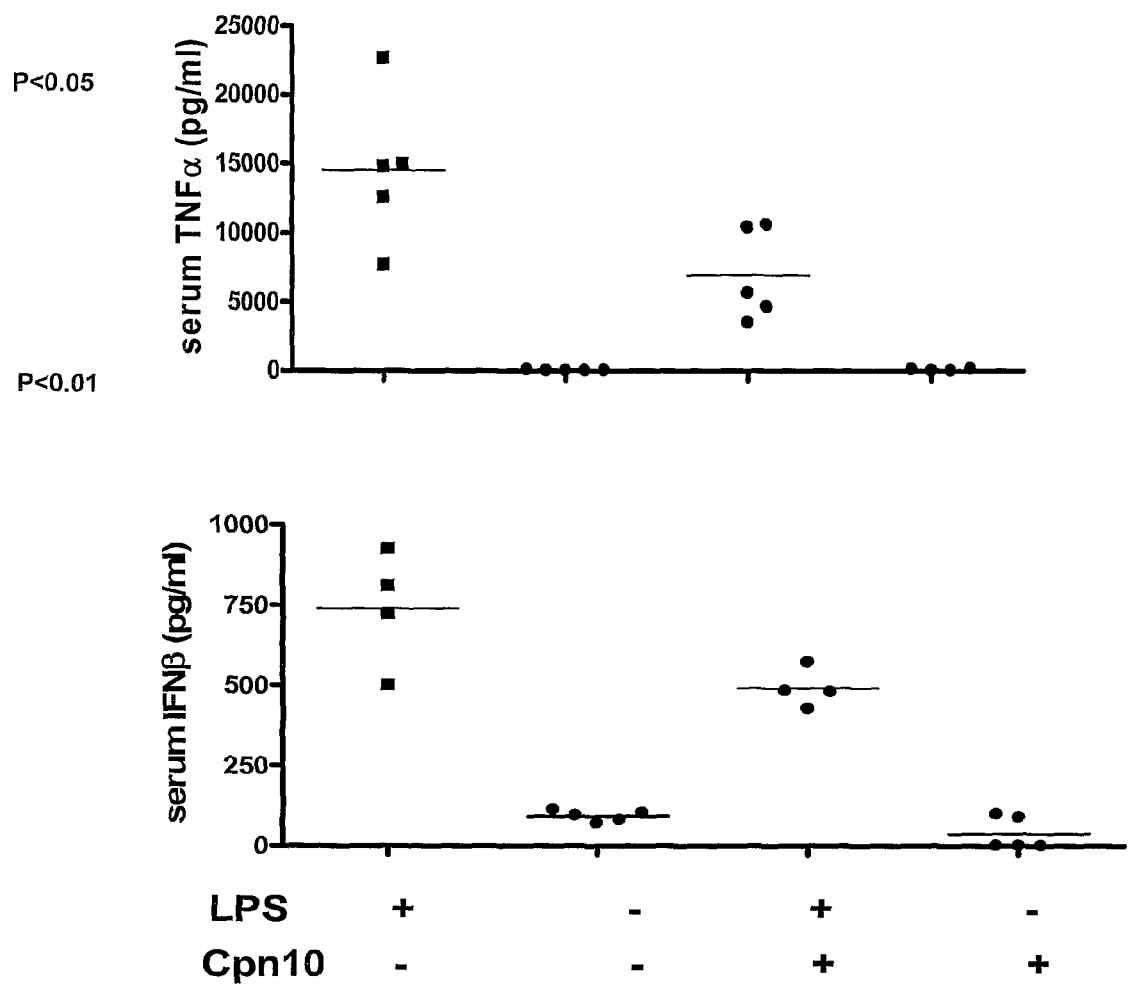

FIG. 16. Serum TNFα and IFNβ levels in mice with LPS-induced systemic inflammation.

Figure 17:
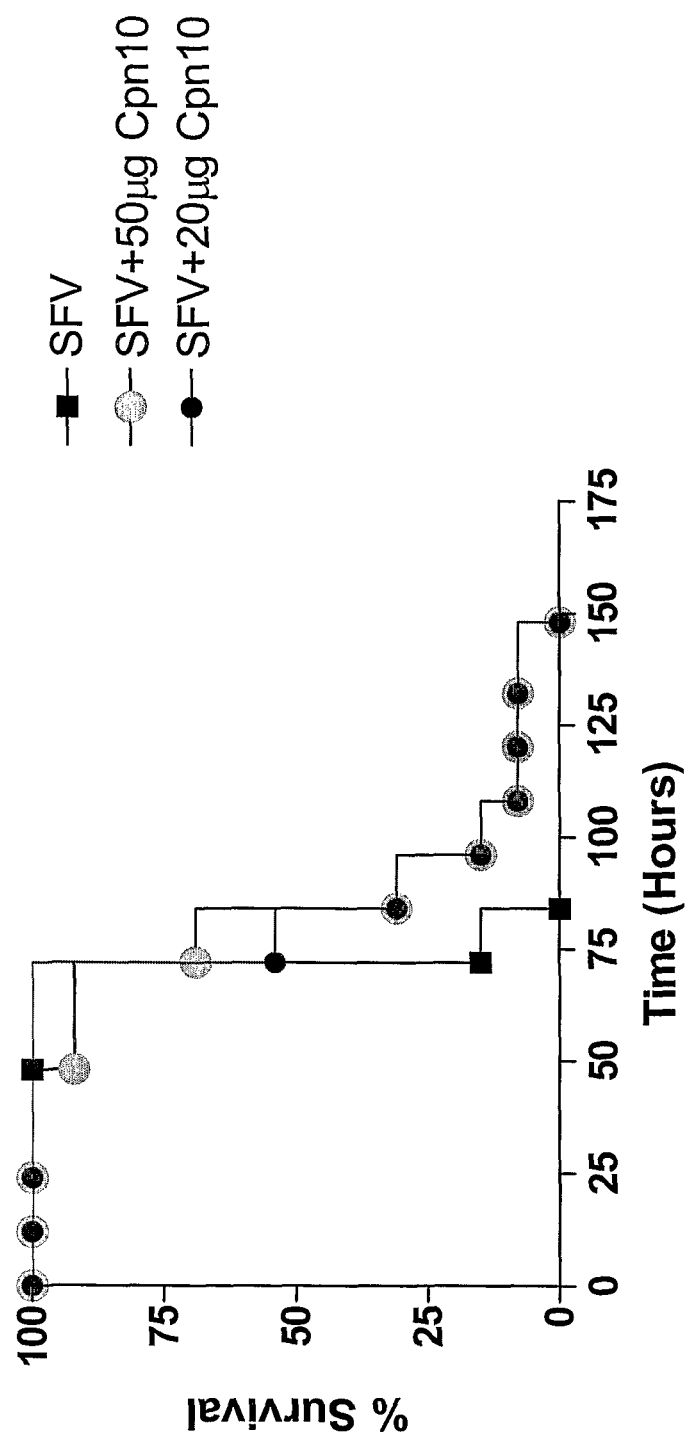

FIG. 17. Survival of 6-9 day old neonate C57BL/6 mice infected with SFV. 6-9 day old neonate C57BL/6 mice were used as follows: Group A: SFV (n=13); Group B: SFV+Cpn10 20 µg (n=13); Group C: SFV+Cpn10 50 µg (n=13). Group B and C were injected i.p. with 20 and 50 µg of Cpn10, followed (3 hrs later) by injection of 50 µl SFV (30×TCID50) to all three groups. Survival is plotted according to the legend as shown.

Figure 18:
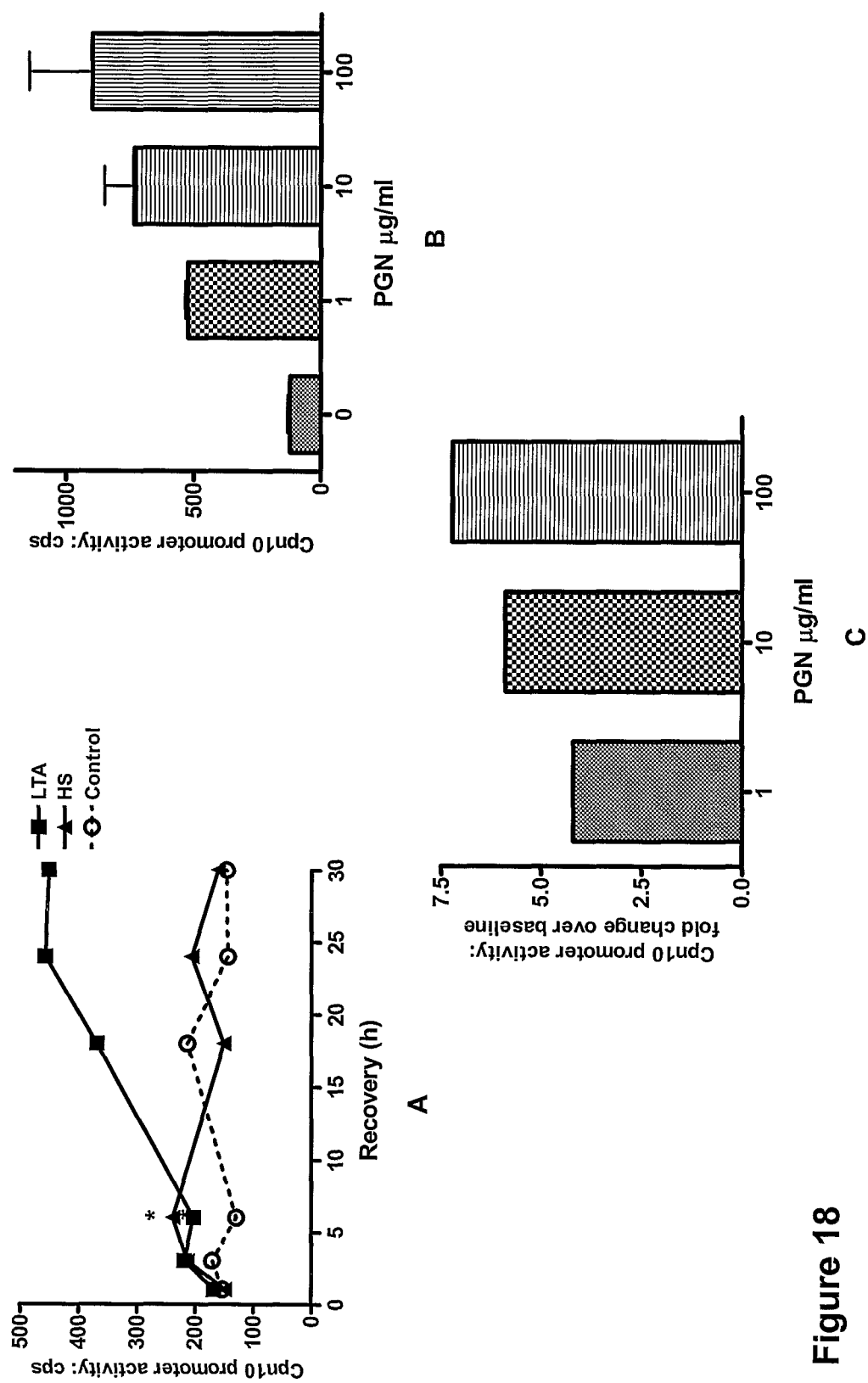
Figure 18:
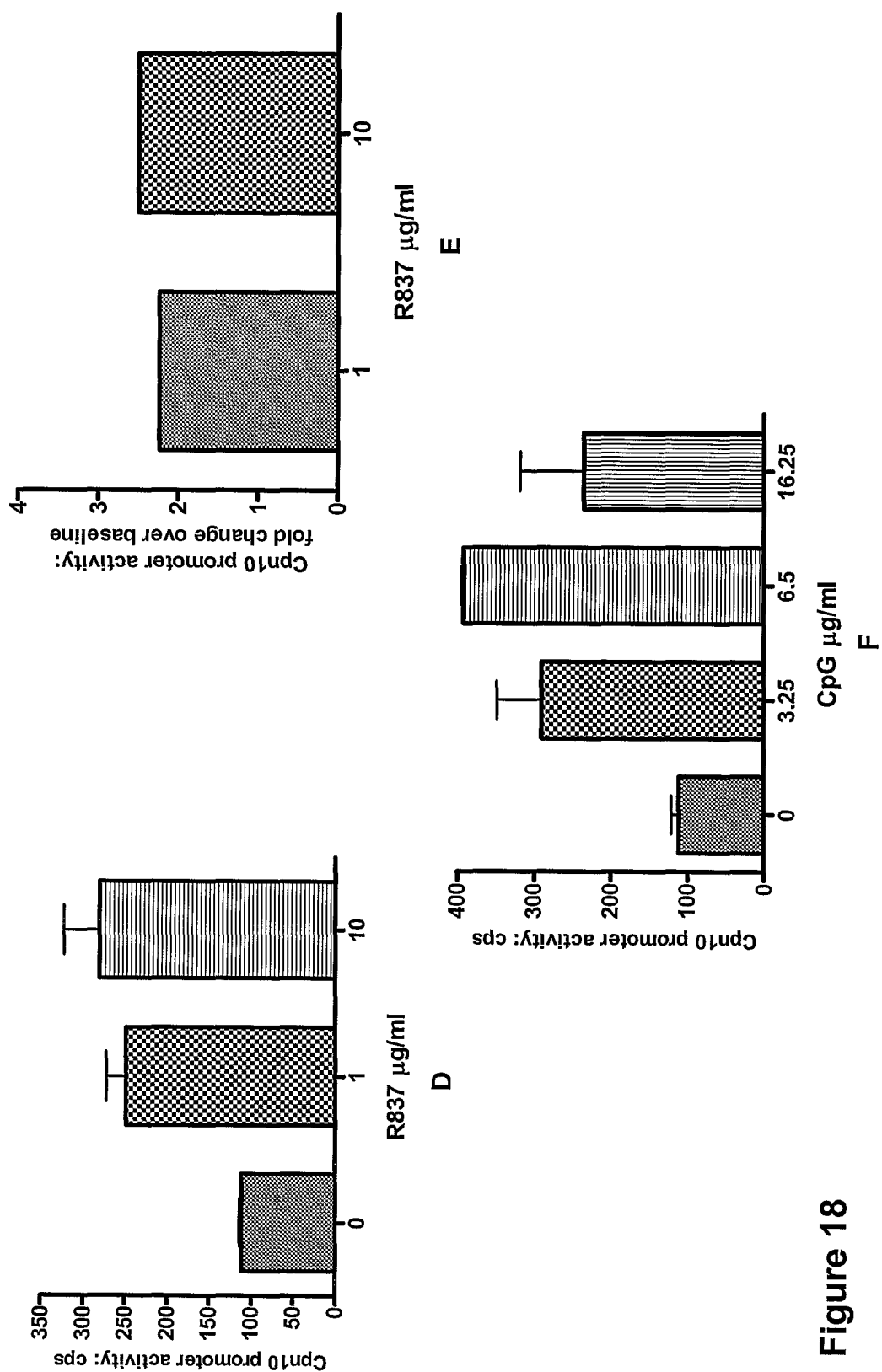
Figure 18:
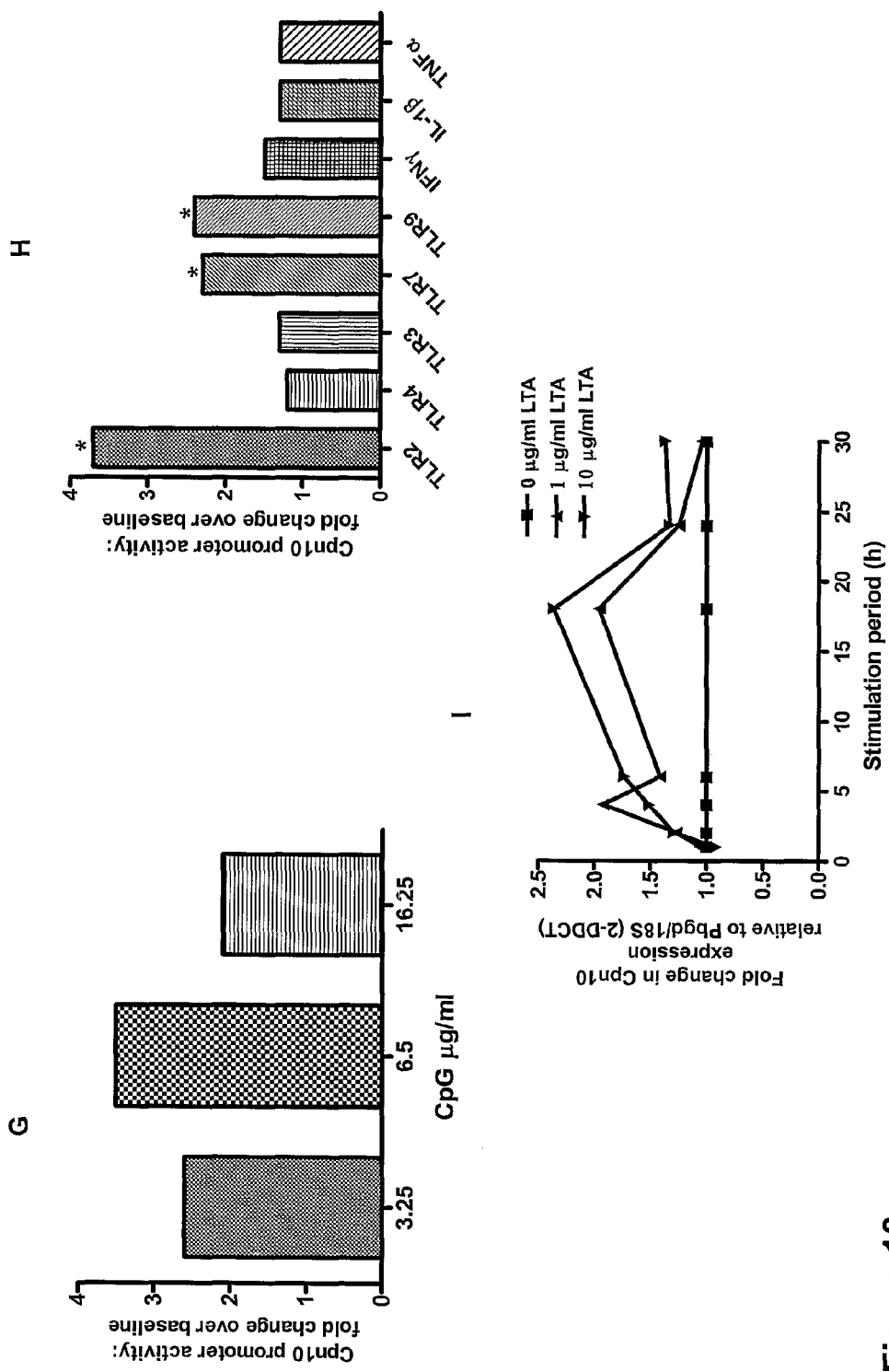

FIG. 18. The Cpn10 promoter is induced by stimulation of heat shock (HS) and stimulation of TLR. Representative assays demonstrate that heat shock with 6 hr recovery significantly induced Cpn10 promoter activity, which then returned to basal levels by 18 hr post HS (n=2 replicate assays) (A). By contrast, stimulation with LTA (TLR2 agonist) led to a 2.7-fold induction of the promoter by 24 hour stimulation and remained constant at 30 hours (A). Stimulation of cells with a titration of TLR2 (B,C), TLR7 (D,E) or TLR9 (F,G) ligands induced the Cpn10 promoter in a dose-dependent manner (n=2-6 replicates). Data presented in C, E and G reflect the same data as in B, D and F but are represented as fold change over baseline. Error bars reflect one SD of the mean. TLR agonists and cytokines induced the Cpn10 promoter with varying maximal levels (H). Cpn10 promoter activity is expressed as luciferase cps normalized against basal levels for each agonist. Optimal agonist concentrations and assays repeats: TLR2: *B. subtilis* LTA 100 µg/ml, n=12; TLR3: 100 µg/ml poly(I:C), n=6; TLR4: ultrapure *E. coli* LPS 10 ng/ml, n=12; TLR7: imiquimod R837 10 µg/ml, n=2; TLR9, CpG ODN 1 mM, n=2; IFNγ 1 ng/ml, n=3, IL-1β (1 ng/ml), n=2, TNF-α (100 ng/ml), n=2 (H). Significance (p<0.02) for (A) and (p<0.05) for (F) was assessed ANOVA and is indicated by *. cps=counts per second. In non-transfected RAW264.7 cells stimulated with LTA, a transient concentration-dependent increase in Cpn10 mRNA levels was measured by real-time PCR (I). Gene expression was normalized to control housekeeper genes (18S and Pbgd).

Figure 19:
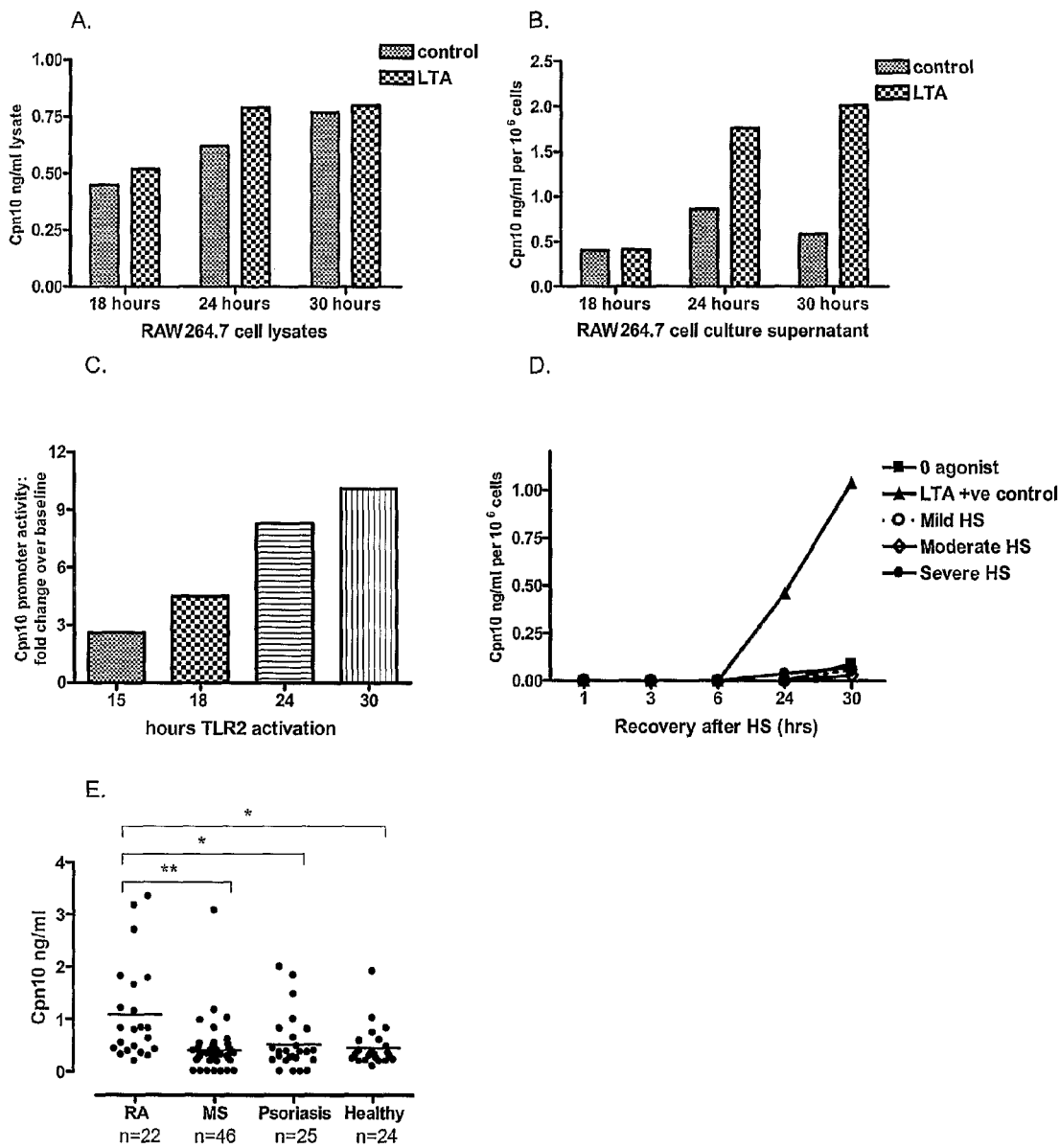

FIG. 19. TLR agonists and heat shock induce Cpn10 production but only TLR agonists result in extracellular release of Cpn10. Quantitative analysis of LTA-stimulated RAW264.7 total cell lysates by ELISA showed little change in Cpn10 levels between treated and control cells (A), however analysis of the culture supernatants demonstrated a 3-fold increase in extracellular Cpn10 after 30 h 100 µg/ml LTA stimulation (B). Supernatant Cpn10 was normalized against the number of cells per well. Time course analysis demonstrated persistent Cpn10 promoter activation over 30 h in response to TLR2 ligation. Results were standardized according to sample protein concentration (C). Mild, moderate or severe heat shock of RAW264.7 cells did not induce the extracellular release of Cpn10 (D). Levels of Cpn10 in the circulating blood of RA patients are significantly higher than in patients with MS or psoriasis, or healthy control subjects. Significance was analyzed by one-way ANOVA with Tukey's post-test and is indicated by * (p<0.01), or ** (P<0.001) (E).

Figure 20:
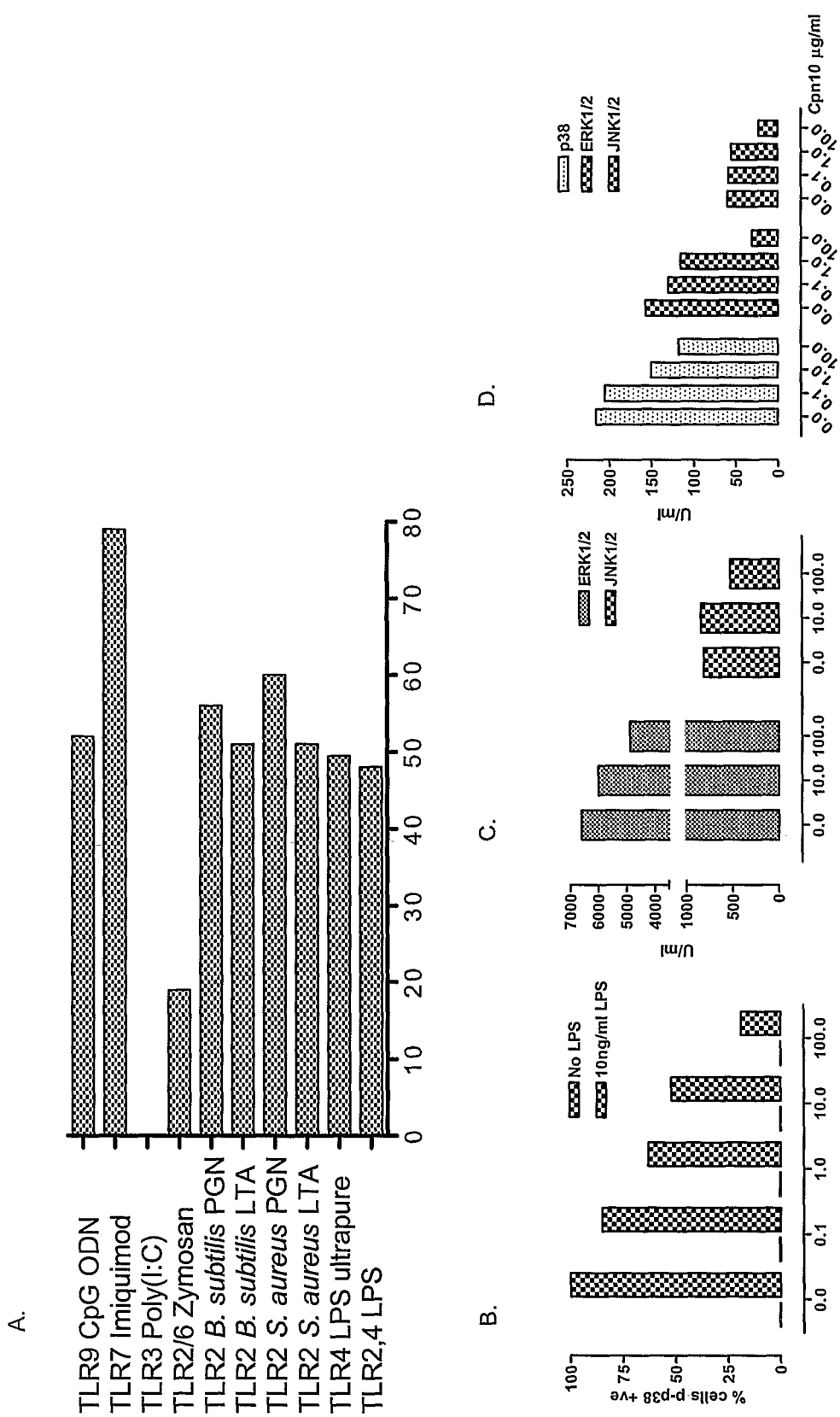
Figure 20:
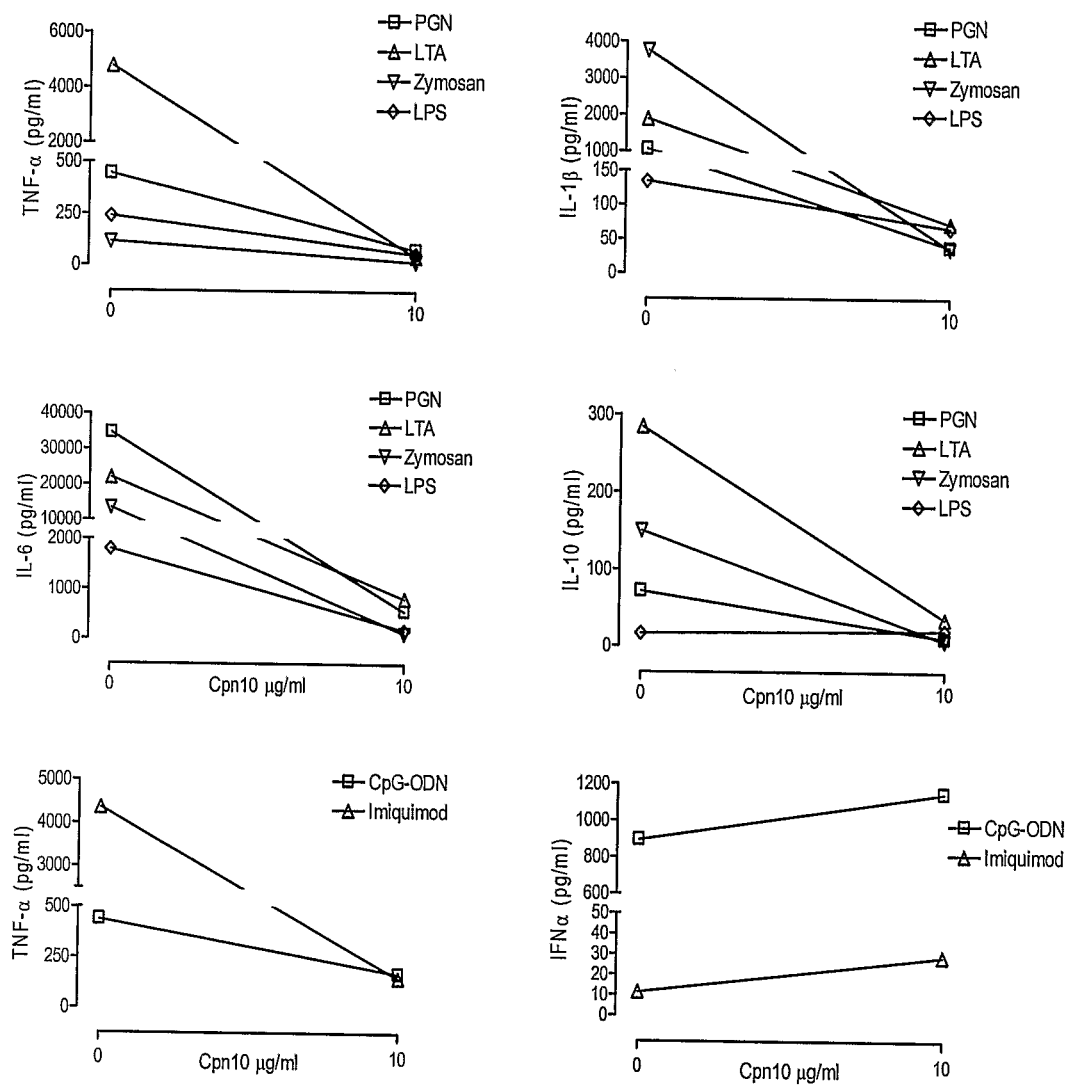

FIG. 20. Cpn10 limits agonist-induced signaling through a number of TLRs. RAW264.7 cells stably transfected with the HIV-LTR-LUC promoter construct were pre-incubated with Cpn10 prior to stimulation with a variety of TLR ligands, resulting in inhibition of luciferase activity, a measure of NF-κB activation in these cells (A). Agonist concentrations and time of incubation were: CpG ODN 16.25 µg/ml, 4 h; imiquimod 10 µg/ml, 2 h; poly(I:C) 100 µg/ml, 4 h; zymosan 10 µg/ml, 2 h; PGN 10 µg/ml, 2 h; PGN 10 µg/ml, 2 h; ultrapure LPS 10 ng/ml, 2 h; LPS 5 ng/ml, 2 h. Cpn10 pre-incubation of RAW264.7 cells (B,C) or human PBMC (D) followed by LPS stimulation (10 ng/ml in RAW264.7 cells, 100 ng/ml in PBMC) leads to a dose-responsive reduction in levels of phosphorylated MAPK signals. Stimulation of human PBMC with ligands to TLRs 2, 2/6, 4, 7, 9 in the presence of Cpn10 results in decreased levels of TNF-α, IL-1β, IL-6, and IL-10, and increased imiquimod- and CpG ODN-induced IFNα production (E). Concentrations of ligands used were: 10 µg/ml PGN, 10 µg/ml LTA, 10 Hg/ml zymosan, 0.12 ng/ml LPS, 6.5 µg/ml CpG ODN, 10 µg/ml imiquimod FIG. 21. RAW264 cells grown in suspension were incubated for 4 hr in the presence of 100 µg/ml Cpn10, or the equivalent volume of diluent buffer, and then stained for the presence of TLR4.

Figure 22:
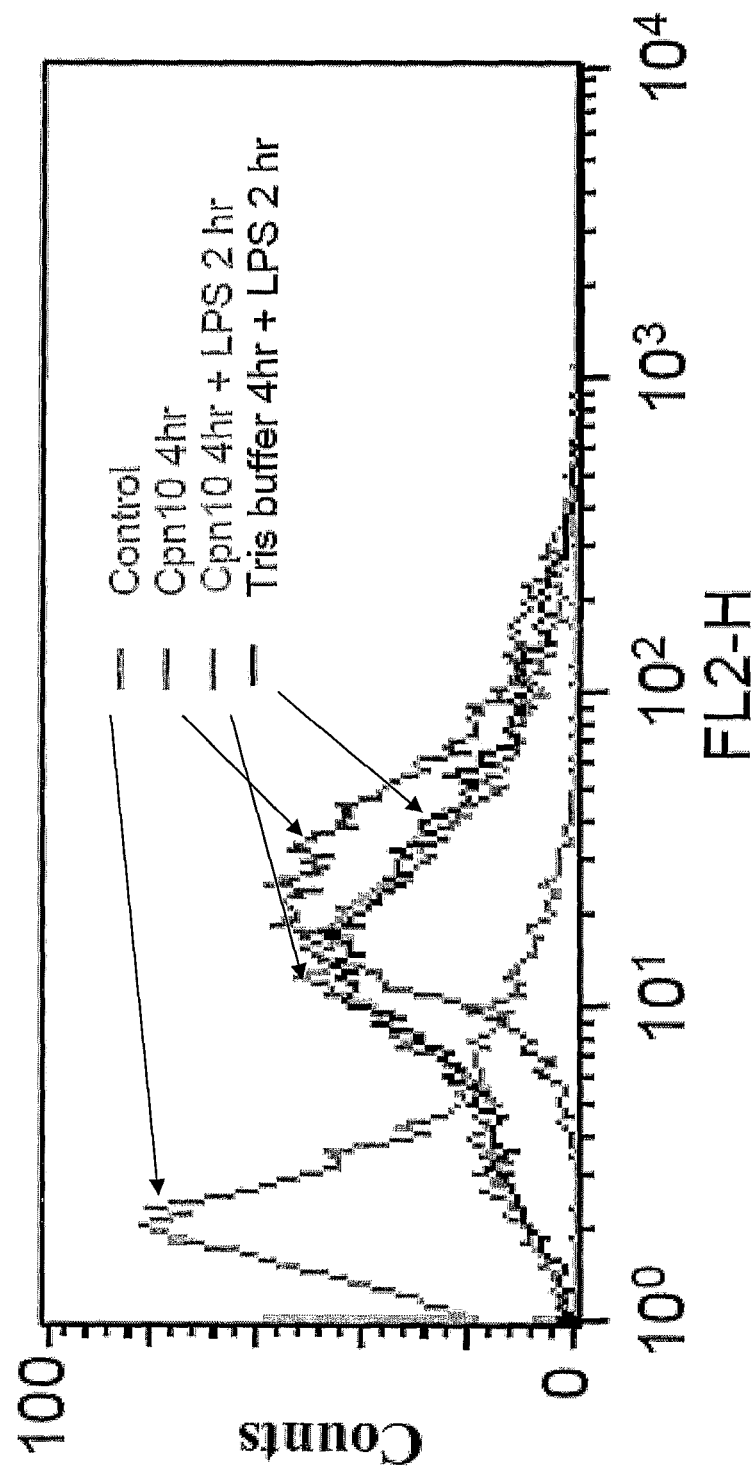

FIG. 22. RAW264 cells grown in suspension were incubated for 4 hr in the presence of 100 µg/ml Cpn10 or the equivalent volume of diluent buffer with or without 2 ng/ml LPS (added for the last 2 hr of Cpn10 treatment) and then stained for the presence of TLR4.

Figure 23:
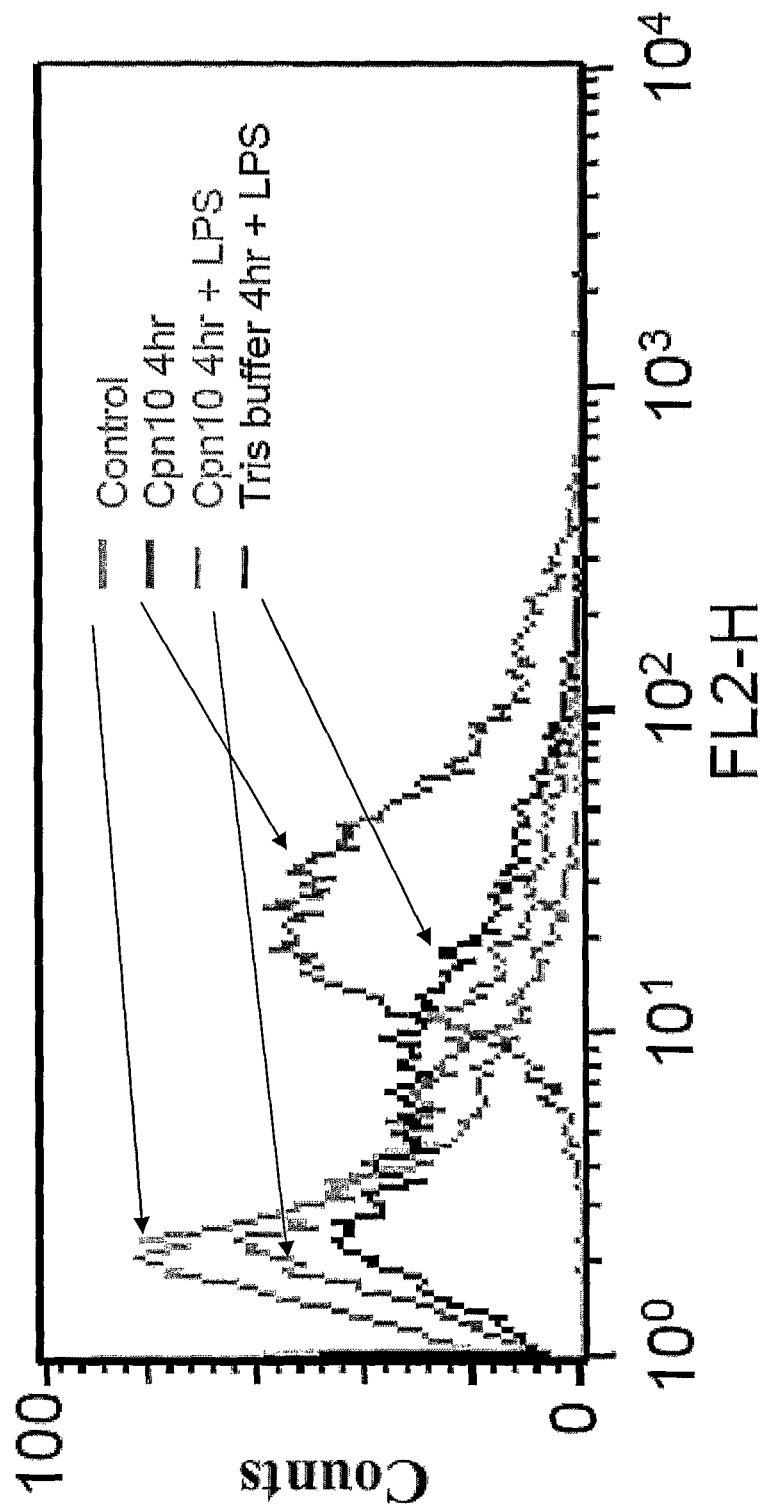

FIG. 23. RAW264 cells grown in suspension were incubated for 4 hr in the presence of 100 µg/ml Cpn10 or the equivalent volume of diluent buffer, with or without 20 ng/ml LPS added for the last 2 hr Cpn10 treatment, prior to staining for TLR4. (Mean fluorescence intensity: Orange: 4.39, Black: 6.14, Blue: 25)

Figure 24:
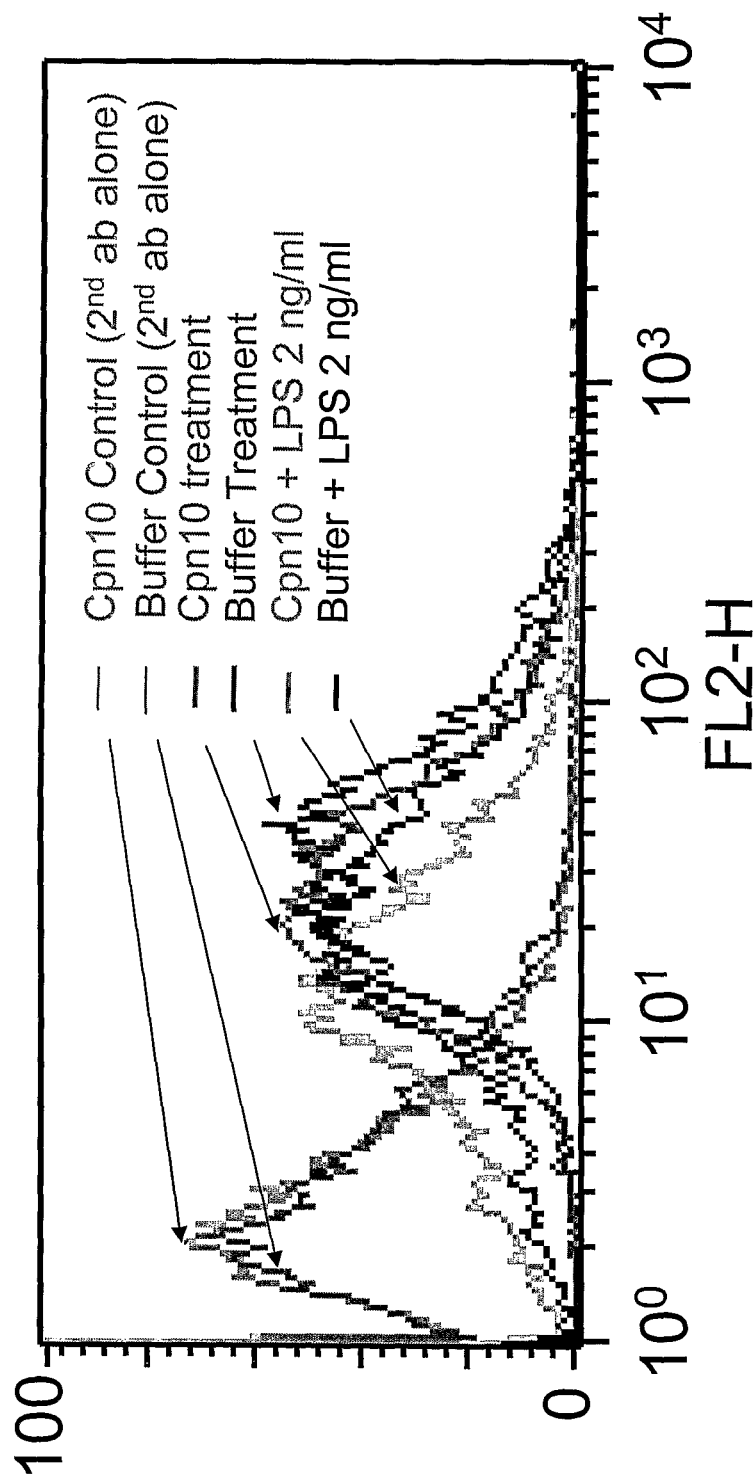

FIG. 24. RAW264 cells grown in suspension were incubated overnight in the presence of 100 µg/ml of Cpn10 or the equivalent volume of diluent buffer, with or without LPS (2 ng/ml) added for the last 2 hr of Cpn10 treatment, and were then stained for TLR4. Mean fluorescent intensity Blue—25, Red—33, Orange—11.7, Black—20.

Figure 25:
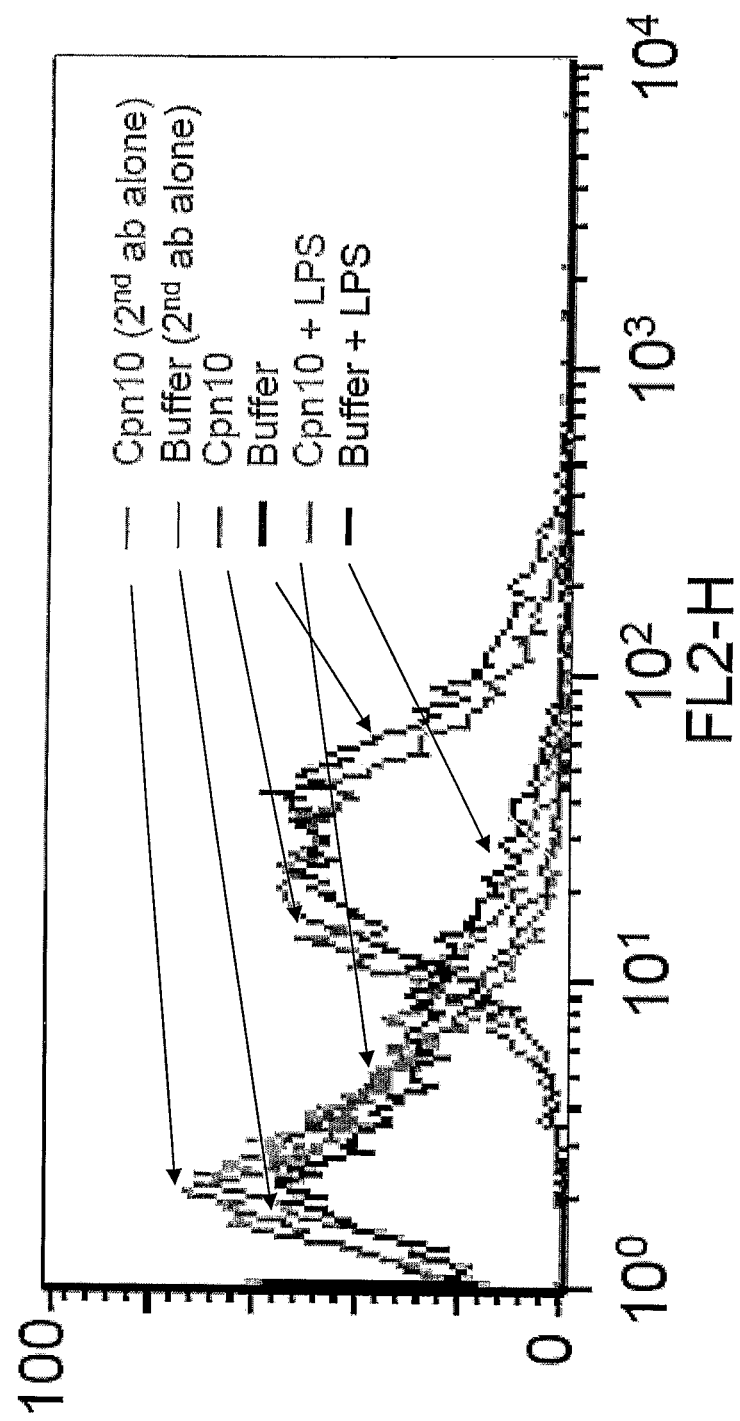

FIG. 25. RAW264 cells grown in suspension were incubated overnight in the presence of 100 µg/ml Cpn10 or the equivalent volume of diluent buffer, with or without 20 ng/ml LPS added for the last 2 hr Cpn10 treatment and then stained for TLR4. (Mean fluorescence intensity: Orange: 3.9, Black: 7.9)

Figure 26:
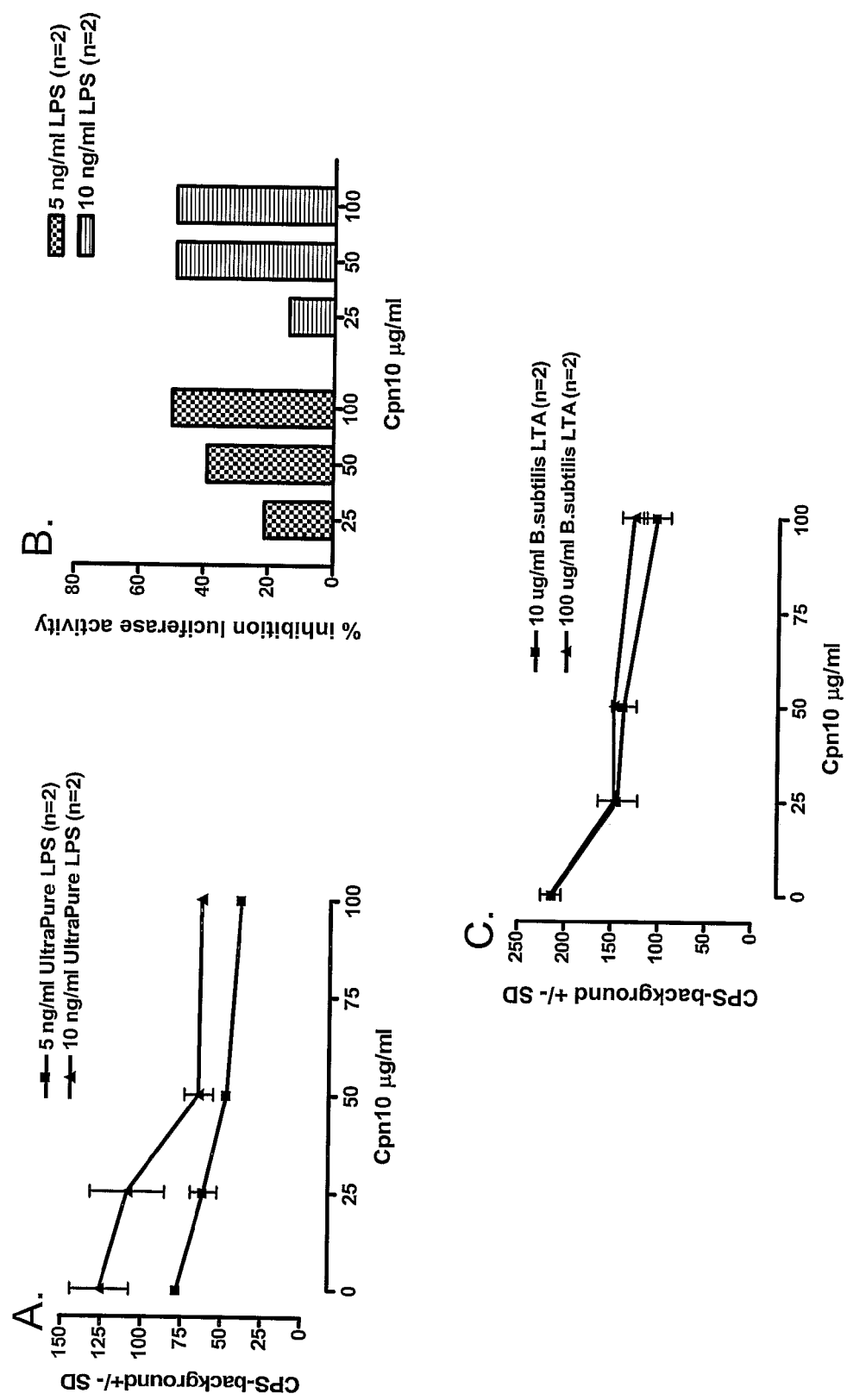
Figure 26:
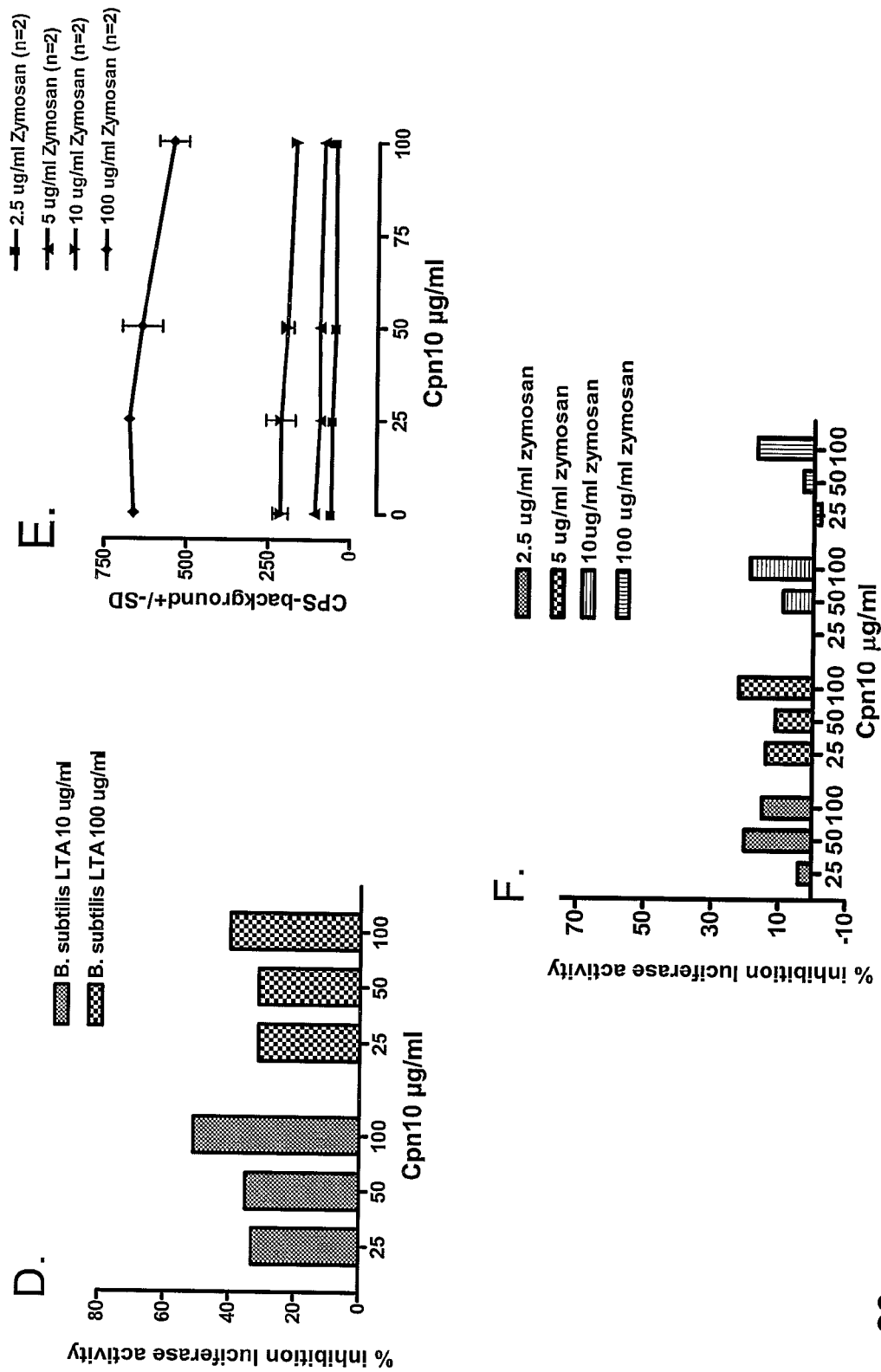
Figure 26:
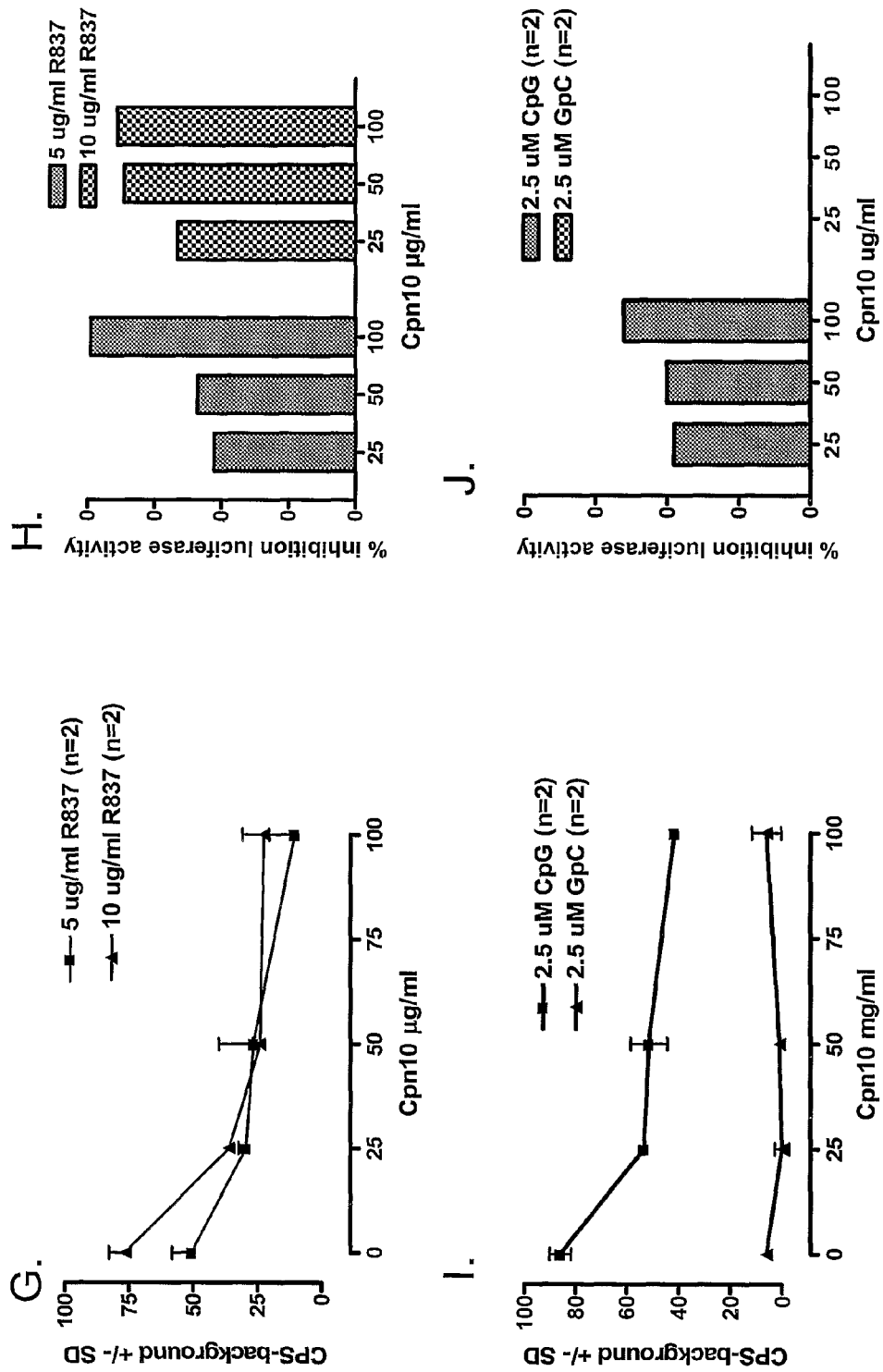

FIG. 26. Representative TLR ligands and the inhibition of luciferase activity by Cpn10. Data in A, C, E, G, I depict luciferase units in CPS, while B, D, F, H, J represent these data as percent inhibition of luciferase activity in RAW264-HIV-LTR-LUC cells stimulated with LPS.

Figure 27:
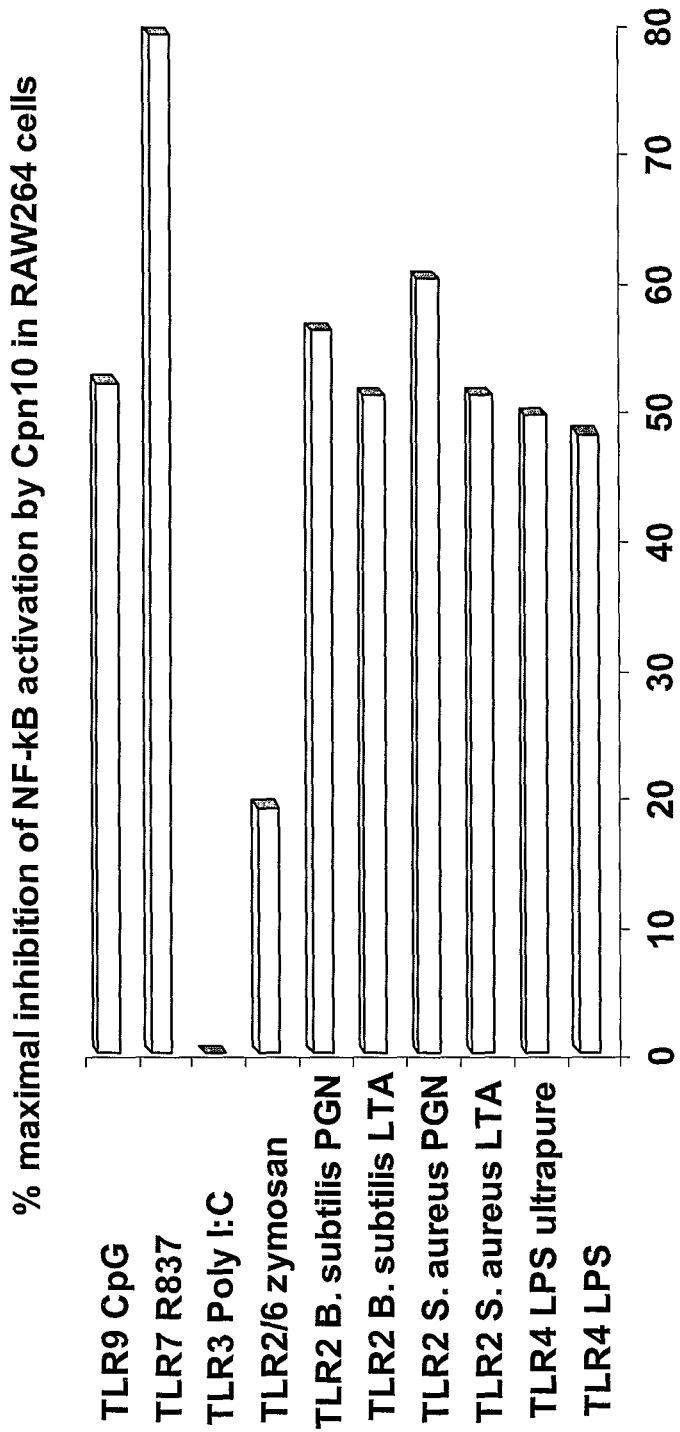

FIG. 27. Maximal Cpn10-induced inhibition of HIV-LTR activation stimulated by a broad range of TLR ligands, as an indirect measure of NF-κB activation.

Figure 28:
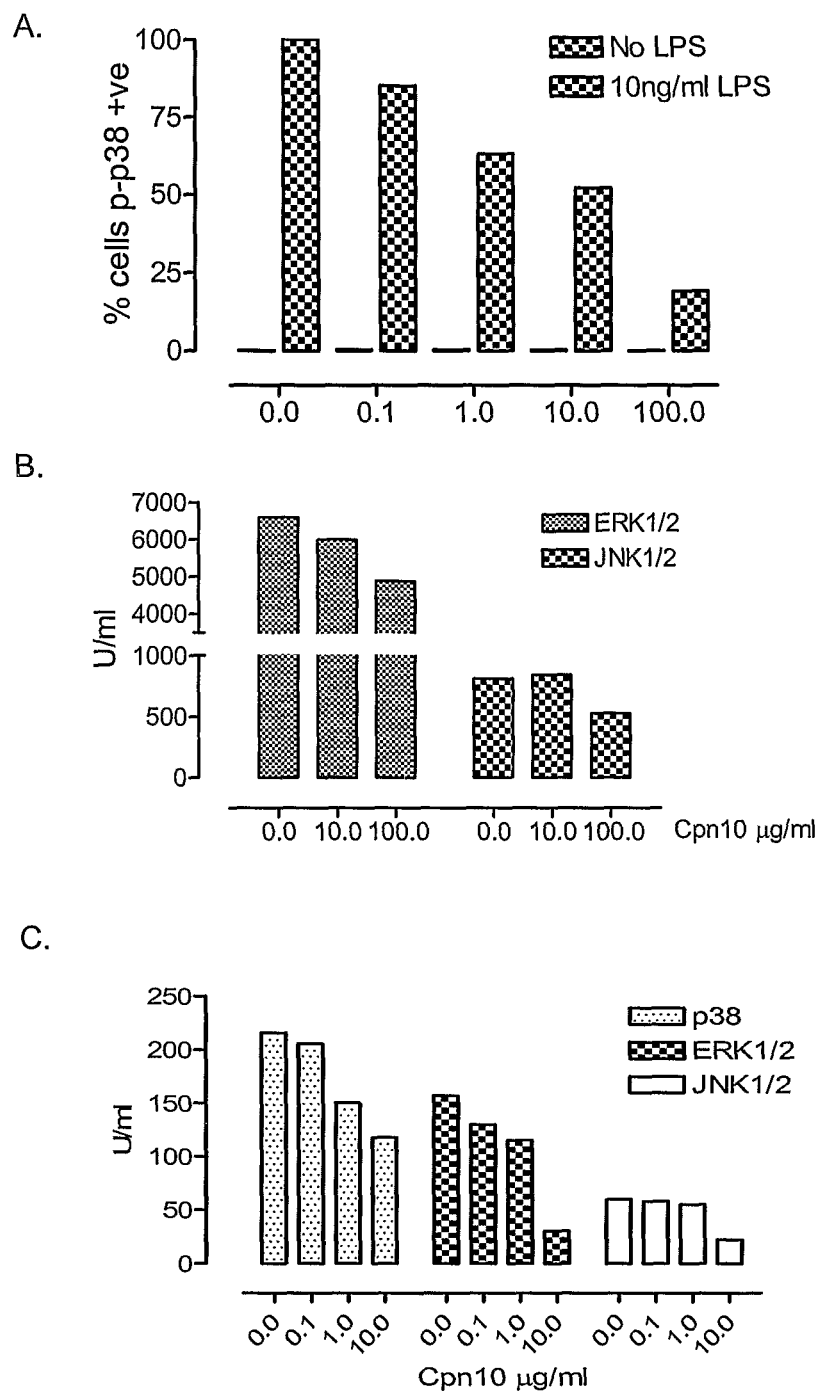

FIG. 28. Cpn10 dose-responsively reduces the level of phosphorylated p38 (A), ERK1/2, and JNK1/2 (B) in cells stimulated with LPS for 30 minutes. As shown for the murine macrophage cell line RAW264.7, Cpn10 dose-responsively reduced the level of LPS-induced phosphorylation of p38, ERK1/2, and JNK1/2 in freshly isolated human PBMC (C). Since activation of the MAP kinase pathway is closely linked with induction of the inflammatory cascade of cytokine production, these data show that Cpn10-mediated changes in ligand-induced cytokine production result from changes in the TLR signal cascade.

Figure 29:
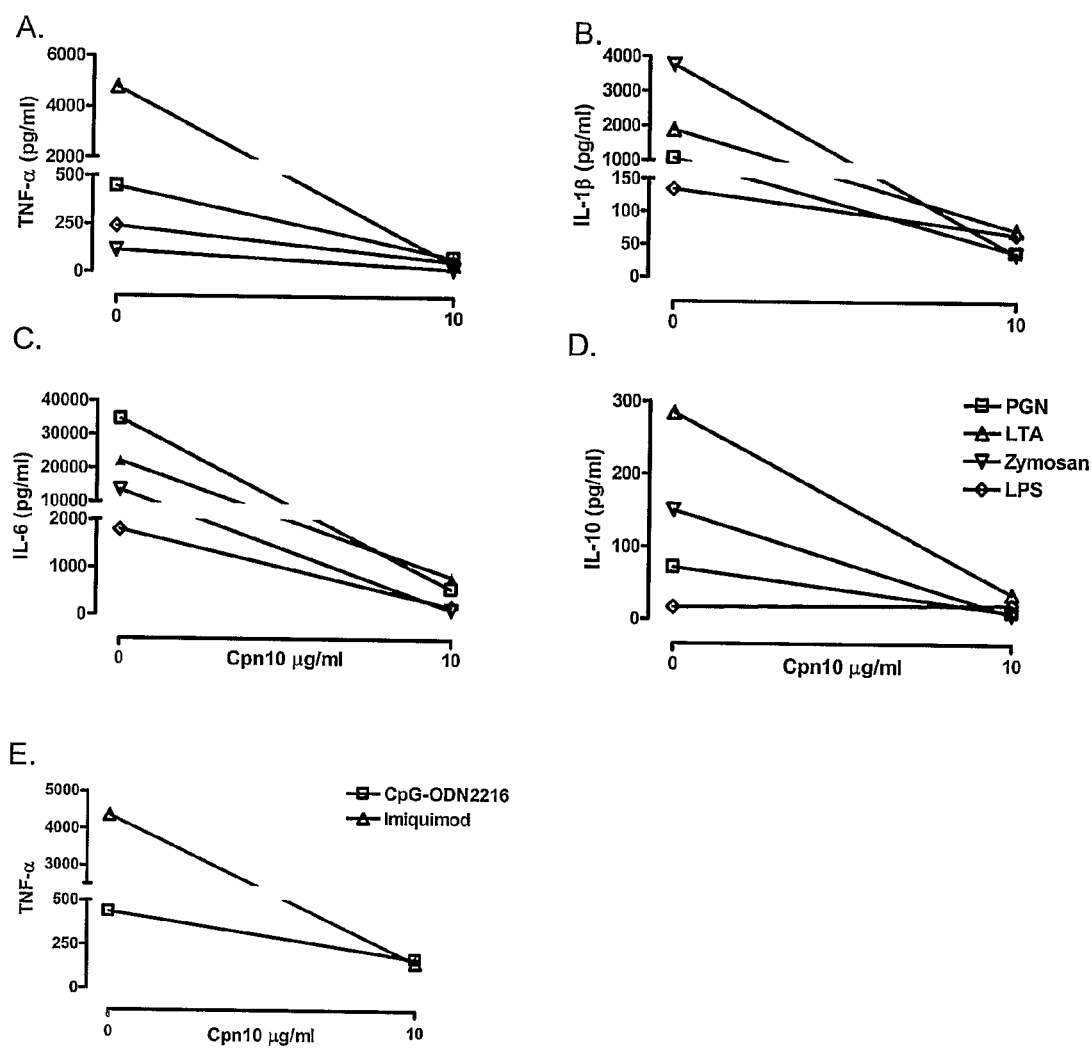

FIG. 29. Human PBMC stimulated with ligands to TLR2 (PGN, LTA), TLR2,6 (zymosan), TLR4 (LPS), TLR7 (Imiquimod), or TLR9 (CpG ODN2216) in the presence of Cpn10 results in decreased production of cytokines.

Figure 30:
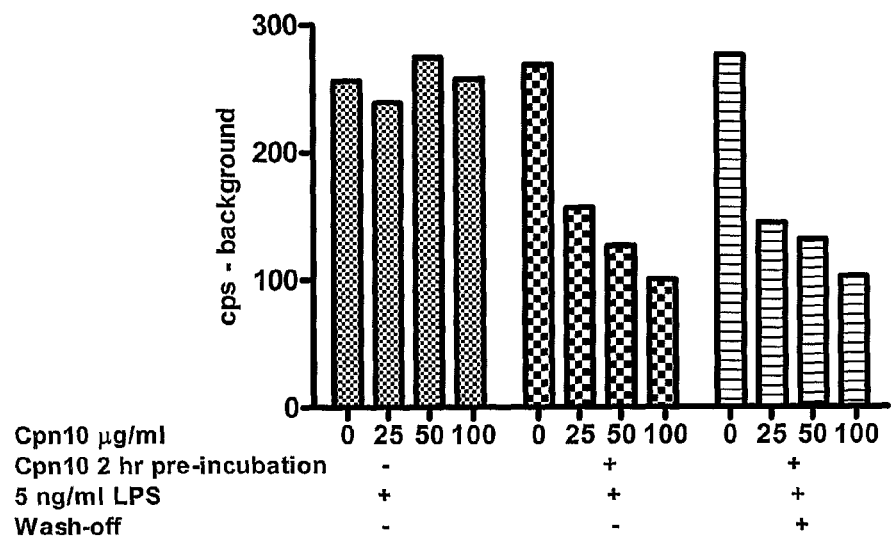

FIG. 30. Cpn10 pre-incubation followed by a wash prior to LPS addition still limits NF-κB activation in a dose-responsive manner.

Figure 31:
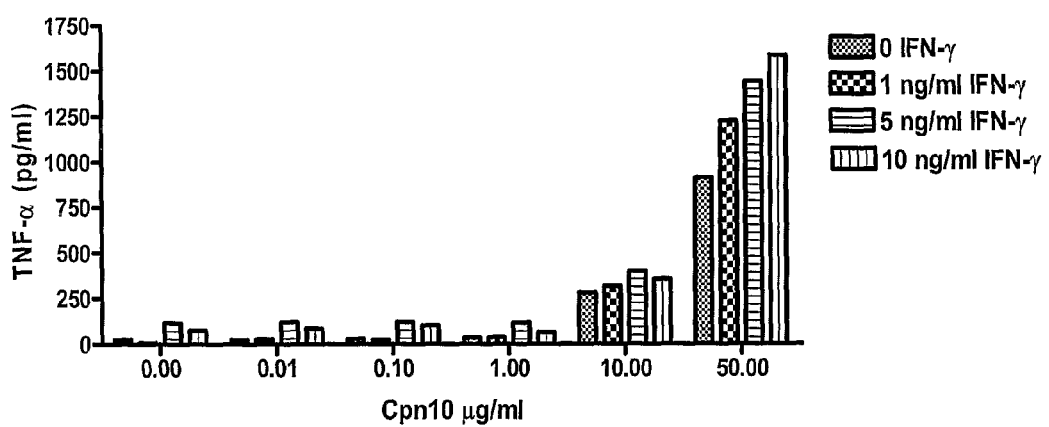

FIG. 31. Cpn10 pre-incubation followed by IFN-γ stimulation for 6 hours results in increased TNF-α production by RAW264.7 cells.

Figure 32:
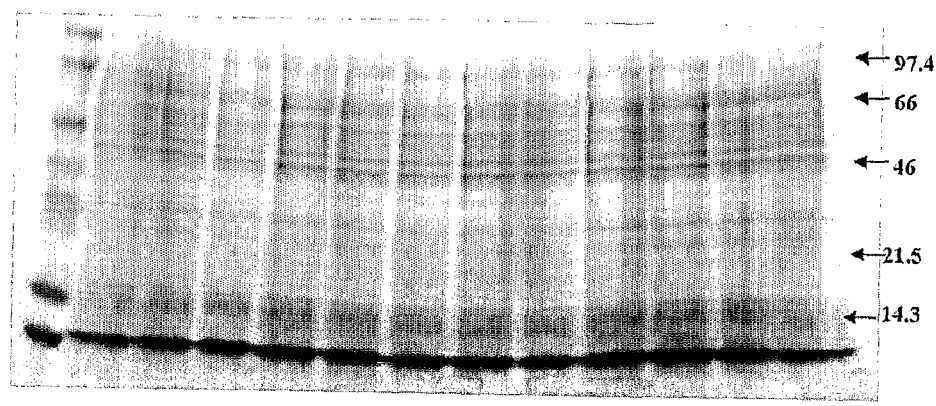

FIG. 32. SDS-PAGE analysis of Cpn10-binding molecules. SDS-PAGE gel of cell lysate proteins bound to and eluted from Cpn10 affinity column.

Figure 33:
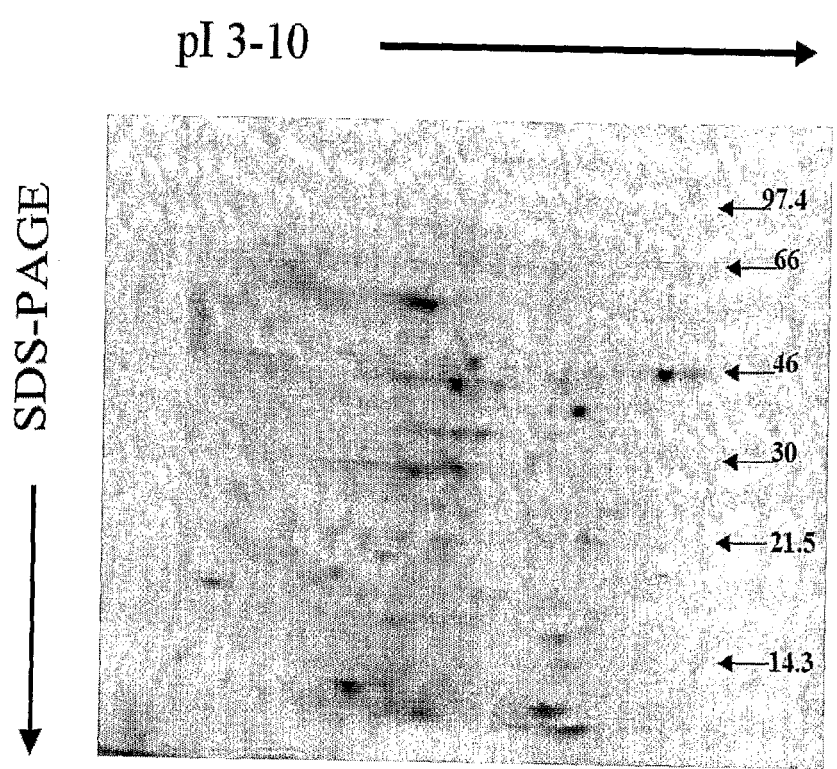

FIG. 33. 2D gel electrophoresis of Cpn10-binding molecules. 2D gel of cell lysate proteins bound to and eluted from CPn10 affinity column.

Figure 34:
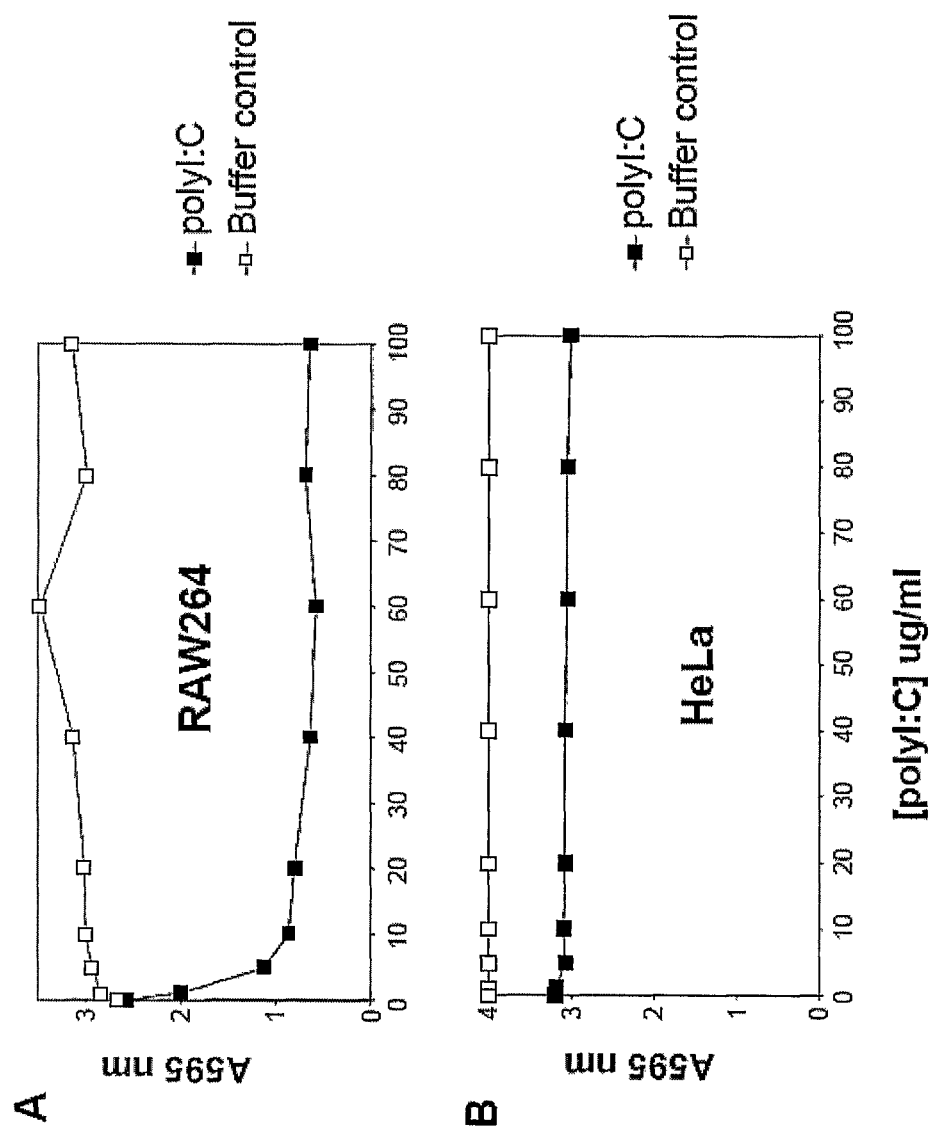

FIG. 34. Toxicity profile of PolyI:C in RAW264 (A) and HeLa cells (B) over 3 days.

Figure 35:
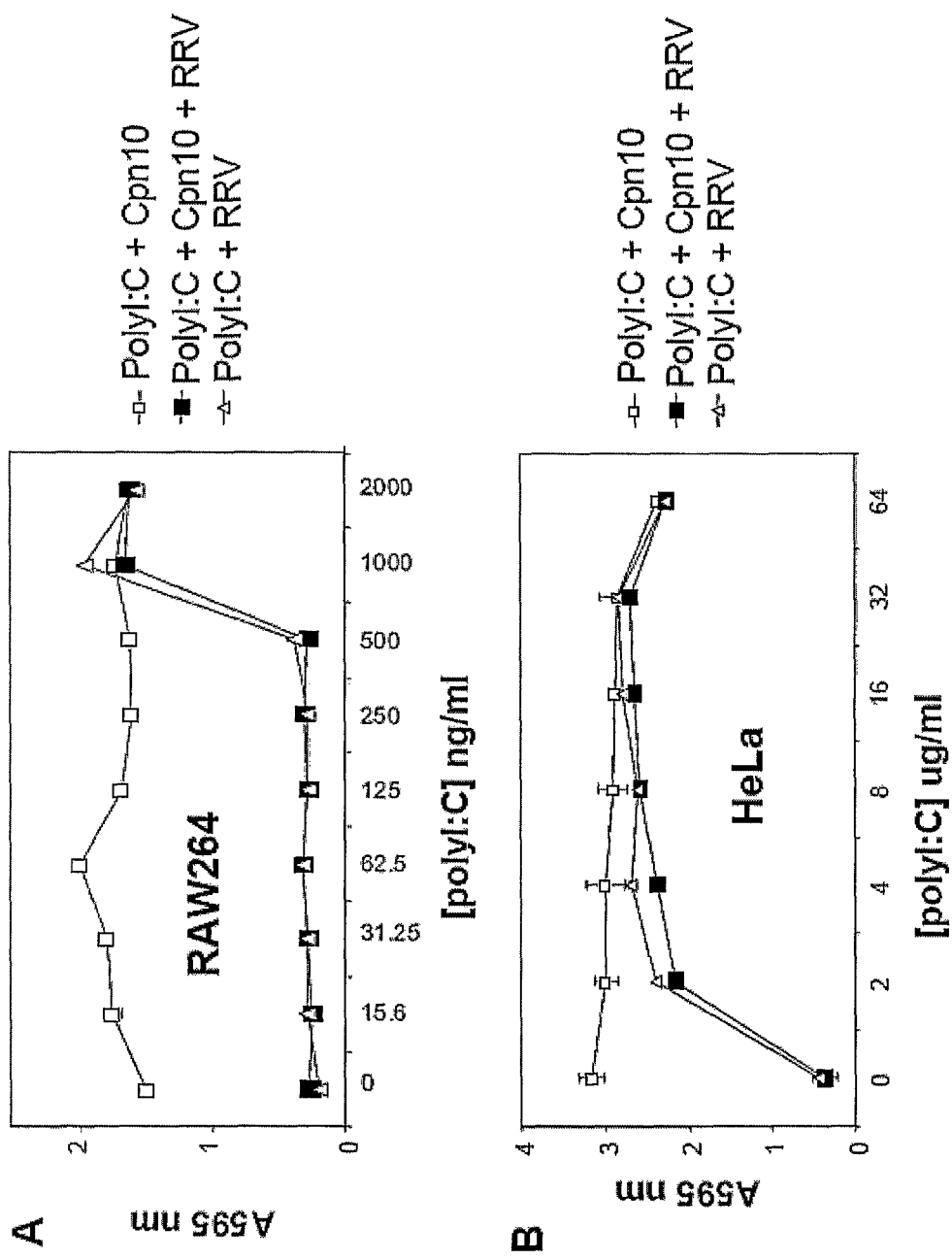

FIG. 35. Influence of Cpn10 on PolyI:C in RAW264 (A) and HeLa cells (B) over 3 days.

FIG. 36. Cpn10 interacts with human antigen presenting cells at the cell surface, and is internalized into endolysosomal compartments. Purified PBMC were incubated with fluorophore-conjugated Cpn10 for 10 min at 4° C. and surface fluorescence measured by flow cytometry (A). Cpn10 associated most strongly with mDC and pDC, and monocytes showed increased binding of fluorescent Cpn10 following LTA stimulation over 4 h (B). RAW264.7 cells and purified human pDC were incubated with fluorescent Cpn10 for 30 min at 37° C. prior to confocal imaging. Co-incubation with fluorescent markers of mitochondrial and acidic compartments revealed Cpn10 internalization into endo-lysosomal compartments (C).

The amino acid sequence of wild-type human Cpn10 (GenBank Accession No. X75821) is provided in SEQ ID NO:1. The amino acid sequences of two modified forms of Cpn10, with additional amino acid residues at the N-terminal are provided in SEQ ID NOs:2 and 3. The nucleotide sequence encoding the same is provided in SEQ ID NO:4. Oligonucleotide primers used in the examples as disclosed herein are provided in SEQ ID NOs:5-10.

BEST MODE OF PERFORMING THE INVENTION

Cpn10 has previously been shown to reduce the production of pro-inflammatory cytokines such as TNF-α and RANTES both in cell cultures and in vivo (see for example Johnson et al., 2005, *J Biol Chem* 280:4037-4047 and International Patent Application No. PCT/AU2005/000041, WO2005/067959, the disclosure of which is incorporated herein by reference). These findings support the use of Cpn10 as a therapeutic agent for the treatment of a variety of inflammatory diseases including, for example, multiple sclerosis, rheumatoid arthritis and graft-versus-host disease.

Methods for Modulation of Toll-like Receptor Signaling and Immunomodulator Production As disclosed herein the inventors have now demonstrated that human Cpn10, when administered with the TLR3 agonist polyI:C, results in a marked synergistic increase in the production of IFNβ and IFNα. Further, Cpn10 is demonstrated to modulate signaling via TLR7 and TLR9 as measured by reductions in NF-κB activation.

Moreover, the inventors have surprisingly shown that Cpn10, but not Cpn60 or GroES, associates with TLR4 at the cell surface following stimulation with LPS in the form of an "activation cluster". The inventors have further shown that Cpn10 associates with TLR2 following stimulation with liopteichoic acid (LTA), with TLR7 following stimulation with viral single-stranded RNA and/or imiquimod, and with TLR9 following stimulation with CpG DNA. In each case, such association is in the form of Cpn10 interacting with an "activation cluster" comprising a particular TLR and its agonist.

Accordingly, the present invention provides methods for modulating Toll-like receptor signalling in a subject, or in at least one cell, tissue or organ thereof, wherein said methods comprise administering an effective amount of chaperonin 10, wherein Toll-like receptor signalling involves association of the chaperonin 10 with a Toll-like receptor in an activation cluster.

Toll-like receptor signalling may also be modulated by administering an effective amount of at least one antagonist of chaperonin 10, wherein Toll-like receptor signalling involves association of the chaperonin 10 with a Toll-like receptor in an activation cluster, and wherein the antagonist prevents chaperonin 10 associating with a Toll-like receptor in an activation cluster, and/or prevents signalling by the activation cluster.

The activation cluster may be located on the surface of a cell or on the surface of a cellular vesicle such as an endosome. The activation cluster may comprise chaperonin 10, a Toll-like receptor, and optionally, at least one other molecule. The at least one other molecule may comprise a Toll-like receptor agonist.

In one embodiment, the activation cluster comprises chaperonin 10, TLR2 and lipoteichoic acid (LTA). In an additional embodiment, the activation cluster comprises chaperonin 10, TLR3 and double-stranded RNA. In another embodiment, the activation cluster comprises chaperonin 10, TLR4 and LPS. In a further embodiment, the activation cluster comprises chaperonin 10, TLR7 and single-stranded RNA. In a still further embodiment, the activation cluster comprises chaperonin 10, TLR9 and DNA comprising a CpG motif.

The chaperonin 10 may be a naturally-derived, recombinantly produced or synthetically produced chaperonin 10. The chaperonin 10 may be of eukaryotic origin. The chaperonin 10 may be human chaperonin 10. The chaperonin 10 may comprise the polypeptide sequence as set forth in SEQ ID NO:1, SEQ ID NO:2 or SEQ ID NO:3. The chaperonin 10 may be acetylated or non-acetylated, and may or may not comprise a single or multiple N-terminal extension. The chaperonin 10 may be administered in the form of a polynucleotide encoding chaperonin 10. The polynucleotide encoding chaperonin 10 may be located in a genetic construct, operably linked to a promoter. The polynucleotide may comprise the sequence as set forth in SEQ ID NO:4.

The method may further comprise the administration of at least one additional agent. The agent may be an immunomodulator. The immunomodulator may be, for example, TNF-α, IL-1β, IL-6, IL-10, IL-12 or a type I interferon. The type I interferon may be IFNα or IFNβ.

Typically, the modulatory activity of Cpn10 is exhibited through initial exposure of TLRs to Cpn10, and then the addition of one or more TLR agonists, as demonstrated by the inventors and disclosed herein, for example, in relation to immunomodulatory assays involving RAW264.7 cells. The agonist may be a bacterial, fungal, yeast or viral pathogen, a molecule or component derived therefrom or produced thereby or a synthetic compound. The TLR agonist may also be a product from damaged human cells associated with autoimmune diseases, as exemplified by TLR9 having as an agonist human DNA. Non-limiting examples of TLR3 agonists include double-stranded RNA and polyI:C. Non-limiting examples of TLR7 agonists include single-stranded RNA, imidazoquinolines such as resiquimod and imiquimod and small molecule agonists such as isatoribine. Non-limiting examples of TLR9 agonists include DNA containing unmethylated CpG-rich motifs and synthetic CpG-comprising oligonucleotides. However those skilled in the art will readily appreciate that the present invention is not limited by the identity of the TLR agonists.

The present invention also provides methods for modulating the production and/or secretion of one or more immunomodulators in a subject, or at least one cell, tissue or organ thereof, wherein said methods comprise administering an effective amount of chaperonin 10, wherein the chaperonin 10 associates with a Toll-like receptor in an activation cluster, and wherein formation of the activation cluster is associated with modulation of the production and/or secretion of the one or more immunomodulators.

Modulation of the production and/or secretion of one or more immunomodulators may also be achieved by administering an effective amount of an antagonist of chaperonin 10, wherein the antagonist prevents chaperonin 10 associating with a Toll-like receptor in an activation cluster, and/or prevents signalling by the activation cluster, and wherein formation of the activation cluster is associated with modulation of the production and/or secretion of the one or more immunomodulators.

The immunomodulator may be, for example, TNF-α, IL-1β, IL-6, IL-10, IL-12 or a type I interferon. The type I interferon may be IFNα or IFNβ.

Methods for Treating or Preventing a Disease

The inventors' findings as presented herein support the use of Cpn10 in the clinical management of a variety of diseases and conditions, including acute and chronic viral and bacterial diseases. Accordingly the present invention provides methods for the treatment or prevention of viral and bacterial diseases and disorders caused by or otherwise associated with viral or bacterial infections, comprising the administration of Cpn10.

Additionally, stimulation of TLR3, TLR7 and/or TLR9 is implicated in natural responses to and/or in therapeutic treatment of a variety of other disorders including asthma, allergy, inflammatory bowel disease and general inflammation. Thus the present invention also contemplates methods for the treatment or prevention of such diseases and disorders comprising the administration of Cpn10.

Accordingly, the present invention provides methods for treating or preventing a disease or condition in a subject, wherein said methods comprise administering to the subject an effective amount of chaperonin 10, wherein the chaperonin 10 associates with a Toll-like receptor in an activation cluster, and wherein formation of the activation cluster is associated with initiation, enhancement and/or maintenance of an immune response to the disease or condition.

Said methods may also comprise administering to the subject an effective amount of at least one antagonist of chaperonin 10, wherein the antagonist prevents chaperonin 10 associating with a Toll-like receptor in an activation cluster, and/or prevents signalling by the activation cluster, and wherein formation of the activation cluster is associated with establishment and/or progression of the disease or condition.

The disease or condition may include, but is not limited to, the group comprising viral, fungal, yeast or bacterial infections, acute or chronic inflammatory diseases including septic shock, inflammatory bowel disease, arthritis, psoriasis, heart disease, atherosclerosis, chronic pulmonary disease, cachexia, multiple sclerosis, GVHD and cancer. Any disease or condition, the establishment and/or progression of which, or the initiation, enhancement and/or maintenance of an immune response against which, involves the association of chaperonin 10 with a Toll-like receptor in an activation cluster, is contemplated as within the scope of the present invention.

In one embodiment, the chaperonin 10 regulates LTA-induced TLR2 signalling. The chaperonin 10 may modulate TLR2-induced immunomodulator production and/or secretion. In an additional embodiment, the chaperonin 10 regulates double-stranded RNA-induced TLR3 signalling. The chaperonin 10 may modulate TLR3-induced immunomodulator production and/or secretion. In another embodiment, the chaperonin 10 regulates LPS-induced TLR4 signalling. The chaperonin 10 may modulate TLR4-induced immunomodulator production and/or secretion. In a further embodiment, the chaperonin 10 regulates viral single-stranded RNA-induced TLR7 signalling. The chaperonin 10 may modulate TLR7-induced immunomodulator production and/or secretion. In a still further embodiment, the chaperonin 10 regulates CpG motif-induced TLR9 signalling. The chaperonin 10 may modulate TLR9-induced immunomodulator production and/or secretion.

Compositions and Uses Thereof

The present invention provides compositions when used for the treatment or prevention of a disease or condition, the compositions comprising chaperonin 10 together with at least one pharmaceutically acceptable carrier, diluent or adjuvant, wherein the chaperonin 10 associates with a Toll-like receptor in an activation cluster, and wherein formation of the activation cluster is associated with initiation, enhancement and/or maintenance of an immune response to the disease or condition.

The compositions may further comprise at least one agonist of a Toll-like receptor. The composition may further comprise at least one immunomodulator such as a type I interferon.

Other compositions used for the treatment or prevention of a disease or condition, the composition comprise at least one antagonist of chaperonin 10, wherein the antagonist prevents chaperonin 10 associating with a Toll-like receptor in an activation cluster, and/or prevents signalling by the activation cluster, and wherein formation of the activation cluster is associated with establishment and/or progression of the disease or condition.

Uses of chaperonin 10 for the manufacture of a medicament for the treatment or prevention of a disease or condition are also contemplated, wherein the chaperonin 10 associates with a Toll-like receptor in an activation cluster, and wherein formation of the activation cluster is associated with initiation, enhancement and/or maintenance of an immune response to the disease or condition.

Uses of antagonists of chaperonin 10 for the manufacture of a medicament for the treatment or prevention of a disease or condition are also contemplated, wherein the antagonist prevents chaperonin 10 associating with a Toll-like receptor in an activation cluster, and/or prevents signalling by the activation cluster, and wherein formation of the activation cluster is associated with establishment and/or progression of the disease or condition.

In general, suitable compositions for use in accordance with the methods of the present invention may be prepared according to methods and procedures that are known to those of ordinary skill in the art and accordingly may include a pharmaceutically acceptable carrier, diluent and/or adjuvant.

Combination Therapies

Those skilled in the art will appreciate that in accordance with the methods of the present invention Cpn10 may be administered alone or in conjunction with one or more additional agents. For example, Cpn10 may be administered together with one or more TLR agonists capable of stimulating one or more of TLR2, TLR3, TLR4, TLR7 and TLR9. Additionally, the present invention contemplates combination therapy using Cpn10 in conjunction with other therapeutic approaches to the treatment of diseases and disorders. For example, Cpn10 may be useful in the treatment of viral diseases which are responsive to therapy with Type I interferons such as IFNβ or IFNα. Further, as agonist-induced activation of TLR7 and TLR9 has previously been reported to enhance the response of tumours to radiation therapy, Cpn10 may be used in conjunction with radiation therapy for the treatment of cancer.

For such combination therapies, each component of the combination therapy may be administered at the same time, or sequentially in any order, or at different times, so as to provide the desired effect. Alternatively, the components may be formulated together in a single dosage unit as a combination product. When administered separately, it may be preferred for the components to be administered by the same route of administration, although it is not necessary for this to be so.

Cpn10

In accordance with aspects and embodiments of the present invention, a subject in need of treatment is administered with an effective amount of Cpn10. In particular embodiments the subject to be treated is a human, and accordingly, the Cpn10 polypeptide is the human Cpn10 polypeptide. Those skilled in the art will appreciate that the precise identity of the Cpn10 used in accordance with the present invention may vary depending on a number of factors, for example the species to be treated, such that the Cpn10 may be selected so as to be derived from the species to be treated.

Typically, the Cpn10 is recombinant Cpn10. Methods described in Morton et al., 2000 (*Immunol Cell Biol* 78:603-607), Ryan et al., 1995 (*J Biol Chem* 270:22037-22043) and Johnson et al., 2005 (*J Biol Chem* 280:4037-4047) are examples of suitable production methods for recombinant Cpn10 protein, although the skilled addressee will appreciate that the present invention is not limited by the method of purification or production used and any other method may be used to produce Cpn10 for use in accordance with the methods and compositions of the present invention.

Cpn10 polypeptides and peptide fragments for use in accordance with the present invention may be obtained using of standard recombinant nucleic acid techniques or may be synthesized, for example using conventional liquid or solid phase synthesis techniques. Cpn10 peptides may be produced by digestion of a polypeptide with one or more proteinases such as endoLys-C, endoArg-C, endoGlu-C and *staphylococcus* V8-protease. The digested peptide fragments can be purified by, for example, high performance liquid chromatographic (HPLC) techniques.

Embodiments of the invention also contemplate the administration of a polynucleotide encoding Cpn10. In such situations the polynucleotide is typically operably linked to a promoter such that the appropriate polypeptide sequence is produced following administration of the polynucleotide to the subject. The polynucleotide may be administered to subjects in a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences. The nucleic acid construct to be administered may comprise naked DNA or may be in the form of a composition, together with one or more pharmaceutically acceptable carriers.

The Cpn10 polypeptide may have, but is not limited to, the amino acid sequence as set forth in SEQ ID NO:1. The nucleotide sequence of the polynucleotide encoding Cpn10 may be as set forth in SEQ ID NO:4 or display sufficient sequence identity thereto to hybridise to the sequence of SEQ ID NO:4. In alternative embodiments, the nucleotide sequence of the polynucleotide may share at least 30%, 40%, 50%, 60%, 70%, 80%, 85%, 90%, 96%, 97%, 98% or 99% identity with the sequence set forth in SEQ ID NO:4.

Within the scope of the terms "polypeptide" and "polynucleotide" as used herein are fragments and variants thereof. By way of example only, peptide fragments of Cpn10 as described in WO 95/15338 may be used in accordance with aspects and embodiments of the present invention.

The term "fragment" refers to a nucleic acid or polypeptide sequence that encodes a constituent or is a constituent of full-length Cpn10 protein. In terms of the polypeptide the fragment possesses qualitative biological activity in common with the full-length protein. A biologically active fragment of Cpn10 used in accordance with the present invention may typically possess at least about 50% of the immunomodulatory activity of the corresponding full length protein, more typically at least about 60% of such activity, more typically at least about 70% of such activity, more typically at least about 80% of such activity, more typically at least about 90% of such activity, and more typically at least about 95% of such activity.

The term "variant" as used herein refers to substantially similar molecules. Generally, nucleic acid sequence variants encode polypeptides which possess qualitative biological activity in common. Generally, polypeptide sequence variants also possess qualitative biological activity in common. Further, these polypeptide sequence variants may share at least 50%, 55%, 60%, 65%, 70%, 75%, 80%, 85%, 90%, 95%, 96%, 97%, 98% or 99% sequence identity.

Further, a variant polypeptide may include analogues, wherein the term "analogue" means a polypeptide which is a derivative of Cpn10, which derivative comprises addition, deletion, substitution of one or more amino acids, such that the polypeptide retains substantially the same function as native Cpn10. It is well known in the art that some amino acids may be changed within a polypeptide without altering the activity of the polypeptide (conservative substitutions). The term "conservative amino acid substitution" refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution. Amino acid additions may result from the fusion of a Cpn10 polypeptide or fragment thereof with a second polypeptide or peptide, such as a polyhistidine tag, maltose binding protein fusion, glutathione S transferase fusion, green fluorescent protein fusion, or the addition of an epitope tag such as FLAG or c-myc. For example, the wild-type human Cpn10 polypeptide may comprise an additional GSM tripeptide moiety at the N-terminus (SEQ ID NO:2; see for example WO 95/15338, the disclosure of which is incorporated herein by reference) or an additional alanine (A) reside at the N-terminus (SEQ ID NO:3; WO 2004/041300, the disclosure of which is incorporated herein by reference). Other mutated forms of Cpn10 include those disclosed in Australian provisional patent application No. 2005904765, the disclosure of which is incorporated herein by reference. The present invention also contemplates the use of polynucleotides encoding such modified forms of Cpn10.

Cpn10 variants can be generated by mutagenesis of a Cpn10 protein or mutagenesis of an encoding nucleic acid, such as by random mutagenesis or site-directed mutagenesis using methods well known to those skilled in the art. Such methods may be found, for example in *Current Protocols In Molecular Biology* (Chapter 9), Ausubel et al., 1994, John Wiley & Sons, Inc., New York, the disclosure of which is incorporated herein by reference. Variants and analogues also encompass polypeptides complexed with other chemical moieties, fusion proteins or otherwise post-transitionally modified. Examples of suitable modifications are described in co-pending International Patent Application No. PCT/AU2005/000041; WO2005/067959, the disclosure of which is incorporated herein by reference.

Further, the Cpn10 polypeptide or fragment thereof may possess other post-translational modifications, including side-chain modifications such as for example acetylation, amidination, carbamoylation, reductive alkylation and other modifications as are known to those skilled in the art.

A Cpn10 polynucleotide may further comprise, but is not limited to, any polynucleotide that hybridizes to a Cpn10 polynucleotide as defined herein under conditions of high stringency. The term "high stringency" as used herein refers to the conditions under which two polynucleotides may be hybridized, and may include, for example, the concentration of salts and/or detergents in a solution, the temperature of a solution that is used during the hybridization of the two polynucleotides and time period of the hybridization. Accordingly, the term "high stringency" as used herein refers to conditions in a solution that are conducive to hybridization of two polynucleotides only where such polynucleotides share a high degree of homology. The degree of homology may include, but not be limited to, a range of from about 50% to 99%. Thus, "high stringency" conditions may involve, but are not limited to, the use of a wash buffer that comprises 0 to 10% sodium dodecyl sulfate and/or 0 to 1× sodium chloride-sodium citrate at a temperature in the range of from about 60° C. to 70° C., or any other combination of buffers, temperature or time period which would yield a "high stringency" solution for hybridization.

Routes of Administration

Compositions may be administered by standard routes. In general, the compositions may be administered by the parenteral (e.g., intravenous, intraspinal, subcutaneous or intramuscular), oral or topical route. Administration may be systemic, regional or local. The particular route of administration to be used in any given circumstance will depend on a number of factors, including the nature of the condition to be treated, the severity and extent of the condition, the required dosage of the particular compound to be delivered and the potential side-effects of the compound.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Diluents, Carriers, Adjuvants and Excipients

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable carriers or diluents include, but are not limited to, demineralised or distilled water, saline solution, vegetable based oils such as peanut oil, safflower oil, olive oil, cottonseed oil, maize oil, sesame oils, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Some examples of suitable carriers, diluents, excipients and adjuvants for oral use include, but are not limited to, peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include, but are not limited to, emollients, emulsifiers, thickening agents, preservatives, bactericides and buffering agents.

Solid forms for oral administration may contain, but are not limited to, binders acceptable in human and veterinary pharmaceutical practice, sweeteners, disintegrating agents, diluents, flavourings, coating agents, preservatives, lubricants and/or time delay agents. Suitable binders include, but are not limited to, gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include, but are not limited to, corn starch, methylcellulose, polyvinylpyrrolidone, guar gum, xanthan gum, bentonite, alginic acid or agar. Suitable diluents include, but are not limited to, lactose, sorbitol, mannitol, dextrose, kaolin, cellulose, calcium carbonate, calcium silicate or dicalcium phosphate. Suitable flavouring agents include, but are not limited to, peppermint oil, oil of wintergreen, cherry, orange or raspberry flavouring. Suitable coating agents include, but are not limited to, polymers or copolymers of acrylic acid and/or methacrylic acid and/or their esters, waxes, fatty alcohols, zein, shellac or gluten. Suitable preservatives include, but are not limited to, sodium benzoate, vitamin E, alpha-tocopherol, ascorbic acid, methyl paraben, propyl paraben or sodium bisulphite. Suitable lubricants include, but are not limited to, magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include, but are not limited to, water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include, but are not limited to, sodium carboxymethylcellulose, methylcellulose, hydroxypropylmethyl-cellulose, poly-vinyl-pyrrolidone, sodium alginate or acetyl alcohol. Suitable dispersing agents include, but are not limited to, lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include, but are not limited to, dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The topical formulations of the present invention, comprise an active ingredient together with one or more acceptable carriers, and optionally any other therapeutic ingredients. Formulations suitable for topical administration include, but are not limited to, liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include, but are not limited to, glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include, but are not limited to, an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

The compositions may be conjugated to an array of polyethylene glycol (PEG) derivatives. The addition of PEG to proteins (PEGylation) is a well established method for decreasing the plasma clearance rates of proteins, thereby increasing their efficacy (Nucci et al., 1991, *Adv. Drug Del. Rev.* 6:133). Additional benefits of PEGylation may include, greater stability of proteins, decreased immunogenicity, enhanced solubility and decreased susceptibility to proteolysis (Sheffield W. 2001, *Curr Drug Targets Cardiovasc Haematol Disord.* 1:1-22). PEG molecules contain the basic repeating structure of —$(OCH_3CH_2)$n-OH and are classified into groups according to their molecular weight. PEG derivatives are conjugated to proteins to increase their hydrodynamic radius and in general, their increase in half-life is directly related to the size of the PEG chain attached (Sheffield W. 2001, *Curr Drug Targets Cardiovasc Haematol Disord.* 1:1-22).

The compositions may also be administered in the form of microparticles. Biodegradable microparticles formed from polylactide (PLA), polylactide-co-glycolide (PLGA), and epsilon-caprolactone (ε-caprolactone) have been extensively used as drug carriers to increase plasma half life and thereby prolong efficacy (R. Kumar, M., 2000, *J Pharm Pharmaceut Sci.* 3(2) 234-258). Microparticles have been formulated for the delivery of a range of drug candidates including vaccines, antibiotics, and DNA. Moreover, these formulations have been developed for various delivery routes including parenteral subcutaneous injection, intravenous injection and inhalation.

The compositions may incorporate a controlled release matrix that is composed of sucrose acetate isobutyrate (SAIB) and organic solvent or organic solvents mixture. Polymer additives may be added to the vehicle as a release modifier to further increase the viscosity and slow down the release rate. SAIB is a well known food additive. It is a very hydrophobic, fully esterified sucrose derivative, at a nominal ratio of six isobutyrate to two acetate groups. As a mixed ester, SAIB does not crystallize but exists as a clear viscous liquid. Mixing SAIB with a pharmaceutically accepted organic solvent such as ethanol or benzyl alcohol decreases the viscosity of the mixture sufficiently to allow for injection. An active pharmaceutical ingredient may be added to the SAIB delivery vehicle to form SAIB solution or suspension formulations. When the formulation is injected subcutaneously, the solvent diffuses from the matrix allowing the SAIB-drug or SAIB-drug-polymer mixtures to set up as an in situ forming depot.

For the purposes of the present invention molecules and agents may be administered to subjects as compositions either therapeutically or preventively. In a therapeutic application, compositions are administered to a patient already suffering from a disease, in an amount sufficient to cure or at least partially arrest the disease and its complications. The composition should provide a quantity of the molecule or agent sufficient to effectively treat the patient.

Dosages

The therapeutically effective dose level for any particular patient will depend upon a variety of factors including: the disorder being treated and the severity of the disorder; activity of the molecule or agent employed; the composition employed; the age, body weight, general health, sex and diet of the patient; the time of administration; the route of administration; the rate of sequestration of the molecule or agent; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

Typically, in therapeutic applications, the treatment would be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

Cpn10 Agonists and Antagonists

The present invention also contemplates the use of agonists and antagonists of Cpn10 and methods of screening and producing such agonists and antagonists.

Cpn10 agonists and antagonists may be specifically designed or screened according to their effect upon Toll-like receptor signalling and immunomodulator secretion.

Antibodies may act as agonists or antagonists of Cpn10, or fragments or analogues thereof. Preferably suitable antibodies are prepared from discrete regions or fragments of the Cpn10 polypeptide, in particular those involved in conferring protease activity and/or partner or substrate binding. An antigenic Cpn10 polypeptide contains at least about 5, and preferably at least about 10, amino acids.

Methods for the generation of suitable antibodies will be readily appreciated by those skilled in the art. For example, an anti-Cpn10 monoclonal antibody, typically containing Fab portions, may be prepared using the hybridoma technology described in Antibodies-A Laboratory Manual, Harlow and Lane, eds., Cold Spring Harbor Laboratory, N.Y. (1988).

In essence, in the preparation of monoclonal antibodies directed toward Cpn10, or fragment or analogue thereof, any technique that provides for the production of antibody molecules by continuous cell lines in culture may be used. These include the hybridoma technique originally developed by Kohler et al., 1975, *Nature*, 256:495-497, as well as the trioma technique, the human B-cell hybridoma technique (Kozbor et al., 1983, *Immunology Today*, 4:72), and the EBV-hybridoma technique to produce human monoclonal antibodies (Cole et al., in *Monoclonal Antibodies and Cancer Therapy*, pp. 77-96, Alan R. Liss, Inc., (1985)). Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980).

In summary, a means of producing a hybridoma from which the monoclonal antibody is produced, a myeloma or other self-perpetuating cell line is fused with lymphocytes obtained from the spleen of a mammal hyperimmunised with a recognition factor-binding portion thereof, or recognition factor, or an origin-specific DNA-binding portion thereof. Hybridomas producing a monoclonal antibody useful in practicing this invention are identified by their ability to immunoreact with the present recognition factor and their ability to inhibit specified transcriptional activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Similarly, there are various procedures known in the art which may be used for the production of polyclonal antibodies. For the production of anti-Cpn10 polyclonal antibody, various host animals can be immunized by injection with Cpn10, or a fragment or analogue thereof, including but not limited to horses, cows, rabbits, chickens, mice, rats, sheep, goats, etc. Further, the Cpn10 polypeptide or fragment or analogue thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), mineral gels such as aluminium hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, Current Protocols in Molecular Biology, Vol. 1, John Wiley & Sons, Inc., New York). Antibody binding may be detected by virtue of a detectable label on the primary antibody. Alternatively, the antibody may be detected by virtue of its binding with a secondary antibody or reagent which is appropriately labelled. A variety of methods are known in the art for detecting binding in an immunoassay and are within the scope of the present invention.

The antibody (or fragment thereof) raised against Cpn10 or a fragment or analogue thereof has binding affinity for Cpn10. Preferably, the antibody (or fragment thereof) has binding affinity or avidity greater than about $10^5$ $M^{-1}$, more preferably greater than about $10^6$ $M^{-1}$, more preferably still greater than about $10^7$ $M^{-1}$ and most preferably greater than about $10^8$ $M^{-1}$.

In terms of obtaining a suitable amount of an antibody according to the present invention, one may manufacture the antibody(s) using batch fermentation with serum free medium. After fermentation the antibody may be purified via a multistep procedure incorporating chromatography and viral inactivation/removal steps. For instance, the antibody may be first separated by Protein A affinity chromatography and then treated with solvent/detergent to inactivate any lipid enveloped viruses. Further purification, typically by anion and cation exchange chromatography may be used to remove residual proteins, solvents/detergents and nucleic acids. The purified antibody may be further purified and formulated into 0.9% saline using gel filtration columns. The formulated bulk preparation may then be sterilised and viral filtered and dispensed.

Agonists and antagonists other than antibodies are also contemplated. A candidate agonist or antagonist may be identified by an ability to form a molecular complex with a Toll-like receptor, and optionally a Toll-like receptor agonist. Further, a candidate antagonist may be identified by an ability to prevent or disrupt formation of a molecular complex comprising Cpn10, and a Toll-like receptor or a Toll-like receptor agonist.

Techniques and procedures for identifying and producing agonists and antagonists are well known to those skilled in the art, including screening of libraries of molecules such as synthetic chemical libraries such as combinatorial libraries, computer assisted screening of structural databases, computer-assisted modelling and/or design, or more traditional biophysical techniques which detect molecular binding interactions.

The present invention will now be further described in greater detail by reference to the following specific examples, which should not be construed as in any way limiting the scope of the invention.

EXAMPLES

Recombinant Human Cpn10

For the experiments described in Examples 1 to 4 below, recombinant human Cpn10 (GenBank Accession No. X75821) was produced in *E. coli* with an N-terminal Alanine residue as described in Johnson et al., 2005 (*J Biol Chem* 280:4037-4047). Purity was determined to be >97% by SDS-PAGE. Frozen aliquots of Cpn10 were thawed only once prior to use. All Cpn10 batches showed the same molar activity as *E. coli* GroES in GroEL-mediated rhodanese refolding assays (data not shown).

Example 1

Production of the Antiviral Cytokine IFNβ in the Presence of PolyI:C

Experiments were carried out to determine the effect of Cpn10 on the production of the antiviral cytokine interferon-β (IFNβ), when administered in combination with the selective agonist of TLR3, polyI:C (polyinosinic-polysytidilic acid).

Experiments were conducted in the murine macrophage cell line RAW264.7 (ATCC Accession No TIB71) as described in Johnson et al., 2005 (*J Biol Chem* 280:4037-4047). Briefly, RAW264.7 cells were seeded at $2\times10^5$ cells/well in 24 well plates and cultured overnight (37° C., 5% $CO_2$). Recombinant human Cpn10 (at concentrations between 10 μg/ml and 200 μg/ml) or buffer was added to cells in duplicate for 2 hours followed by the addition of polyI:C (tlrl-pic, InvivoGen, San Diego, Calif.) to a final concentration of 100 μg/ml. After 24 hours, supernatants were collected and analysed for IFNβ levels using a specific ELISA according to manufacturer's instructions (Cat No. 42400-1, R&D Systems Inc, Minneapolis, Minn.).

Figure 1:
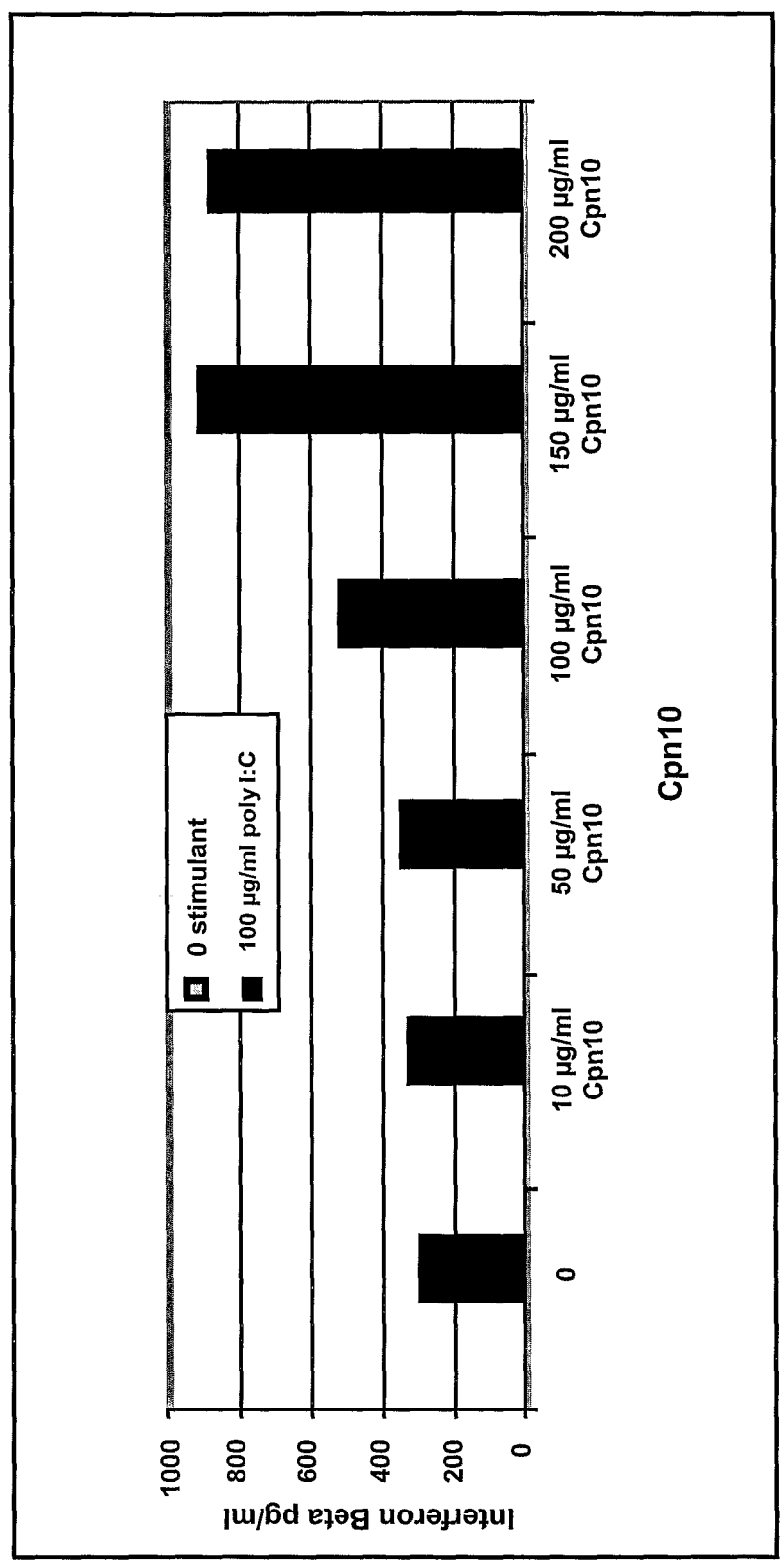
FIG. 1. Secretion of IFNβ (pg/ml) into supernatant of RAW264.7 cells following stimulation with 100 µg/ml polyI:C for 23 hours and in the presence of 10-200 µg/ml recombinant human Cpn 0, added 2 hours pre-stimulation. Results shown are from duplicate experiments.

As shown in FIG. 1, unstimulated RAW264.7 cells released no detectable IFNβ into the culture supernatants. Stimulation with polyI:C at 100 μg/ml resulted in 292 pg/ml of IFNβ being released into the RAW264.7 culture supernatants in the absence of Cpn10. Addition of increasing doses of Cpn10 from 10 μg/ml up to 200 μg/ml resulted in a dose-dependent increase in levels of IFNβ in the culture supernatants, reaching a maximum level of 900 pg/ml IFNβ at 150 μg/ml Cpn10.

Example 2

Anti-Viral Activity of RAW264.7 Cell Supernatants

The cell culture supernatants obtained from the experiments described in Example 1 above were frozen and stored at −20° C. prior to analysis for total anti-viral activity (total type I interferon release) in an L cell cytopathic effect reduction (CPER) assay.

Figure 2:
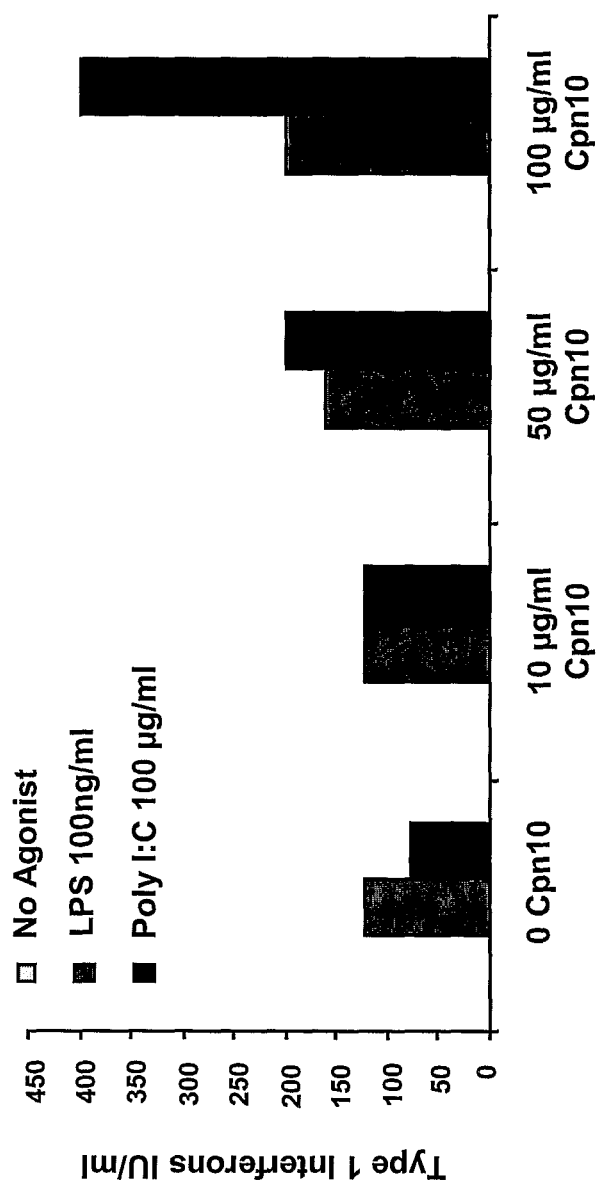
FIG. 2. Secretion of type I interferons (IU/ml) into supernatant of RAW264.7 cells following stimulation with either 100 ng/ml re-purified LPS or 100 µg/ml polyI:C in the presence of 10-100 µg/ml recombinant human Cpn10, added 2 hours pre-stimulation.

Briefly, $3\times10^4$ L cells were seeded into 96-well plates and left for 4 h at 37° C. to adhere. Duplicates of IFN standards and test supernatants were added to the plate in semi-log10 serial dilutions. The dilutions of standards were such to give a range of IFN activity from 1 to $10^4$ TU/ml. The plate was incubated overnight for 15 h, the medium was removed, and Semliki Forest virus was added to the wells at a titer 100 times that of the tissue culture $ID_{50}$. Plates were incubated for 3 days at 37° C. and then scored for cell viability. Every plate contained a duplicate row of cells without either IFN or test supernatant to serve as a control for maximal cell death. IFN titers were determined as the concentration of IFN to provide protection to 50% of the cells relative to National Institutes of Health standard Ga02901511. As illustrated in FIG. 2, the addition of Cpn10 resulted in a significant dose-responsive increase in the release of type I interferons (to a maximum at 100 μg/ml Cpn10) in the presence of polyI:C.

The data presented in Examples 1 and 2 indicate that administration of Cpn10 in the context of a viral infection where viral nucleic acids may be released, or when co-administered with a TLR3 agonist result in the stimulation of an enhanced level of anti-viral immunity.

Example 3

NF-κB Activation in HEK293 Cells Expressing TLR7

The ability of human Cpn10 to modulate signalling via the Toll-like receptor TLR7 was investigated in the human embryonic kidney cell line HE 93. Stable cell lines of HEK293 expressing both TLR7 and TLR4 were established as described in Latz et al, 2002 (*J Biol Chem* 277:47834-47843) and seeded into 96-well plates at a density of $2\times10^4$ cells per well. Following overnight growth, to enable determination of NF-κB activation, cells were transiently transfected with an NF-κB-luciferase reporter construct (as per Latz et al., 2002, *J Biol Chem* 277:47834-47843), comprising an artificial promoter composed of a multimer of 5 NF-κB sites driving expression of the firefly luciferase gene, together with the constitutively active Renilla luciferase reporter gene.

Following culture of the cells overnight, recombinant human Cpn10 was administered to the cells at a final concentration of 50 μg/ml either alone or simultaneously with one of the following: the TLR7 selective agonist Resiquimod R848, a phosphothioate CpG oligonucleotide (MWG Biotech) (TLR9 selective agonist), the TLR4 selective agonist lipopolysaccharide (LPS) or the protein kinase C activator phorbol 12-myristate 13-acetate (PMA), by way of a control.

NF-κB activation was then determined and quantified 5 h post-stimulation by measurement of luciferase activity using the Dual-Luciferase Assay Reporter System according to manufacturer's instructions (Promega, Madison Wis.) and a plate reader luminometer (Perkin Elmer).

Figure 3:
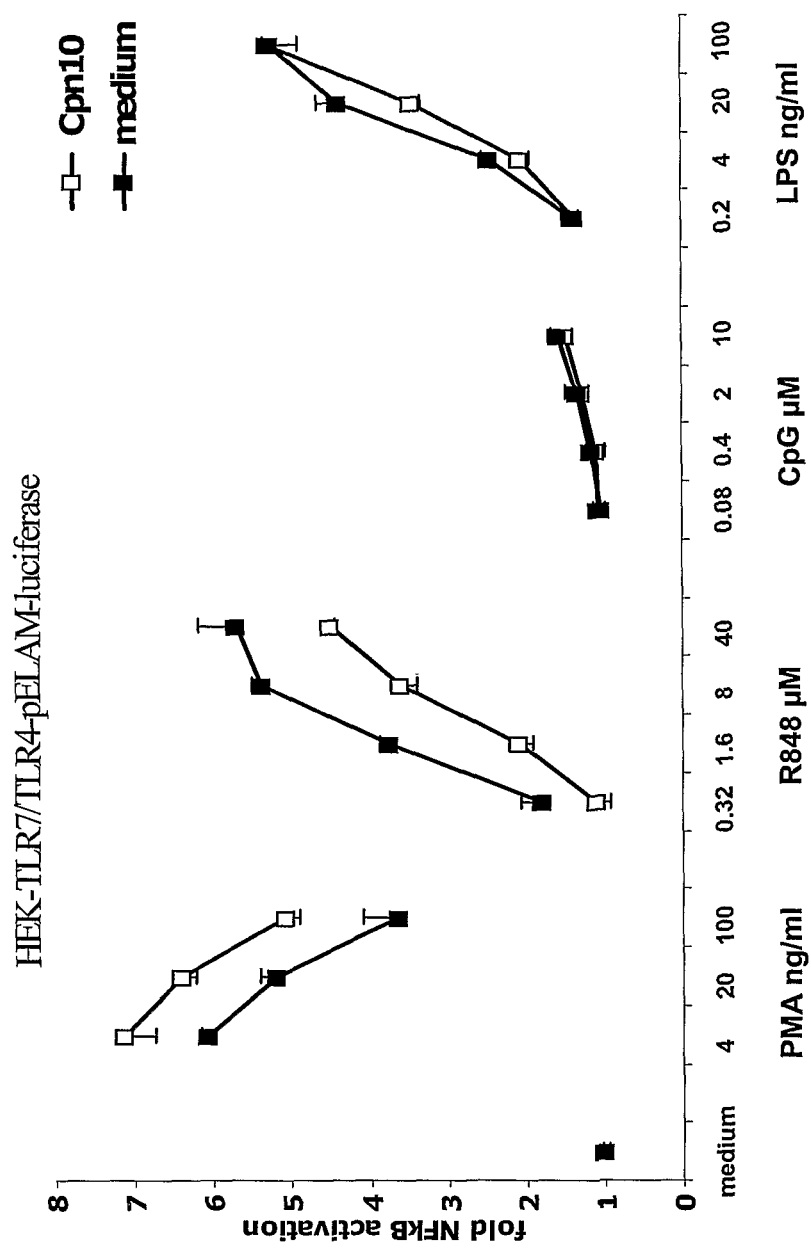
FIG. 3. NF-κB activation α-fold) in HEK293 cells following transfection with TLR7/TLR4-expressing construct and an NF-κB-luciferase reporter construct, in the presence (open squares) or absence (filled squares) of 50 µg/ml recombinant human Cpn10 (added simultaneously with agonist). Cells were stimulated with either phorbol 12-myristate 13-acetate (PMA; protein kinase C activator), R848 (R848; TLR7 agonist), CpG oligonucleotide (CpG; TLR9 agonist) or re-purified lipopolysaccharide (LPS; TLR4 agonist).

The results, expressed as fold NF-κB activation are shown in FIG. 3. In the absence of stimulation (medium alone) NF-κB activation was not induced. In contrast, the TLR7 selective agonist R848 at concentrations ranging from 0.32-40 μM induced more than 5-fold activation of NF-κB via TLR7. However in the presence of 50 μg/ml Cpn10, this activation was reduced by approximately 2-fold.

Example 4

NF-κB Activation in HEK293 Cells Expressing TLR9

The ability of human Cpn10 to modulate signalling via the Toll-like receptor TLR9 was also investigated in HEK293 cells. Assays were performed as described in Example 3.

Figure 4A:
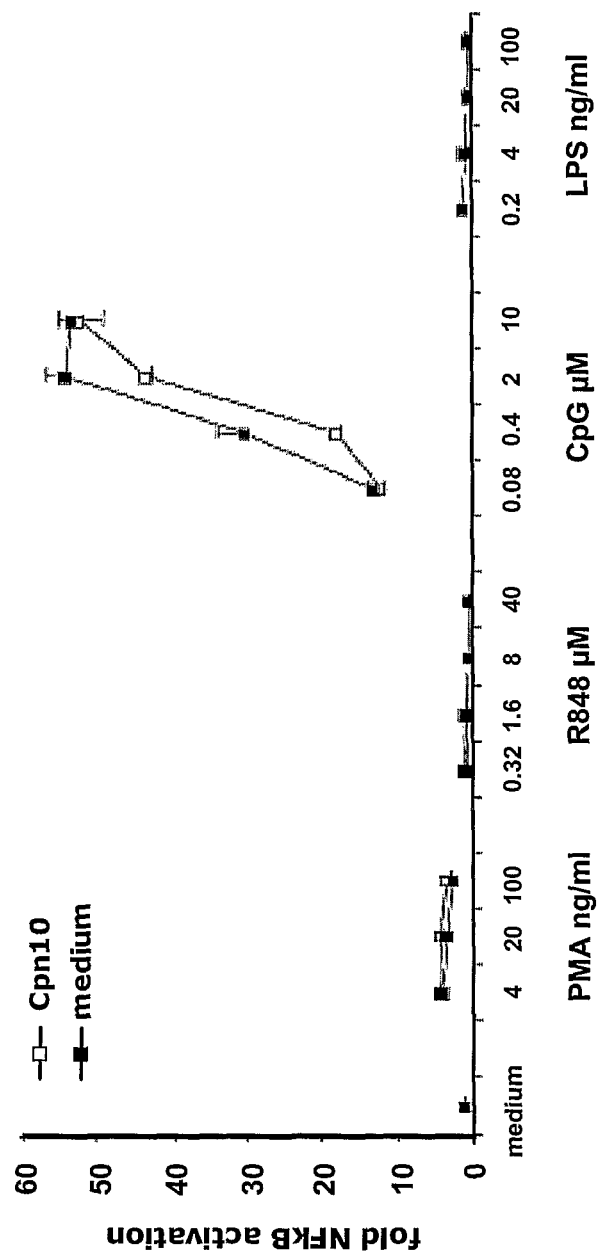
FIG. 4. NF-κB activation (x-fold) in HEK293 cells following transfection with TLR9-expressing construct and an NF-κB-luciferase reporter construct, in the presence (open squares) or absence (filled squares) of 50 µg/ml recombinant human Cpn10 (added simultaneously with agonist). Cells were stimulated with either phorbol 12-myristate 13-acetate (PMA; protein kinase C activator), R848 (R848; TLR7 agonist), CpG oligonucleotide (CpG; TLR9 agonist) or re-purified lipopolysaccharide (LPS; TLR4 agonist). Results for two independent clones are presented (A and B).
Figure 4B:
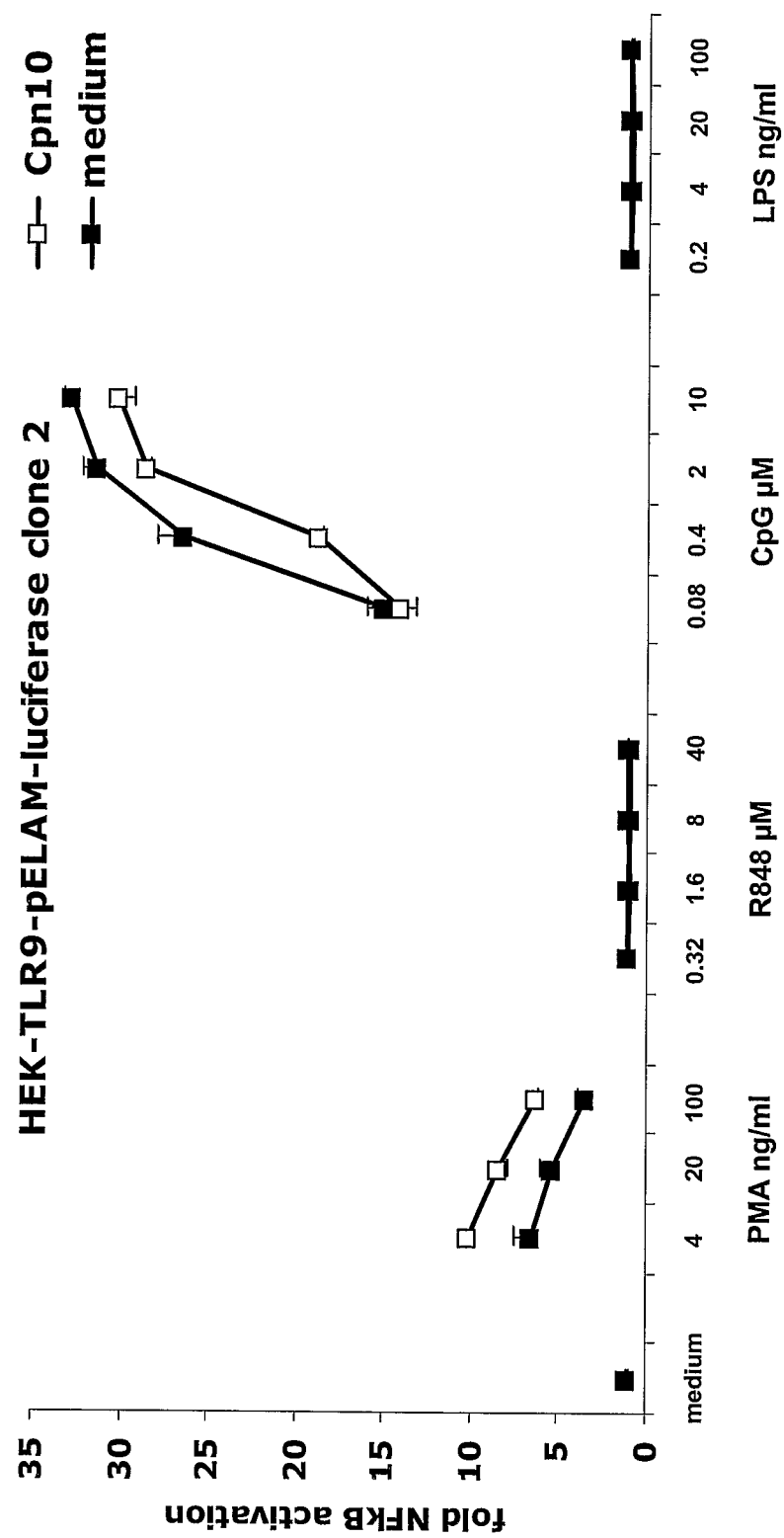

Assays were conducted on two independent clones of stably transfected HEK293 cells expressing TLR9. Results are shown in FIG. 4. In the absence of stimulation (medium alone) NF-κB activation was not induced. However activation of HEK-TLR9 with CpG DNA at concentrations ranging from 0.08-10 μM induced up to approximately 33-fold activation of NF-κB. This was reduced in the presence of 50 μg/ml Cpn10 by 5- to 10-fold.

To further investigate the effect of Cpn10 on responsiveness of HEK293 cells expressing TLR9 to CpG DNA, similar experiments to those described above were performed using varying concentrations of Cpn10-12.5 λg/ml, 25 μg/ml, 50 μg/ml and 100 μg/ml (see FIG. 5). These results confirm the Cpn10-mediated effect observed above (FIG. 4) and illustrate the dose-responsiveness of the Cpn10-mediated effect on TLR9 signalling.

Example 5

Cytokine Release from Human Peripheral Blood Mononuclear Cells

To determine the ability of Cpn10 to modulate cytokine release in primary human cells, human peripheral blood mononuclear cells (PBMCs) isolated from healthy volunteer donors were used. PBMCs were isolated from heparinized blood by buoyant density gradient centrifugation as described in Johnson et al., 2005 (*J Biol Chem* 280:4037-4047).

One half of the isolated PBMCs were treated to remove plasmacytoid dendritic cells (PDCs) from the cell population using anti-BDCS-2-APC columns (Miltenyi) as described in Latz et al., 2004 (*Nature Immunol* 5:190-198). PDCs are the primary source of the type I interferon IFNα within the PBMC population. PDCs are known to express TLR7 and TLR9 and are the critical cell type in humans for recognition of single stranded nucleic acids.

For both PBMC containing PDCs and PBMC depleted of PDCs, cells were seeded into 96-well plates at $10^6$ viable cells per ml in 200 µl and cultured as described in Johnson et al., 2005 (*J Biol Chem* 280:4037-4047). Briefly, Cpn10 was added to a final concentration of 1 µg/ml, 10 µg/ml or 50 µg/ml and plates incubated for 1 hour before LPS (non-repurified or repurified) was added. Cells were then incubated for a further 20 hours at 37° C. and 5% $CO_2$. Supernatants were collected and analysed for production of the pro-inflammatory cytokine TNF-α (FIG. 6) and the anti-inflammatory cytokine IL-10 (FIG. 7) using specific ELISAs according to manufacturer's instructions (R&D Systems, Inc., Minneapolis, Minn.).

As shown in FIGS. 6 and 7, neither medium alone nor Cpn10 induced production of TNF-α or IL-10 in the absence of LPS.

Figure 6A:
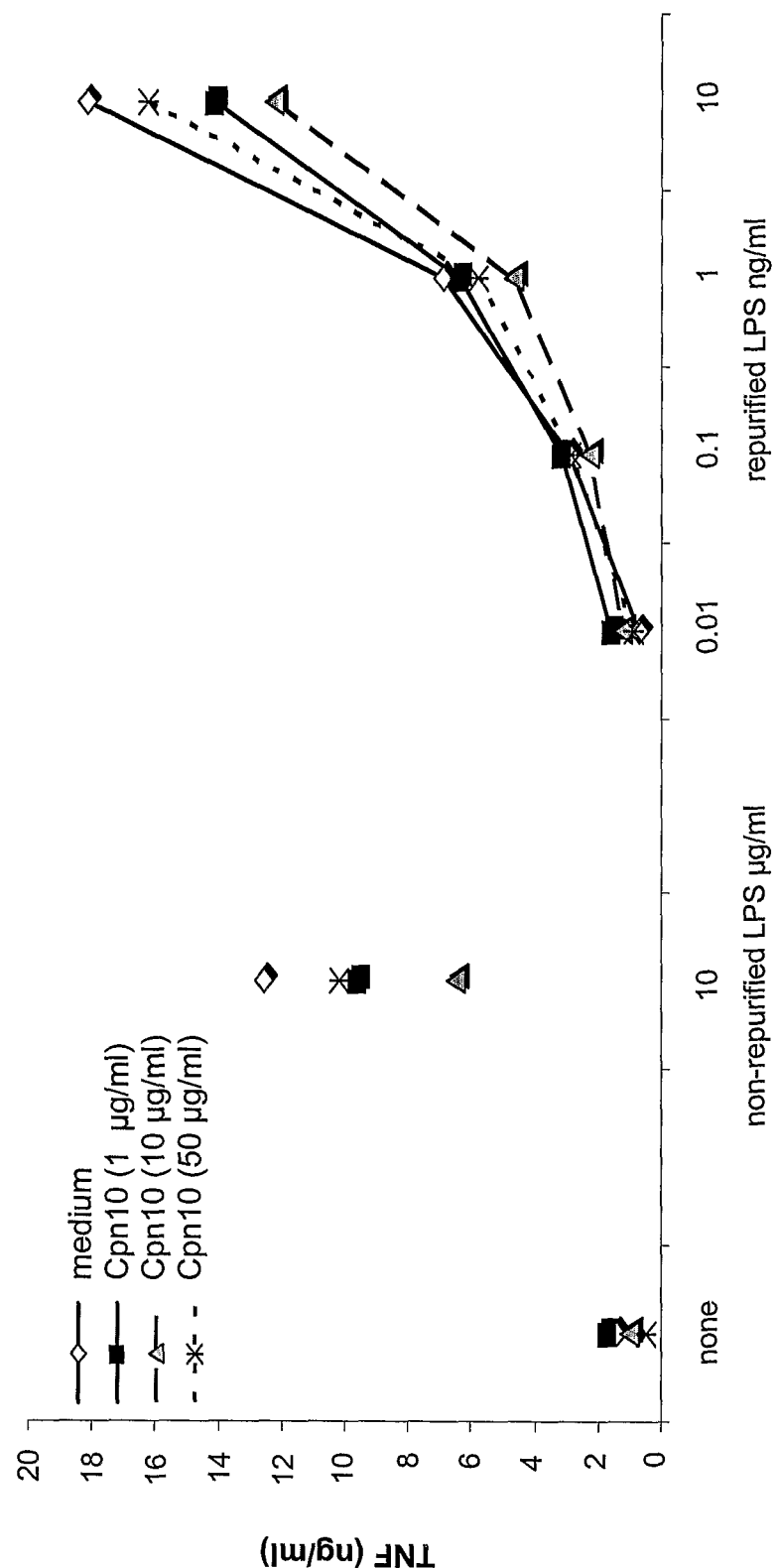
Figure 6B:
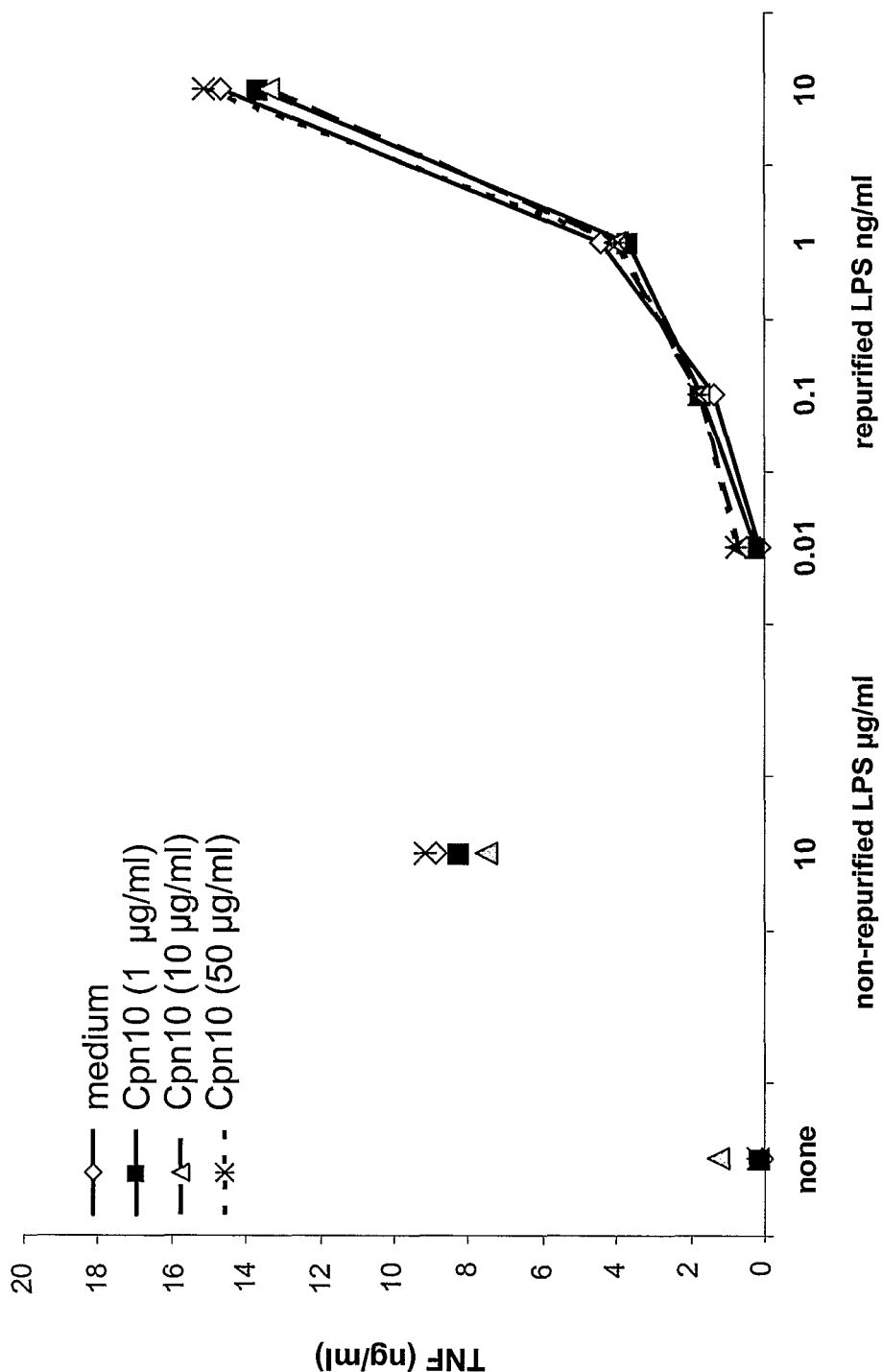

The addition of re-purified LPS (from 0.01-10 ng/ml) to intact PBMC cultures resulted in production of TNF-α that was dose-responsively decreased (maximum 32%) in the presence of up to 10 µg/ml Cpn10 (FIG. 6A). However in PBMC depleted of PDCs, the influence of Cpn10 on TNF-α production was lost (FIG. 6B). Thus the effect of Cpn10 on the LPS-induced production of TNF-α requires the presence of PDCs and is cancelled in their absence. This finding is somewhat surprising as PDCs do not express TLR4 and thus do not respond to stimulation with LPS, thus suggesting that the modulatory effect of Cpn10 on TLR4 directed signaling may be indirect.

Figure 7A:
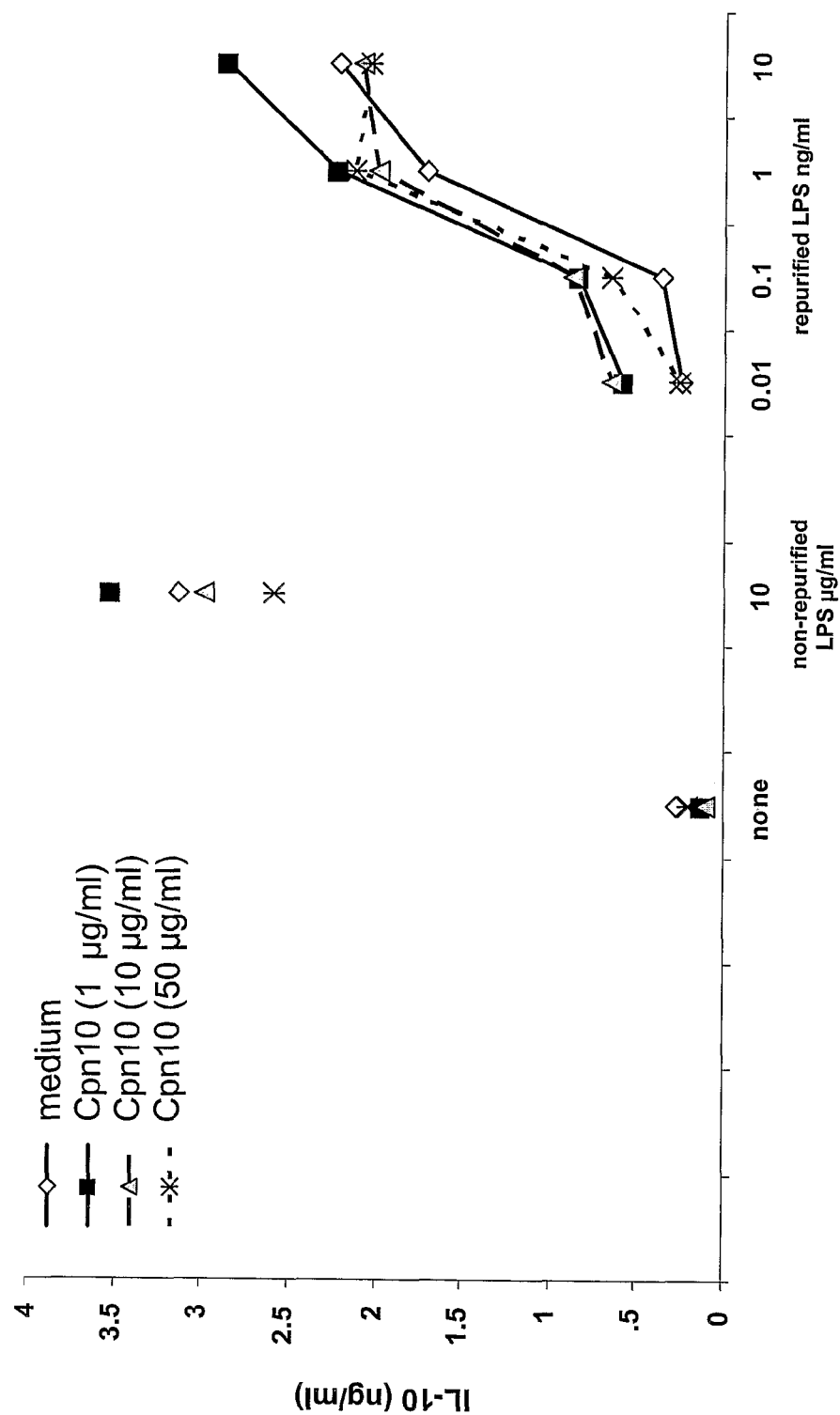
Figure 7B:
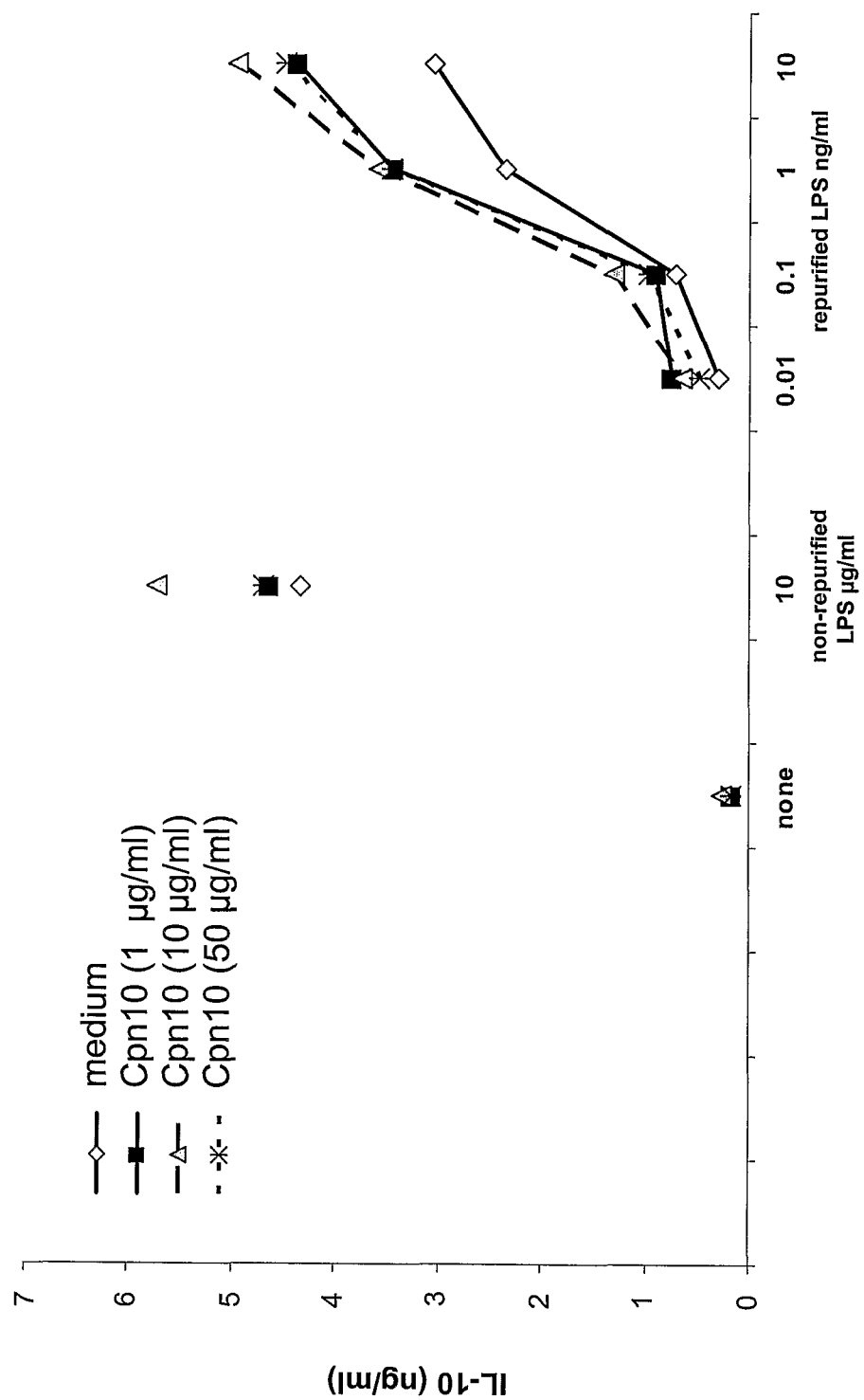

In the case of IL-10 (FIG. 7), supernates from PBMC demonstrated increase in IL-10 production in the presence of Cpn10, although supernates from PBMC depleted of PDCs demonstrated a greater dose-responsive (up to 10 µg/ml Cpn10) increase in IL-10 production (FIG. 7B) than observed in intact PBMC with PDCs (FIG. 7A).

Example 6

Cpn10 Modulation of TLR3 Activation

This study was undertaken to determine whether Cpn10 differentially regulates the response to ligation of TLR3 verses other TLRs, which may indicate a target of molecular interaction.

Stimulation of TLRs by specific agonists triggers the activation of two downstream signaling pathways, either MyD88-dependent or -independent. MyD88 is an adaptor molecule common to all TLRs, except for TLR3. The function of this molecule is to recruit IL-1R-associated kinase (IRAK) and TNFR-associated factor 6 (TRAF6) together to activate IκB (IKK)αβγ kinase complex, which then phosphorylates IκBα, leading to nuclear translocation and DNA binding of NF-κB. MyD88-independent activation of TLRs involves activation of Toll/IL-1R domain-containing adaptor inducing IFN-β (TRIF). This results in delayed activation of NF-κB, and IFN regulatory factor 3 (IRF3) which leads to the production of IFN-β and expression of IFN-inducible genes. Ligation of TLR3 primarily activates the TRIF pathway, whereas TLR4 activates both MyD88- and TRIF-dependent pathways. One of the aims of this study was to determine whether Cpn10 could regulate the dynamics of the response due to activation of TLR3 verses other TLRs, and thereby provide some information on the target and mode of action of Cpn10.

6.1 General Materials

Cpn10 batch CH003 and GroES were used with and without LPS (Sigma) and Poly(I:C) (Invivogen). Cell lines used included RAW264-pNifty2-LUC and RAW264.7.

6.2 Results 6.2.1 Cpn10 does not Inhibit NF-κB Activation Through TLR3

The mouse macrophage-like cell line RAW264.7 was stably transfected with a plasmid driven by the ELAM1 promoter (RAW264-pNifty2-LUC). The ELAM1 promoter is proximal to five NF-κB sites and drives the expression of a luciferase reporter gene in response to nuclear translocation and activation of the NF-κB transcription factor in cells. As shown in FIG. 8, the presence of a broad concentration range of Cpn10 did not alter the dynamics of TLR3-induced NF-κB activation in RAW264-pNifty2-LUC cells stimulated with Poly(I:C). Poly(I:C) is a synthetic analog of double-stranded RNA, a molecular pattern associated with virus infection which activates NF-κB via interaction with TLR3.

6.2.2 Cpn10 Dose-Responsively Increases Production of Type I IFNS in Response to TLR3 and TLR4 Ligation RAW264.7 cells were pre-incubated for 2 hours with Cpn10 then stimulated with LPS or Poly(I:C) for 24 hours. At this point cell culture supernatant was collected and analysed for IFNα/β antiviral activity using a cytopathic effect reduction bioassay as previously described (Hamilton et al., (1996) *J Immunol* 156(7):2553). As shown in FIG. 9 below, stimulation through either TLR4 (LPS) or TLR3 [Poly(I:C)] for 24 hours in the presence of Cpn10 lead to an up-regulation of Type I IFNs.

RAW264.7 cells were then seeded at $2.5 \times 10^5$/ml in sterile 24 well plates and allowed to adhere for 16-20 hrs. Cells were pre-incubated in the presence of a titration of Cpn10 then stimulated with LPS (TLR2/4) or Poly (I:C) for 4 or 6 hrs. Cell lysates were collected and either frozen at −70° C. or processed immediately for direct mRNA isolation using Dynabeads. mRNA was reverse transcribed with oligo (dT) primers and Superscript III First-Strand Synthesis System for RT-PCR. The resultant cDNA was amplified in a PCR with mouse IFN β specific primers. To verify that equivalent amounts of template were added to each reaction and to confirm uniform amplification, GAPDH (glyceraldehyde-3-phosphate dehydrogenase) was transcribed and amplified for each sample. PCR products were separated on agarose gels and visualized after ethidium bromide staining as shown in FIG. 10.

In addition to data from the mouse macrophage cell line RAW264.7, it was also demonstrated that human PBMC stimulated with Poly(I:C) show increased production of type I IFN (IFN-α) in the presence of Cpn10, as shown in FIG. 11.

6.2.3 GroES, the *E. Coli* Homologue of Cpn10, Cannot Augment Poly(I:C)-Induced IFN-β Production In order to determine the specificity of the Cpn10-mediated increase in Poly(I:C)-induced IFN-β production, the *E. coli* Cpn10 homologue, GroES, was tested. As shown in FIG. 12, GroES did not modulate the production of IFN-β induced by Poly(I:C) through TLR3.

6.2.4 Pre-Incubation with Cpn10 Followed by a Wash Abrogates the Dose-Responsive Increase in Poly(I:C)-Induced IFN-β Production In LPS stimulation assays, pre-incubation with Cpn10 followed by a PBS wash prior to addition of LPS did not impact the ability of Cpn10 to modulate the activation of NF-κB. However, in the Poly(I:C) assay, pre-incubation of RAW264 cells with Cpn10 followed by a PBS wash dramatically reduced the Cpn10 dose-responsive increase in IFN-β production with Poly(I:C) stimulation as shown in FIG. 13.

6.2.5 Cpn10 Modulation of a Poly (I:C)- or LPS-Induced Response Requires Positive Feedback of the Type 1 Interferon Pathway Mice with a null mutation in the IFNAR1 (interferon-associated receptor 1) component of the type 1 IFN receptor are characterized by a complete lack of antiviral responses corresponding to increased susceptibility to viral infection and a loss of antiproliferative responses to IFNα/β (Hwang et al., (1995) Proc. Natl. Acad. Sci. USA 92: 11284). IFNAR1 deficient mice (IFNAR1/−) have an absence of constitutive IFN activity and abnormalities in the proportions and responses of hemopoietic cells, including macrophages.

An ex vivo assessment of the involvement of Cpn10 in an IFN 'priming' response was performed using bone marrow derived macrophages (BMMs) isolated from wildtype (wt) or IFNAR1−/− mice. BMMs were isolated and activated with a panel of TLR agonists (Poly(I:C)-TLR3 or LPS-TLR4) in the presence of a dose titration of Cpn10. Supernatants were collected after 24 hours and cytokine levels analysed using a BD Mouse Inflammation CBA and mouse IFNβ ELISA kit. Results from these assays indicate that a positive feedback response through the IFNAR1 receptor is necessary for Cpn10 modulation of both Poly (I:C)-induced IFNβ production (FIG. 14) and LPS-induced TNF-α production (FIG. 15).

These data, which link the IFN feedback pathway to Cpn10-mediated activity, were further corroborated with in vivo results from a mouse endotoxaemia study. In this murine model of sepsis, mice were pre-treated for 30 minutes with 100 μg Cpn10 via i.v. administration prior to i.v. injection of 10 μg LPS. Serum was collected after 1.5 hours and analysed for pro-inflammatory cytokine production using a BD Mouse Inflammation CBA and IFNβ ELISA. A significant (p<0.05) reduction in serum TNFα levels in mice co-treated with Cpn10 correlated with a significant (p<0.01) decrease in serum IFNβ levels as shown in FIG. 16.

6.3 Discussion and Conclusions

At least one exception to the pattern of Cpn10-mediated NF-κB modulation involves activation of cells by the TLR3 ligand Poly(I:C). In this TLR3 system, Cpn10 was found to have no effect on NF-κB activation in response to Poly(I:C) stimulation of cells.

In addition, Cpn10 was found to induce a synergistic increase in production of type I interferons in response to Poly(I:C). One explanation for this apparent anomaly is that Cpn10 participates in the modulation of a priming or feedback loop response. For example, Type 1 interferons have been shown to play important roles in the LPS-regulated response either directly or indirectly (for example, through SOCS1). This is a significant development in understanding Cpn10 mechanisms of action in that it suggests Cpn10 triggers the downregulation of pro-inflammatory cytokines such as TNFα by dampening early cellular priming by type I IFN.

Example 7

Cpn10 Modulation of Semliki Forest Virus (SFV) Infection in Mice

This series of studies was undertaken to determine whether administration of Cpn10 affected the lethality of Semliki Forest Virus (SFV) in a mouse model, and whether Cpn10 modulates Type I IFN production in response to TLR activation.

The in vivo model involved a systemic infection of Semliki Forest Virus (SFV) for initial determination of modulation of the antiviral activity of type I IFNs. The model can be performed in neonatal mice where all organs including the brain are infected, causing lethality within 4-6 days depending on the dose, and therefore has the advantage of sensitivity and acuteness of infection. Alternatively the model can be tested in adult mice that are less susceptible to the virus, due to type I IFN production. It is understood that production of IFN within the first 24-48 hrs following virus infection results in decreased viral titres. This model is amenable to analyses of "chronic" responses including serum analyses and immune responses.

The in vitro study included a series of assays to test the effect of priming of macrophages on Cpn10 modulation of cytokine production in response to TLR activation, including the comparison of freshly-isolated bone marrow macrophages from WT and IFNAR deficient mice.

7.1 Materials and Methods

Cpn10 batch CH003 was used at 5.0 mg/ml in 50 mM Tris, and 150 nm NaCl with endotoxin <0.01 EU/ml. Diluent formulation buffer comprised 50 mM Tris and 150 mM NaCl. Pam3cys and polyI:C was from Invivogen. Mice were C57BL/6.

For the in vivo study, a pre-study involving viral titration was undertaken in mice to set appropriate virus batch and dosages. For the full study, 10-13 mice were used per group, with 3 groups of mice per dose of virus. Groups were treated as follows: (A) virus only; (B) virus+conc.A Cpn10; (C) virus+conc.B Cpn10. Neonatal mice about 6-9 days old were injected i.p. with Cpn10 (or formulation buffer) and SFV and maintained with their mothers. In addition, adult mice (wt and IFNAR deficient) 6-8 weeks old were injected i.p. with SFV, with Cpn10 administered i.p. every 12 hrs over the first week of viral infection, and at doses as determined.

For the in vitro study, the effect of macrophage priming on Cpn10 modulation of cytokine production in response to TLR activation and comparison of WT and IFNAR deficient macrophages was undertaken. Bone marrow derived macrophages (BMM) sourced from WT and IFNAR deficient mice were treated with the TLR agonists pam3cys (TLR2), polyI:C (TLR3), and LPS (TLR4) over a dose range of Cpn10.

7.2 Results

Data from the in vivo neonate viral infection study demonstrated a significant increase in survival of SFV-infected mice treated with Cpn10. The following groups of 6-9 day old neonate C57BL/6 mice comprised the study: Group A: SFV (n=13); Group B: SFV+Cpn10 20 μg (n=13); Group C: SFV+Cpn10 50 μg (n=13).

Group B and C were injected i.p. with 20 and 50 μg of Cpn10, followed (3 hrs later) by injection of 50 μl SFV (30×TCID50) to all three groups. Mice were housed with their mothers and handled carefully throughout the experiment. Pups were carefully monitored at regular intervals (12/24 hr) for standard signs of health status including mobility, condition, behaviour, etc.

At 72 hours 54% and 69% of 20 and 50 μg Cpn10 treated mice were alive, compared to 15% survival in untreated mice (FIG. 17). It was also noted that mice in the highest dose group were moving around whilst the other two groups were very sick and lying on their sides. By 84 hours all mice treated with SFV only succumbed to the virus, whilst 31% of both groups B and C were alive.

7.3 Discussion and Conclusions

Cpn10 administration prolonged survival after viral infection in a dose-dependent manner, as seen by the 72 h data. At 96 h post infection, 18% of mice injected with Cpn10 survive, while all untreated mice were dead at 88 hr post-infection. Survival of 50% and 70% of mice at 72 h post-infection in the two Cpn10 treated groups, versus 18% in the untreated group, was significant given the massive dose of virus administered. It was also noteworthy that this result was obtained after a single administration of Cpn10. These data suggest induction of antiviral protection by Cpn10.

Example 8

Cpn10 Associates with the CD14-Independent LPS Receptor Cluster

The plasma membrane of cells is composed of lateral heterogeneities, patches and microdomains. These membrane microdomains or lipid rafts are enriched in glycosphingolipids and cholesterol and have been implicated in cellular processes such as membrane sorting and signal transduction. The inventors proposed that Cpn10 may localise to the lipid raft during LPS signal clustering, by binding either directly to TLR4 or to one of the other participants of the cluster to disrupt signalling.

8.1 Materials and Methods

Cell labeling for FRET. MonoMac 6 cells (a human monocytic cell line) were labeled with 100 μl of a mixture of donor conjugated antibody (Cy3) and acceptor conjugated antibody (Cy5). For labelling of Cpn10, an anti-Cpn10 rabbit polyclonal antibody was used. The cells were rinsed twice in PBS/0.02% BSA, prior to fixation with 4% formaldehyde for 15 min. The cells were fixed in order to prevent potential re-organisation of the proteins during the course of the experiment.

Confocal imaging. Cells were imaged on a Carl Zeiss, Inc. LSM510 confocal microscope (with an Axiovert 200 fluorescent microscope) using a 1.4 NA 63× Zeiss objective. The images were analysed using LSM 2.5 image analysis software (Carl Zeiss, Inc.). Cy3 and Cy5 were detected using the appropriate filter sets. Using typical exposure times for image acquisition (less than 5 s), no fluorescence was observed from a Cy3-labelled specimen using the Cy5 filters, nor was Cy5 fluorescence detected using the Cy3 filter sets.

FRET measurements. FRET is a non-invasive imaging technique used to determine molecular proximity. FRET can occur over 1-10 nm distances, and effectively increases the resolution of light microscopy to the molecular level. It involves non-radiative transfer of energy from the excited state of a donor molecule to an appropriate acceptor (Wu and Brand (1994) *Anal. Biochem.* 218: 1-13). The rate of energy transfer is inversely proportional to the sixth power of the distance, between donor and acceptor (Kenworthy and Edidin (1998) *Journal of Cell Biology* 142: 69-84; Kenworthy and Edidin (1998) in Gelb, M. H. (Ed.) *Methods in molecular Biology*. Humana Press Inc, Totowa, N.J. pp 37-49). The efficiency of energy transfer (E) is defined with respect to r and $R_0$, the characteristic Förster distance by:

$$E = 1/[1+(r/R_0)^6] \qquad [1]$$

In the present study, FRET was measured using a method as previously described (Kenworthy and Edidin (1998) *Journal of Cell Biology* 142: 69-84; Kenworthy and Edidin (1998) in Gelb, M. H. (Ed.) *Methods in molecular Biology*. Humana Press Inc, Totowa, N.J. pp 37-49). Briefly, samples were labeled with donor and acceptor conjugated antibodies, and energy transfer was detected as an increase in donor fluorescence (dequenching) after complete photobleaching of the acceptor molecule. Cells labeled only with the 26ic-Cy3 probe were used in order to determine the minimum time required to bleach Cy3. Cy3 was bleached by continuous excitation with an arc lamp using a Cy3 filter set for 5 min. Under these conditions, Cy5 was not bleached. FRET images were calculated from the increase in donor fluorescence after acceptor photobleaching by:

$$E(\%) \times 100 = 10{,}000 \times [(Cy3\ \text{postbleach} - Cy3\ \text{prebleach})/Cy3\ \text{postbleach}] \qquad [2]$$

The scaling factor of 10,000 was used in order to expand E to the scale of the 12-bit images.

8.2 Results and Discussion

In the first set of data shown in Table 1, FRET was used to determine the concentration of receptor molecules involved in LPS-induced cell activation (MonoMac6 cells) in lipid rafts. By performing FRET experiments, it was possible to investigate whether Cpn10 (batch P003-04 or CH003), Hsp60, *E. coli* GroES and other molecules were co-localising with lipid rafts. FRET was measured in terms of dequenching donor fluorescence after complete photobleaching of the acceptor fluorophore. Increased donor fluorescence after destruction of the acceptor indicated that donor fluorescence was quenched in the presence of the acceptor because of energy transfer. The energy transfer efficiency in the system was tested using a positive control, that is, the transfer between mAbs to different epitopes on GM1 (ganglioside, a raft-associated molecule) molecules, showing that the maximum energy transfer efficiency (E %) was 37±1.0. A negative control between FITC-GM1 and rhodamine-MHC was also used, which revealed no significant energy transfer (3±0.4). This background FRET value is thought to be caused by random FRET as both species are present at high concentrations.

TABLE 1

Energy transfer efficiency values between donor-acceptor pairs.

| Donor (Cy3) | Acceptor (Cy5) | E ± ΔE (%) |
| --- | --- | --- |
| Unstimulated MM6 cells | | |
| GM1 | GM1 | 37 ± 1.0 |
| GM1 | MHC class I | 3 ± 0.4 |
| GM1 | CD14 | 34 ± 2.0 |
| GM1 | TLR4 | 5 ± 1.5 |
| GM1 | Hsp60 | 6 ± 0.5 |
| GM1 | GroES | 7 ± 1.5 |
| GM1 | Cpn10 | 15 ± 2 |
| MM6 cells stimulated with LPS | | |
| GM1 | MHC class I | 3 ± 0.5 |
| GM1 | CD14 | 35 ± 1.5 |
| GM1 | TLR4 | 32 ± 1.8 |
| GM1 | Hsp60 | 8 ± 2.0 |
| GM1 | GroES | 6 ± 1.0 |
| GM1 | Cpn10 | 28 ± 2.0 |

Energy transfer between different pairs was detected from the increase in donor fluorescence after acceptor photobleaching. Data represent mean±standard deviation of a number of independent experiments.

Data presented in Table 1 demonstrate that CD14 resides in lipid rafts, but that TLR4 was not found to be associated with lipid rafts prior to LPS stimulation, and is apparently recruited there after LPS stimulation.

The next set of data describes the proximity of Cpn10 to the TLR4 cluster, again using FRET. In Table 2, the positive control was TLR4 with itself, and gave a maximum energy transfer efficiency (E %) of 36±2.0.

TABLE 2

Energy transfer efficiency values between donor-acceptor pairs

| Donor (Cy3) | Acceptor (Cy5) | E ± ΔE (%) |
| --- | --- | --- |
| Unstimulated MM6 cells | | |
| TLR4 | TLR4 | 36 ± 2.0 |
| Cpn10 | CD14 | 12 ± 0.5 |
| Cpn10 | Hsp70 | 9 ± 1.0 |
| Cpn10 | Hsp90 | 6 ± 2.0 |
| Cpn10 | CXCR4 | 3 ± 1.0 |
| TLR4 | Hsp60 | 5 ± 1.0 |
| CD14 | Hsp60 | 6 ± 0.5 |
| Cpn10 | Hsp60 | 5 ± 2.0 |
| GroES | CD14 | 8 ± 1.0 |
| GroES | TLR4 | 7 ± 1.5 |
| GroES | Hsp70 | 6 ± 1.0 |
| GroES | Hsp90 | 7 ± 1.5 |
| GroES | CXCR4 | 4 ± 2.0 |
| MM6 cells stimulated with LPS | | |
| Cpn10 | TLR4 | 36 |
| Cpn10 | CD14 | 32 ± 0.5 |
| Cpn10 | Hsp70 | 24 ± 1.0 |
| Cpn10 | Hsp90 | 18 ± 12.0 |
| Cpn10 | CXCR4 | 12 ± 1.0 |
| TLR4 | Hsp60 | 6 ± 1.0 |
| CD14 | Hsp60 | 4 ± 2.0 |
| Cpn10 | Hsp60 | 6 ± 1.5 |
| GroES | CD14 | 7 ± 0.5 |
| GroES | TLR4 | 8 ± 1.0 |
| GroES | Hsp70 | 7 ± 1.5 |
| GroES | Hsp90 | 8 ± 2.0 |
| GroES | CXCR4 | 3 ± 1.0 |

Energy transfer between different pairs was detected from the increase in donor fluorescence after acceptor photobleaching. Data represent mean±standard deviation of a number of independent experiments.

As shown in Table 2, Cpn10 did not associate with Hsp70, Hsp90 or CXCR4 in absence of LPS, but demonstrated an association with these members of the LPS-activation cluster after LPS stimulation. While the data demonstrating whether there is an association of Cpn10 with TLR4 prior to LPS stimulation is not shown here, there is a strong association of Cpn10 with TLR4 upon LPS stimulation.

These data also demonstrate that Hsp60 does not associate with TLR4, CD14 or lipid rafts prior to or following LPS stimulation of cells. Importantly, the *E. coli* homologue of Cpn10, GroES, which is routinely used as a negative control in experiments testing the activity of Cpn10 as an immune response modulator, also does not associate with the lipid raft or with other members of the CD14-independent LPS activation cluster.

Example 9

Cpn10 Interacts with TLR Clusters and within Lipid Rafts at the Surface of PBMC

In order to determine whether endogenously produced Cpn10 interacts at the surface of PBMC with TLRs, TLR-associated molecules and with components of lipid microdomains, the inventors used a FRET analysis using a fluorophore-labeled anti-Cpn10 antibody, in response to LPS stimulation of freshly-isolated human adherent monocytes. Since no recombinant Cpn10 was added to the cell culture prior to imaging, Cpn10 recognized at the cell surface would have been exported from intracellular stores.

9.1 Materials and Methods

Cell labeling for FRET. PBMC were isolated from healthy donor blood using density gradient centrifugation over Ficoll-Hypaque and adherent cells prepared. Cells were washed in order to remove non-adherent cells. The remaining adherent cell monolayers ($1-2 \times 10^5$ monocytes/well) were cultured in 24-well plates in serum-free medium (Gibco) supplemented with 0.01% L-glutamine and 40 µg/ml gentamicin. An aliquot of the enriched monocyte preparation was routinely assessed for purity by flow cytometry (>80% pure). Alternatively, monocyte-derived DC were cultured for 5 days from enriched adherent peripheral blood monocytes with GM-CSF and IL-4 (R&D Systems) according to the published protocol (Bender, A et al. 1996. *J Immunol Methods* 196:121-135) prior to the FRET assay.

Cell labeling for FRET analysis was performed essentially as previously published (Trianitafilou, K 2001. *Nat Immunol* 2:338-345). Freshly-isolated human monocytes or monocyte-derived DC were stimulated with 100 ng/ml LPS (Re-LPS from *S. minnesota*, List Labs, CA), 10 ng/ml *S. aureus* LTA (kind gift from Thomas Hartung, Konstanz, Germany), 0.1 µg/ml poly(I:C), 20 ng/ml imiquimod, 1 µM CpG ODN (Invivogen), 25 µg/ml ssRNA purified from Coxsackievirus B3, or buffer control for 10 min, washed, and then labeled with a 1:1 mixture of donor-conjugated antibody (Cy3) and acceptor conjugated antibody (Cy5). Cells were then fixed to prevent potential reorganization of proteins.

Antibodies. Antibodies used in FRET analysis included: Cpn10 (Johnson, B. 2005. *J Biol Chem* 280:4037-4047), Hsp70, CXCR4, TLR3, TLR7, TLR9 (Santa Cruz), TLR2 (Genentech), Hsp90 (Bioquote), CD14 (26ic, ATCC, from HB246 hybridoma), GM1 (GM1-1, Calbiochem, GM1-2b, North Star Bioproducts, Liverpool, UK), MHC class I (MCA115, Serotec), TLR4 (HTA125, HyCult). Antibodies were labeled with either Cy3 or Cy5 using FluoroLink labeling kit (AmershamPharmacia).

FRET measurements. Cy3 was excited with a helium/neon laser emitting at 543 nm, and Cy5 with a helium/neon laser emitting at 633 nm. Cells were imaged on a Carl Zeiss, Inc LSM510 META confocal microscope (with an Axiovert 200 fluorescent microscope) using a 1.4 NA 63× Zeiss objective. The images were analyzed using LSM 2.5 image analysis software (Carl Zeiss, Inc.). Cy3 and Cy5 were detected using the appropriate filter sets. Using typical exposure times for image acquisition (less than 5 s), no fluorescence was observed from a Cy3-labelled specimen. Tracks were scanned sequentially with only one laser and the respective detector channel active per scan. FRET was measured in terms of dequenching of donor fluorescence after complete photobleaching of the acceptor fluorophore. The efficiency of energy transfer (E) is defined with respect to r and $R_o$, the characteristic Forster distance by: $E=1/[1+(r/R_o)^6]$ (29). This method of FRET measurement was previously described (30).

9.2 Results

As shown in Table 3, endogenously-produced Cpn10 was found to associate with TLR4 and other members of the TLR4 signal complex after LPS stimulation. The identification of Cpn10 interacting with lipid raft moieties prior to LPS stimulation may indicate its release by dead cells, or up-regulation due to physical manipulation of cells during purification. The demonstration of endogenous Cpn10 within lipid raft domains suggests its mode of delivery to the cell surface and extracellular secretion.

TABLE 3-continued

Endogenous Cpn10 associates with lipid rafts and members of the TLR4 signaling complex on PBMC as determined by FRET

| Donor (Cy3) | Acceptor (Cy5) | E ± ΔE (%) |
|---|---|---|
| LPS-stimulated monocytes | | |
| MHC I | GM-1 | 4 ± 1.5 |
| CD14 | GM-1 | 36 ± 1.0 |
| TLR4 | GM-1 | 34 ± 1.2 |
| Cpn10 | GM-1 | 30 ± 2.0 |
| Cpn10 | CD14 | 34 ± 2.5 |
| Cpn10 | TLR4 | 35 ± 1.2 |
| Cpn10 | Hsp70 | 25 ± 1.0 |
| Cpn10 | Hsp90 | 20 ± 2.0 |
| Cpn10 | CXCR4 | 16 ± 1.0 |

Data represent mean ± s.d. from several independent experiments.

The inventors also sought to determine whether Cpn10 associates directly with other TLRs using FRET analysis and freshly isolated cells. FRET was measured in terms of dequenching of donor fluorescence after complete photobleaching of the acceptor fluorophore. As shown in Table 4, large dequenching was observed between Cpn10 and most TLRs (with the exception of TLR3) located both on the cell surface and within the endosome of monocyte-derived DC (MoDC) in the presence, but not the absence, of ligand. (Note that a positive FRET signal with TLRs 7 and 9 on MoDC most likely indicates the presence of a small number of pDC in the MoDC population of cells.)

TABLE 4

Cpn10 associates with TLRs at the cell surface and in the endosome of human MoDC in the presence, but not the absence, of ligand, as determined by FRET.

| | | Acceptor (Cy5) | | | | |
|---|---|---|---|---|---|---|
| | | TLR2 E ± ΔE (%) | TLR3 E ± ΔE (%) | TLR4 E ± ΔE (%) | TLR7 E ± ΔE (%) | TLR9 E ± ΔE (%) |
| Donor (Cy3) | Neg Ctrl | 8 ± 1.0 | 5 ± 0.2 | 8 ± 0.8 | 4 ± 0.4 | 5 ± 1.0 |
| | TLR4 Pos Ctrl | | | 36 ± 1.0$^a$ | | |
| | LTA | 28 ± 2.0 | 6 ± 1.0 | 8 ± 1.0 | 5 ± 0.6 | 5 ± 1.0 |
| | Poly(I:C) | 9 ± 1.2 | 7 ± 1.0 | 8 ± 0.5 | 9 ± 2.0 | 8 ± 1.0 |
| | LPS | 7 ± 1.0 | 5 ± 1.0 | 32 ± 1.5 | 5 ± 0.2 | 4 ± 0.5 |
| | Viral ssRNA | 9 ± 1.5 | 12 ± 0.8 | 8 ± 0.5 | 20 ± 2.0 | 15 ± 1.0 |
| | Imiquimod | 9 ± 1.2 | 13 ± 1.0 | 9 ± 1.5 | 21 ± 0.7 | 15 ± 1.2 |
| | CpG ODN | 8 ± 1.0 | 12 ± 1.0 | 9 ± 1.5 | 14 ± 1.4 | 22 ± 1.0 |

Energy transfer (E ± ΔE (%)) between different pairs was detected from the increase in donor fluorescence after acceptor photobleaching. For each pair, the donor (Cy3) was Cpn10, except in the control experiment where the donor (Cy3) was TLR4; the acceptor (Cy5) was the TLR. FRET was calculated from the increase in donor fluorescence after acceptor photobleaching by: E% × 100 = 10,000 [donor post-bleach − donor pre-bleach)/donor post-bleach]. Data represent mean ± s.d. from several independent experiments.

TABLE 3

Endogenous Cpn10 associates with lipid rafts and members of the TLR4 signaling complex on PBMC as determined by FRET

| Donor (Cy3) | Acceptor (Cy5) | E ± ΔE (%) |
|---|---|---|
| Unstimulated monocytes | | |
| GM-1 | GM-1 | 38 ± 1.0 |
| MHC I | GM-1 | 5 ± 1.5 |
| CD14 | GM-1 | 37 ± 2.0 |
| TLR4 | GM-1 | 6 ± 1.0 |
| Cpn10 | GM-1 | 20 ± 1.5 |
| TLR4 | TLR4 | 37 ± 1.0 |
| Cpn10 | CD14 | 10 ± 1.2 |
| Cpn10 | TLR4 | 10 ± 1.0 |
| Cpn10 | Hsp70 | 9 ± 1.2 |
| Cpn10 | Hsp90 | 5 ± 1.0 |
| Cpn10 | CXCR4 | 4 ± 1.5 |

Example 10

Effect of TLR Ligation on Cpn10

To determine the relationship between TLR ligation and Cpn10, and in particular, to test whether Cpn10 is an endogenous regulator of the immune system, the inventors examined whether endogenous Cpn10 is induced by cell stress in the form of TLR ligation or cytokine activation. The inventors also examined whether Cpn10 is released from cells when subjected to appropriate stimuli, and whether Cpn10 was able to limit the signal induced by ligands to other TLRs.

10.1 Materials and Methods

Reagents. Recombinant human Cpn10 was produced to GMP specifications by BresaGen Limited (Adelaide, Aus) essentially as described previously (Johnson, B. 2005. J.

Biol Chem 280:4037-4047). The purity of Cpn10 was determined to be >99% by SDS-PAGE, and showed the same molar activity as GroES in a GroEL-mediated rhodanese refolding assay (Brinker, 2001. Cell 107:223-233) (data not shown). For FACS analysis, a cysteine residue was engineered onto the C-terminus of Cpn10 and labeled with AlexFluor647 (Invitrogen) according to manufacturer's instructions. LPS contamination of Cpn10 was determined by Endosafe assay (Charles River Laboratories) to be routinely <0.2 EU/mg protein. TLR ligands and cytokines included: E. coli LPS (strain 055:B5, Sigma), E. coli ultra-pure LPS (0111:B4 Sigma), S. aureus LTA, B. subtilis LTA, S. aureus PGN, B. subtilis PGN, zymosan cell wall from S. cerevisae, poly(I:C), imiquimod R837, CpG ODN 1826 and ODN2216, GpC ODN1826 control, (all from Invivogen, San Diego, Calif.), recombinant mouse IFNγ, (Chemicon), IL-1β (PeproTech), and recombinant human TNF-α (Invivogen).

Antibodies. Rabbit polyclonal antibodies were raised against Cpn10 and affinity purified at CBio. Cytometric Bead Array (CBA) Flex Sets recognizing phosphorylated signal proteins (both human and mouse) including ERK1/2 (T202/Y204), JNK1/2 (T183/Y185), p38/MAPKinase (T180/Y182), CD14, and FcBlock (CD16/CD32) were from BD.

Transfection, Cell Stimulation and Promoter analysis. The pCAT/LUC-CPN promoter construct was provided by M. Ryan and N. Hoogenraad (La Trobe University, Melbourne). RAW264.7 cells were transiently transfected using Gene-Juice (Novagen). After 24 h cells were harvested and cell viability assessed by trypan blue dye exclusion. Cells were seeded into 24-well plates and heat shocked (43° C. for 15 min (mild), 30 min (moderate), or 60 min (severe)) followed by recovery at 37° C. or stimulated after 18 h. Cells were washed, harvested in Cell Culture Lysis Reagent (CCLR, Promega) and firefly luciferase signal measured using the Luciferase Assay System (Promega) and the Wallac Victor 2 Multilabel Counter (Perkin-Elmer).

Real-time PCR. RAW264.7 cells were seeded at $2.5 \times 10^5$/ml in sterile 24 well plates and adhered for 16-20 hrs prior to stimulation. Replicate samples for each condition were assayed. mRNA was isolated using Dynabeads (Dynal) and reverse transcribed with oligo (dT) primers and Superscript III First-Strand Synthesis System for RT-PCR (Invitrogen). The resultant cDNA was amplified in duplicate in 10 μl qPCR reactions each containing 2.5 μl of a diluted (20%) cDNA template, 6.25 μl Platinum SYBR Green qPCR Supermix-UDG (Invitrogen) and 0.25 μl each of 10 μM sense and antisense primers. The reaction conditions were as follows: 95° C. 2 mins, 40 cycles of 95° C. 10 s, 60° C. 15 s and 72° C. 20 s with a final melt step 72-95° C. for 50 s. The qPCR reaction was performed on the Rotor-Gene 3000 instrument (Corbett Research). Target gene expression was normalized to housekeeper controls and analysed as previously described (Livak(, K. J., and T. D. Schmittgen. 2001, Methods 25:402-408). Primers: 18S sense CGG CTA CCA CAT CCA AGG AA (SEQ ID NO: 5), 18S antisense GCT GGA ATT ACC GCG GCT (SEQ ID NO: 6); Cpn10 sense GCC GAA ACT GTA ACC AAA GG (SEQ ID NO:7), Cpn10 antisense CAG GCT CAA TCT CTC CAC TC (SEQ ID NO: 8); Pbgd sense CCT GGT TGT TCA CTC CCT GA (SEQ ID NO: 9), Pbgd antisense CAA CAG CAT CAC AAG GGT TTT (SEQ ID NO: 10).

Qualification of endogenous Cpn10 in cell culture supernatant, cell lysates, and patient sera. Non-transfected RAW264.7 cells were treated as described, and culture supernatants concentrated. Cells were assessed for viability, pooled per condition (n=4), pelleted by centrifugation and resuspended in CCLR. Total cell protein content was quantified by modified Bradford assay (BioRad). Levels of Cpn10 in cell supernatants and in extracts (25 μg per sample) were analyzed by ELISA (detection limit 0.195 ng/ml). Serum from clinical trial subjects was tested at study entry for levels of circulating Cpn10 by ELISA. These trials were conducted according to GCP guidelines and written informed consent was obtained from each subject prior to sample testing. Trial protocols were approved by human ethics committees at local centers.

RAW264.7-HIV-LTR-LUC Assay. The RAW264.7-HIV-LTR-LUC assay was performed essentially as described previously (Johnson, B. 2005. J Biol Chem 280:4037-4047). Cells were pre-incubated with Cpn10 or control buffer for 2 h followed by addition of a dose range of TLR ligand. In each assay, Cpn10 was tested in a concentration range of 25-100 μg/ml, and ligands were used at concentrations which elicited a sharp dose-response curve, i.e. E. coli LPS at 0.2-5 ng/ml, Ultra-Pure E. coli LPS at 5-10 ng/ml, LTA and PGN at 10-100 μg/ml, zymosan at 10-100 μg/ml, poly(I:C) at 10-100 μg/ml, imiquimod at 1-10 μg/ml, and CpG ODN at 3.25-16.25 μg/ml. Incubation times with each agonist were optimized to ensure sufficient signal over background. As a negative control for human Cpn10, the E. coli homologue of Cpn10, termed GroES was routinely used (purified essentially as previously described (Brinker, 2001. Cell 107:223-233)). Note that the level of endotoxin contamination in Cpn10 and GroES preparations and in TLR ligand reagents was known to be less than the level shown previously to induce HIV-LTR activation at the concentrations used in these assays with this cell line (Johnson, B. 2005. J. Biol Chem 280:4037-4047).

Human PBMC cytokine assays. PBMC were isolated from healthy volunteer blood by buoyant density gradient centrifugation on Ficoll-Paque Plus (Amersham Biosciences). PBMC were pre-treated with Cpn10 (or buffer control) for 1 h, followed by stimulation with agonist for 20 h at 37° C. and 5% $CO_2$ prior to collection of culture supernatants. Cytokine levels were analyzed using CBA (BD) or ELISA (Bender MedSystems).

Detection of protein phosphorylation. RAW264.7 or PBMCs were incubated with Cpn10 for 2 h, followed by LPS stimulation for 30 min, centrifuged and pellets lysed with 0.1% SDS in PBS. Lysates were boiled for 5 min, cooled, cellular debris pelleted by centrifugation, and supernatants assayed for protein concentration as above. Phosphorylated signal proteins were detected using BD CBA Flex Sets for p38, ERK1/2 and JNK1/2. Alternatively, RAW264.7 were treated with Cytofix/Cytoperm (BD) and dual-stained for intracellular p38 and cell surface CD14. Samples were analyzed using the BD FACSArray Bioanalyzer with FCAP array software.

Statistical analysis. Changes in promoter activity following cell stimulation were assessed using one way ANOVA and Tukey's Multiple Comparison Test comparing unstimulated to stimulated conditions at optimal agonist concentrations. Cpn10 in subject serum samples were tested for significance between groups using one-way ANOVA and Tukey's Multiple Comparison Post Test.

10.2 Results 10.2.1. TLR Ligation Induces the Cpn10 Promoter

RAW264.7 cells were transfected with a reporter construct where luciferase production was under the control of the Cpn10 promoter. Purified recombinant IFN-γ, TNF-α and IL-1β were tested as non-TLR agonists. Cells treated with moderate heat shock (43° C., 30 min) demonstrated significant induction of the Cpn10 promoter at the 6 h recovery timepoint, with return to basal level by 18 h (FIG. 18A). It was then established that TLR agonists dose-dependently induced the Cpn10 promoter, with maximal activation observed after 20 hours (FIGS. 18A and 19C). Agonist concentrations were then optimized to induce maximal promoter response (FIG. 18B-G).

Comparison of responses to TLR and non-TLR agonists demonstrated a distinct profile of Cpn10 promoter activity (FIG. 18H). A significant up-regulation of Cpn10 was observed in response to ligands of TLR 2, 7 and 9, suggesting a correlation with the MyD88-dependent TLR signaling pathway. No significant up-regulation of the Cpn10 promoter was observed using TLR ligands which can utilize the TRIF-dependent signaling pathway (TLR3 and 4). Furthermore, the non-TLR agonists IFNγ, IL-1β and TNF-α did not induce substantial up-regulation of the Cpn10 promoter, indicating a certain degree of specificity in the transcriptional control of Cpn10.

As another demonstration of TLR-induced Cpn10 transcription, real-time PCR analysis was used to show that LTA stimulation of RAW264.7 cells results in concentration-dependent induction of Cpn10 mRNA, with maximal induction at 18 h and return to near baseline level by 24 h post-stimulation (FIG. 18I).

10.2.2. Cpn10 is Released from Cells Following TLR Ligation

To examine whether Cpn10 is released from cells when subjected to the appropriate stimuli, the inventors stimulated RAW274.7 cells with LTA and monitored by ELISA the presence of endogenous Cpn10, and Cpn10 released by cells into the culture medium. Analysis of cell lysates revealed little change in intracellular Cpn10 levels from LTA treated and control cells (FIG. 19A). Analysis of the culture supernatants, however, revealed a 3-fold increase in soluble Cpn10 after 30 h (FIG. 19B) over unstimulated control cells. In addition, levels of extracellular Cpn10 produced by stimulated cells correlated with the increases seen in Cpn10 promoter activity over time (FIG. 19C). These data indicate that a proportion of newly synthesized Cpn10 produced under conditions of immune challenge is released by cells. Analysis of culture supernatants from cells (either RAW264.7 or pCAT/LUC-CPN-transfected RAW264.7 cells) exposed to mild, moderate or severe heat shock (HS) demonstrated little accumulation of extracellular Cpn10 by comparison with supernatant from cells stimulated with LTA (FIG. 19D). These data suggest that Cpn10 is induced by HS to assist in mitochondrial protein misfolding, while specific immune challenge leads to the extracellular accumulation of Cpn10.

In order to gain evidence that Cpn10 may be regulated in disease, the inventors tested baseline serum levels of Cpn10 in patients suffering from chronic inflammatory diseases and compared these to a cohort of healthy volunteers. As shown in FIG. 19E, circulating levels of Cpn10 in patients with rheumatoid arthritis were significantly higher than in patients with multiple sclerosis, psoriasis or in healthy subjects (1.32 ng/ml±1.41, n=23, 0.44 ng/ml±0.46, n=46; 0.55 ng/ml±0.52, n=25; 0.45 ng/ml±0.32, n=24, respectively). Respective serum levels of Cpn10 may therefore correlate with ongoing inflammation on an individual and/or disease level. Whether due to passive release following cell lysis or stimulated release following immune cell stimulation during inflammatory challenge, it is clear that Cpn10 accumulates in the extracellular milieu, and that its export is enhanced with certain cell stimuli.

10.2.3. Cpn10 Limits the Dynamics of TLR Signaling

The inventors examined whether recombinant Cpn10 was able to limit the signal induced by ligands to other Toll-like receptors. Pre-incubation of this reporter cell line with an optimal concentration of Cpn10 for 2 h prior to stimulation with a variety of TLR ligands, ranging from Gram-positive bacterial peptidoglycans (PGN) and lipoteichoic acids (LTA) to synthetic RNA and DNA motifs, resulted in significant reductions in NF-κB-induced luciferase activity by comparison with cells stimulated in the absence of exogenous Cpn10. With the exception of the synthetic TLR3 ligand polyinosine-polycytidylic acid (poly(I:C)), the presence of Cpn10 in cell cultures stimulated with all other tested TLR ligands resulted in 20-80% inhibition of luciferase activity (FIG. 20A). These results indicate that Cpn10 is able to modulate the strength of signal of the immune response generated by ligands to most TLRs.

Stimulation of cells with LPS triggers both MyD88-dependent and -independent signaling cascades. The MyD88-dependent cascade is shared by all TLRs with the exception of TLR3, and involves NF-κB and the mitogen-activated protein (MAP) kinases (MAPK), including p38, extracellular signal-regulated kinase (ERK), and c-Jun N-terminal kinase (JNK). Both of these pathways culminate in regulation of the initiation and dynamics of an immune response. In order to elucidate the events by which Cpn10 regulates both NF-κB activation and cytokine production following stimulation of cells, the inventors analyzed the levels of phosphorylation of key proteins involved in the MAP kinase signal pathway. As shown in FIG. 20B-D, Cpn10 dose-responsively reduced the level of LPS-induced phosphorylation of p38, ERK1/2 and JNK1/2 in both a mouse macrophage cell line (RAW264.7) and in freshly isolated human PBMC. Since activation of the MAPK pathway is closely linked with induction of the inflammatory cascade of cytokine production, these data demonstrate that Cpn10-mediated changes in ligand-induced cytokine production result from changes in the TLR signal cascade.

To confirm the activity of Cpn10 on production of cytokines by freshly-isolated human cells stimulated with a variety of TLR ligands, the inventors pre-treated PBMC from healthy donors with or without Cpn10 for 1 h and then stimulated with a selected range of TLR ligands for 20 hours. Cytokine levels in cell culture supernatants were then assayed using ELISA or cytometric bead array (CBA). As shown in FIG. 20E, cytokine production induced by agonists to TLR2, TLR2/6 or TLR4 (PGN, LTA, Zymosan, LPS), including TNF-α, IL-1β, IL-6 and IL-10, was inhibited in the presence of Cpn10. Note that while Cpn10 mediated a slight induction of LPS-induced IL-10 production, the data demonstrate reduced IL-10 production in response to other TLR ligands. Similarly, stimulation of PBMC with agonists to TLR7 or 9 with imiquimod or CpG ODN in the presence of Cpn10 led to reduced production of TNF-α and increased IFNα, by comparison with control cultures without Cpn10.

10.3 Discussion

This study uncovers a previously unidentified role of Cpn10 as an endogenous regulator of the immune system. Stimulation of cells via the TLR system of receptors, but not through TNF-α, IFNγ or IL-1β preceptors, induces the Cpn10 promoter and production of Cpn10 protein that can be measured in the extracellular medium. The addition of recombinant Cpn10 dose-responsively limits TLR-driven cell activation, as assessed by NF-κB activation, MAPK phosphorylation, and production of cytokines by a murine cell line and by freshly-isolated human PBMC in vitro.

These results demonstrating induction of Cpn10 with immune insult, together with data showing Cpn10-mediated limitation of the magnitude of an inflammatory response, provides strong evidence that Cpn10 is an essential member of a negative feedback pathway central to the immune response network.

Example 11

Cpn10-Induced Modification of TLR4 Expression Upon LPS Stimulation

The inventors sought to determine the effect of Cpn10 on TLR4 expression in RAW264 cells in order to examine whether Cpn10 affects the surface expression of TLR4 upon LPS stimulation 11.1 Materials and Methods LPS was sourced from *E. coli* (Sigma), anti-mouse TLR4/ MD-2-biotin and Streptavidin-Phycoerythrin was sourced from eBioscience, and anti-mouse IFN-γ was sourced from BD.

Cells were cultured for the indicated period of time in suspension in the presence or absence of 100 μg/ml Cpn10. Cells were then transferred to 10 ml tubes, counted, pelleted and resuspended in fresh culture medium. 100 μl of cell suspension was transferred to Eppendorf tubes ($10^6$ cells/ tube). 4 hr Cpn10 treatment and LPS stimulation was performed in the Eppendorf tubes kept in the incubator with gentle mixing every 15 mins. Cells were washed 3× with PBS/0.2% FBS. Anti-mouse TLR4-biotin (1 μl in 50 μl PBS/0.2% FBS) or control antibody (anti-mouse IFN-γ-biotin) was incubated with the cells on ice for 1 hr. The cells were washed 3× in 1 ml PBS/0.2% FBS and then blocked with 50 μl PBS/10% FBS for 45 min at 4° C. Streptavidin-PE was then added at 1/100 dilution and incubated for a further 1 hr on ice. After 3 washes the cells were fixed in 1% paraformaldehyde in PBS and analysed on a FACS Caliber using Cell Quest software.

11.2 Results

Figure 21:
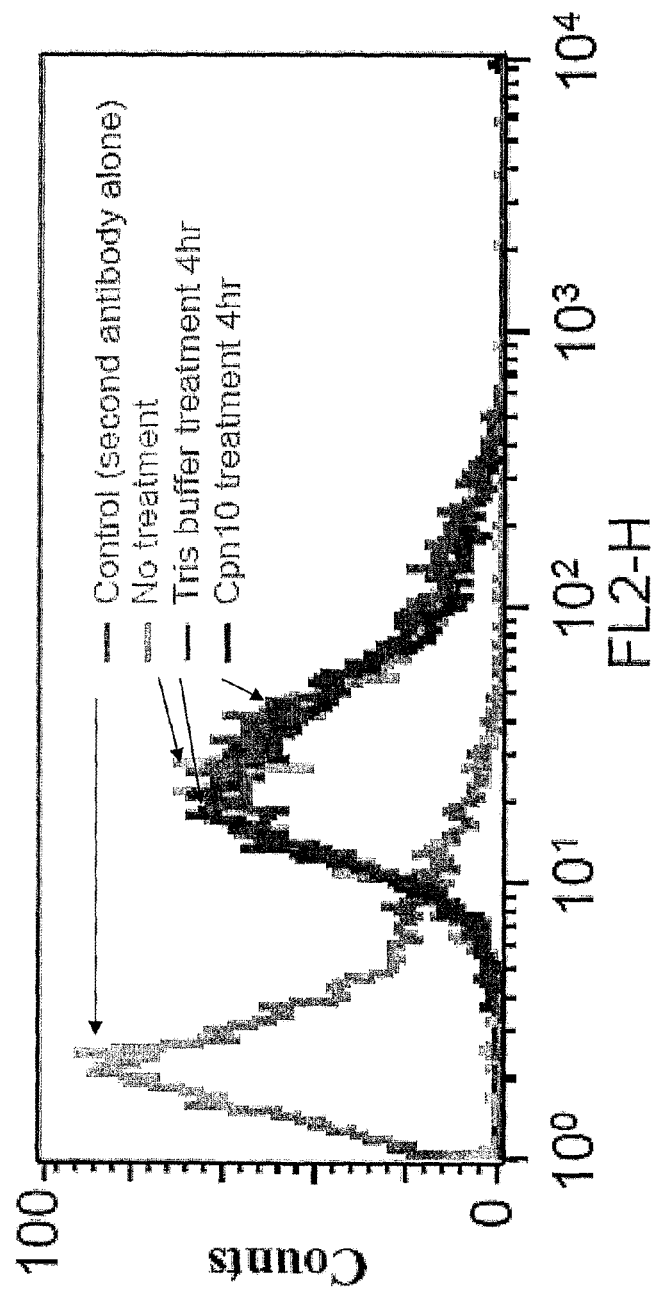

Cpn10 incubated with RAW264 cells for 4 hr does not change TLR4 expression. TLR4 was readily detected on the surface of RAW264 cells using anti-mouse TLR4/MD-2-Biotin followed by Streptavidin-PE (FIG. 21). The control antibody failed to show significant staining (data not shown). Neither Cpn10 treatment for 4 hr or control buffer treatment resulted in an alteration of TLR4 expression.

Down-regulation of TLR4 by LPS and the influence of Cpn10. The addition of 2 ng/ml LPS caused slight reduction (FIG. 22), and 20 ng/ml of LPS caused near complete loss (FIG. 23) of TLR4 expression 2 hr post LPS addition. Cpn10 incubation for 4 hr did not significantly change the behaviour of TLR4 after LPS addition. When Cpn10 treatment was extended to overnight, TLR4 expression was slightly reduced (FIGS. 24 and 25) compared to buffer-treated cells (FIGS. 24 and 25). The LPS-mediated reduction in TLR4 expression was slightly more pronounced in Cpn10-treated cells when the cells were given 2 ng/ml LPS (FIG. 24). When the cells were treated with 20 ng/ml LPS, TLR4 expression was essentially lost in all groups (FIG. 25).

11.3 Discussion and Conclusion

The reduction in LUC activity mediated by 4 hr Cpn10 treatment caused a 30-50% reduction in LPS-induced NF-κB activation. This effect is unlikely to be due to the Cpn10-mediated down-regulation of TLR4 expression as such treatment did little to change TLR4 expression levels. The down-regulation mediated by 2 ng/ml LPS was perhaps very slightly more pronounced after 4 hr Cpn10 treatment, and was certainly more pronounced after overnight Cpn10 treatment. These results suggest that Cpn10 is able to change the dynamics of TLR4 expression following LPS addition.

Example 12

Cpn10 Limits the Cellular Response to a Broad Spectrum of TLR Agonists

The inventors undertook to document the breadth of Cpn10-mediated inhibition of NF-κB activation induced by a number of TLR ligands.

12.1 Materials and Methods

*E. coli* LPS 055:B5 was sourced from Sigma, and *E. coli* LPS 0111:B4 Ultra-Pure ($1×10^6$ EU/mg), *S. aureus* lipoteichoic acid (LTA) (12.5 EU/mg), *S. aureus* peptidoglycan (PGN) (<0.125 EU/mg), *B. subtilis* lipoteichoic acid (LTA) (12.5 EU/mg), *B. subtilis* peptidoglycan (PGN) (0.25 EU/mg), *S. cerevisae* zymosan (<0.125 EU/ml), Imiquimod R837, CpG ODN1826 (mouse), CpG ODN2216 (human), and GpC ODN1826 (non-stimulatory controls), were all sourced from Invivogen. Recombinant mouse IL-1β was sourced from R & D Systems, recombinant mouse IFNγ and recombinant mouse TNFα were sourced from Chemicon. The cytolkine bead array was sourced from BD.

RAW264-HIV-LTR-LUC Bioassay. The bioassay was performed essentially as described in Johnson, B. et al. 2005. *J Biol Chem* 280:4037-4047. In each assay, Cpn10 was tested in a concentration range of 25-100 μg/ml, and the stimulants used at concentrations which elicited a sharp dose-response curve, i.e. *E. coli* LPS at 0.2-5 ng/ml, Ultra-Pure *E. coli* LPS at 5-10 ng/ml, *S. aureus* and *B. subtilis* LTA and PGN at 10-100 μg/ml, *S. cerevisae* zymosan at 10-100 μg/ml. Note that the level of endotoxin contamination in both Cpn10 preparations and in TLR ligands was known to be less than the level shown previously to induce HIV-LTR activation at the concentrations used in these assays using this cell line (Johnson, B. et al. 2005. *J Biol Chem* 280:4037-4047). In data presented below, note that the read-out of stimulation of this cell line is described as activation of NF-κB on the understanding that HIV LTR is known to be highly responsive to NF-κB activation and is therefore an indirect measure of activation of this transcription factor.

Human Peripheral Blood Mononuclear Cell (PBMC) cytokile assays. PBMC were isolated from heparinized blood of healthy volunteers by buoyant density gradient centrifugation on Ficoll-Paque Plus (Amersham Biosciences). PBMC were used as freshly-isolated cells, or alternatively stocks were stored in cryo-tubes in liquid nitrogen until use. PBMC were dispensed at in 200 μl/well at $8×10^5$ viable cells/ml into 96-well tissue culture plates (Greiner Bio-One, Kremsmuenster, Austria). Cpn10 was added for 1 hr, followed by stimulation with agonist for 20 hrs at 37° C. and 5% $CO_2$ prior to collection of culture supernates. Cytokine levels were analysed using commercially available ELISA kits (R&D Sciences) and cytometric bead array (BD).

Detection of phosphorylation levels of signal molecules. RAW264.7 or PBMCs were incubated with Cpn10 for 2 h, followed by LPS stimulation for 30 min, centrifuged and pellets lysed with 0.1% SDS in PBS. Lysates were boiled for 5 min, cooled, cellular debris pelleted by centrifugation, and supernatants assayed for protein concentration as above. Phosphorylated signal proteins were detected using BD CBA Flex Sets for p38, ERK1/2 and JNK1/2. Alternatively, RAW264.7 were treated with Cytofix/Cytoperm (BD) and dual-stained for intracellular p38 and cell surface CD14. Samples were analyzed using the BD FACSArray Bioanalyzer with FCAP array software.

12.2 Results

TLR agonist induced activation of HIV-LTR. The data represented in FIG. 26 demonstrate the ability of Cpn10 to regulate NF-κB activation in murine macrophage RAW264-HIV-LTR-LUC cells which were stimulated with a concentration range of TLR ligands. We have assayed a broad range of ligands to the TLRs, including both UltraPure LPS (TLR4 only) and non-repurified LPS (described as stimulating both TLR2 and TLR4), LTA from two Gram-positive bacteria, *B. subtilis* and *S. aureus*, (TLR2), and PGN from both of the above Gram-positive bacteria (TLR2). In addition, cells were stimulated with zymosan, a preparation isolated from the cell wall of the yeast *S. cerevisiae*, (TLR2/TLR6), and the synthetic double-stranded RNA, poly(I:C), which binds to and stimulates through TLR3. Cells were also tested after stimulation with CpG DNA (TLR9) or imiquimod (R837), a low molecular weight synthetic molecule which activates cells via the TLR7 MyD88-dependent pathway, in the presence of Cpn10. Data is presented showing Cpn10-induced modulation of NF-κB activation following ligation of four of the TLRs tested (TLR2, 4, 7, 9).

FIG. 27 depicts the maximal percent Cpn10-induced inhibition of luciferase activity in RAW264-HIV-LTR-LUC cells stimulated by a variety of TLR ligands. While the response pattern is very similar for most ligands tested, with an average 50% inhibition of HIV-LTR activation, Cpn10 does not appear to change TLR3-induced NF-κB activation in response to poly(I:C). Furthermore, Cpn10 effected a limited NF-κB inhibition of approximately 20% in cells activated by the yeast cell wall preparation zymosan.

The influence of Cpn10 on phosphorylation of intracellular signal proteins. LPS stimulation of RAW264 cells activates several intracellular signaling pathways including the IkappaB kinase (IKK)-NF-κB pathway, and three mitogen-activated protein kinase (MAPK) pathways: extracellular signal-regulated kinases (ERK) 1 and 2, c-Jun N-terminal kinase (JNK) and p38. Further downstream, these signaling pathways activate a number of transcription factors including NF-κB and AP-1 which then coordinate the induction of genes encoding inflammatory mediators. In order to assess the influence of Cpn10 on these signal systems, the inventors measured the levels of phosphorylated p38, JNK1/2 and ERK1/2 in cells stimulated with LPS for 30 minutes, in the absence or presence of Cpn10. The inventors have shown that Cpn10 dose-responsively limits the LPS-induced phosphorylation of each of these members of signaling pathways (FIG. 28).

To confirm the activity of Cpn10 on production of cytokines by freshly-isolated human cells stimulated with a variety of TLR ligands, the inventors pre-treated PBMC from healthy donors with Cpn10 for 1 h and then stimulated with a selected range of TLR ligands for 20 h. Cytokine levels in cell culture supernates were then assayed using ELISA or cytometric bead array. As shown in FIG. 29A-D, cytokine production induced by agonists to TLR2 or TLR4 (PGN, LTA, Zymosan, LPS), including TNF-α, IL-1 β, IL-6 and IL-10, was reduced in the presence of Cpn10. Similarly, stimulation of PBMC with agonists to TLR7 or 9 with Imiquimod or CpG (ODN2216) in the presence of Cpn10 led to a reduced production of cytokines by comparison with control cultures without Cpn10, indicated by data in FIG. 29E.

Pre-incubation of Cpn10 followed by wash does not impact the ability of Cpn10 to limit the LPS-induced activation of NF-κB. The inventors have previously determined that pre-incubation of RAW264-HIV-LTR-LUC cells for 2 hrs with Cpn10 prior to stimulation with LPS optimizes the dose-responsive reduction in luciferase activity. They have also now demonstrated that a 2-hr pre-incubation with Cpn10 followed by a PBS wash prior to LPS stimulation does not alter the Cpn10-mediated reduction in luciferase activity, as a measure of NF-κB activation, as shown in FIG. 30.

Non-TLR agonist induced NF-κB activation. In order to further characterize the activity of Cpn10, the inventors tested Cpn10 modulation of a number of non-TLR agonists. As part of this non-TLR programme, RAW264.7 cells were stimulated with 1-10 ng/ml of low endotoxin (2.24 EU/mg) recombinant mouse IFN-γ for 6 hours in the presence of Cpn10 (FIG. 31). Cell supernatants were collected and analysed for TNF-α using ELISA. Cpn10 was found to potentiate IFN-γ-induced TNF-α production. The marked synergistic increase in the production of TNF-α was enhanced when cells were pre-incubated with Cpn10 for 2 hrs prior to IFN-γ stimulation. Increased NF-κB-induced luciferase levels were also measured in lysates from RAW264-HIV-LTR-LUC cells stimulated with IFN-γ in the presence of Cpn10 for 2 or 4 hours.

12.3 Discussion and Conclusions

The inventors have demonstrated the ability of Cpn10 to regulate the dynamics of the macrophage response to a variety of TLR-specific ligands including TLR2, 4, 7 and 9, and hence the influence of Cpn10 on the phosphorylation of signaling molecules upstream of NF-κB activation and cytokine production, namely members of the MAPK family of signaling proteins, including ERK, JNK and p38. The inventors have also shown that Cpn10 dose-responsively reduces levels of intracellular phosphorylated MAPKs in cells activated by LPS.

The data presented in this example demonstrate that Cpn10 dose-responsively regulates the dynamics of the innate immune response in macrophages stimulated in vitro with a range of TLR ligands. The maximal level of Cpn10-induced inhibition of NF-κB activation triggered by these molecules was approximately 80% following stimulation of the RAW264-HIV-LTR-LUC cell line with a TLR7 agonist (R837). On the other end of the scale, Cpn10 added at concentrations ranging between 10 and 100 μg/ml did not influence the dynamics of TLR2/6 engagement by the yeast cell wall preparation zymosan by more than 20%.

At least one exception to the pattern of reduced NF-κB activation by Cpn10 involves activation by polyinosine-polycytidylic acid (poly(I:C)). Poly(I:C) is a synthetic analogue of double-stranded RNA, a molecular pattern associated with virus infection which activates NF-κB via interaction with TLR3. Rather than limiting the NF-κB activation signal, Cpn10 dose-responsively increases the production of type I interferons in response to this agonist.

Example 13

Identification of Cell Surface Receptors Binding to Cpn10 Conjugated to Solid Matrix 13.1 Materials and Methods Isolation of receptors on host cells that bind Cpn10. Affinity columns (NHS-activated Hi-Trap) columns (AmershamPharmacia) were prepared using Cpn10 (supplied by CBio Ltd, Batch CH003). Cpn10 was dialysed into bicarbonate buffer pH 8.3 and conjugated onto the column according to manufacturer's instructions.

Human monocytes were lysed using NP-40 lysis buffer (0.05% w/v). Whole cell lysates were passed through the Cpn10 affinity columns and unbound molecules were washed away with PBS. Cpn10-binding receptor molecules were eluted using b-octyl-glucoside (b-OG) elution buffer (15 mM triethanolamine, pH 11.5, 140 mM NaCl, and 30 mM b-OG), neutralised with 1M 2-(N-morpholino)ethane-sulfonic acid pH 5, and dialysed against PBS. As a control, cell lysates were also passed over a column onto which no protein had been conjugated.

Eluents were concentrated using Centriprep YM-10 (Millipore), concentrated down to 1 ml and analysed by either SDS-PAGE (FIG. 32) or 2D gel (FIG. 33) electrophoresis. For 2D gel electrophoresis the concentrated eluted solution was buffer-exchanged using rehydration buffer (8 M urea, 2% CHAPS, 10 mM DTT, 0.2% Bio-Lyte) (Biorad) prior to analysis. The bands or spots of interest were excised, tryptic digested and sent for MALDI-TOF analysis.

Separation of proteins by ID gel electrophoresis. The eluted solution was treated with 2×SDS-PAGE reducing buffer (4 ml 10% SDS, 2.5 ml 0.5M Tris—HCl PH:6.8, 5 g of Glycerol, 1 ml of 14.3M mercaptoethanol, and 5 mg of Bromophenol blue) and placed in boiling water for 5 minutes. In order to run the samples Criterion Tris—HCl Precast 4—20% gradient gels (Biorad) were used. The full range RAINBOW molecular weight marker (2 µl) was loaded in the first well and the remaining wells were loaded with 40 µl of sample. The gel was then placed in the electrophoretic bucket and running buffer was added. The running buffer consisted of 0.025 M Tris, 0.2 M Glycine, 0.1% SDS, and was adjusted at pH 8.3. Electrophoresis was carried out for 50 minutes at 200V constant voltage. Following electrophoresis the gels were removed, fixed overnight with fixing buffer (40% ethanol, 10% acetic acid, 50% $H_2O$) and stained with Coomasie blue stain 50% Coomasie blue (0.3 w/v), 25% methanol, 5% acetic acid, 20% $H_2O$) for 1.5 hours. The gels were finally destained by several washes with destain (10% ethanol, 10% acetic acid, 80% $H_2O$, Separation of proteins by 2D gel electrophoresis. A non-linear immobilized pH gradient (3-10 ReadyStrip IPG strip 11 cm) was used as the first dimension. Aliquots of 200 µl of sample were pipetted into the focusing tray and the IPG strip was placed over them with gel side down through the solution that contained sample and buffer. Mineral oil was placed over the IPG strip to avoid precipitation of the urea. The strips were allowed to rehydrate for 12 hours under passive conditions at 20° C. The strips were then focused for approximately 52,000 v-hr at 6000-7000 volts at a constant 50 µA per strip. To prepare the ReadyStrip IPG strips for the second dimension, they were removed from the focusing tray and equilibrated in 5 ml of buffer containing 50 mM Tris HCl, pH 8.8, 6 M urea, 2% SDS, 30% glycerol, 1% DTT. A second equilibration followed in 5 ml volume of the same buffer with 1.5% iodoacetamide substituted for the DTT. After equilibration, the ReadyStrip IPG strips were placed onto the Criterion gels (4-20% gradient) and overlayed with 0.5% agarose with a trace of mercaptoethanol. The gels were run in the Criterion cell for 60 min at 200 V. Following electrophoresis the gels were removed, fixed overnight with fixing buffer (40% ethanol, 10% acetic acid, 50% $H_2O$) and stained with Coomasie blue stain (50% Coomasie blue (0.3 w/v), 25% methanol, 5% acetic acid, 20% $H_2O$) for 1.5 hours. The gels were finally destained by several washes with destain (10% ethanol, 10% acetic acid, 80% $H_2O$).

13.2 Results

Isolation of Cpn10-binding proteins by affinity chromatography and SDSPAGE electrophoresis. The inventors performed preliminary studies using the methodology as described and identified several Cpn10-binding proteins using mass spectrometry analysis, as shown in Table 5.

TABLE 5

Identification of Cpn10-binding molecules using mass spectrometry

| Protein Name | Accession No |
|---|---|
| 78 kDa glucose-regulated protein precursor (GRP 78) | GRP78_MESAU |
| Serum albumin precursor | ALBU_BOVIN |
| Elongation factor Tu-B | EFTU2_PSEPK |
| Annexin A2 | ANXA2_HUMAN |
| Triosephosphate isomerase | TPIS_PANTR |
| Profilin-1 | PROF1_HUMAN |
| 10 kDa heat shock protein mitochondrial | CH10_HUMAN |
| Ig gamma-1-chain C region | IGHG1_HUMAN |
| Ig alpha 2 chain C region | IGHA2_HUMAN |
| alpha-1-antitrypsin precursor | A1AT_HUMAN |
| Peptidyl-propyl-cis-trans-isomerase A (Cyclosporin A-binding protein) | PPIA_MACMU |

In order to verify these results as well as determine the identities of the proteins that were not identified, the inventors repeated the isolation of Cpn10-binding protein by affinity chromatography and analysed the eluted molecules by SDS-PAGE (FIG. 32) as well as by 2-dimensional gel electrophoresis (FIG. 33).

Control experiments in which cell lysates were run over an affinity column to which no protein had been conjugated demonstrated no protein bands on SDSPAGE (data not shown).

13.3 Discussion and Conclusions

This mass spectrometry data has enabled the identification of several proteins, which could be potentially important for the binding and intracellular trafficking of Cpn10 to host cells. In particular, profilin, a small actin-binding protein, which regulates the dynamics of actin polymerization, appears to be a Cpn10-binding protein. Another molecule which could be important in regulating Cpn10 responses is GRP78. GRP78 is a chaperone that could be involved in the trafficking of Cpn10.

Example 14

The Influence of Cpn10 on the Ross River Virus Antiviral Response by Cells Stimulated with PolyI:C In Vitro The inventors were interested to test whether Cpn10 influences polyI:C-induced anti-viral resistance using a virus known to be highly sensitive to the antiviral effects of IFNα/β.

14.1 Materials and methods

Cpn10. Cpn10 was dissolved in Tris-saline buffer pH7.6 and frozen on dry ice in aliquots and stored at −20° C. Aliquots were thawed prior to use.

PolyI:C. For the data shown in FIG. 34, PolyI:C (supplied by Invivogen) was dissolved in sterile saline at 5 mg/ml stored frozen at −20° C. Vials were thawed and diluted into medium. For buffer controls, the same volume and sterile saline was added to cell culture wells. For the data shown in FIG. 35, PolyI:C was dissolved in sterile saline at 5 mg/ml, then aliquotted at 25 μl/500 μl and 62.5 μl of 100% ethanol (2.5 volumes) added to precipitate the dsRNA. The tubes were stored at −70° C. On the day of the assay, aliquots were centrifuged at top speed (13,000 rpm) for 30 min at 40° C. The pellet was washed once in 70% ethanol DEPC-treated distilled water, pelleted, the supernate removed and the pellet dried in the hood (about 15 mins) and resuspended in 100 μl RPMI 1640. The recovery of dsRNA was determined to be about 50% as determined using the RNA quantitation feature of the BioPhotometer (Eppendorf). All the dsRNA concentrations given in the figures assume a 50% recovery.

Antiviral assay. RAW264.7 cells were grown as adherent cultures in flasks and scraped (i.e. not trypisinised) prior to seeding into 96-well plates. HeLa cells were trypsinised in the standard way prior to seeding. Cells were seeded in duplicate in a 96-well plate ($5 \times 10^3$ for RAW264.7 cells and $10^4$ for HeLa cells in 50 μl medium per well). After 4 h, Cpn10 was added (in 50 μl diluted in medium) and after a further 30 mins polyI:C was added (in 50 μl diluted in medium). The cells were then incubated overnight in the 96-well plates and then RRV was added (MOI=1 for RAW264.7 cells, and MOI=10 for HeLa cells in 50 μl). After 3 days, the cells were fixed, stained with crystal violet, washed, dried and dye extracted with 100% methanol and read at A595 nm as described (Antalis et al, J Exp Med 1998, 187(11):1799).

14.2 Results

The effect of polyI:C on RAW264.7 cells. Initially polyI:C was titrated into RAW264.7 cells in the range of 0-100 μg/ml). Concentrations of polyI:C>5-10 μg/ml resulted in cells showing clear signs of toxicity with cells rounding up and growing poorly over the three day assay period. No such toxicity was observed for HeLa cells (FIG. 34).

Cpn10 and polyI:C. Titrations were established to determine the dose required for induction of anti-viral resistance for RAW264.7 cells and HeLa cells. Then, using an appropriate concentration range of polyI:C, the hypothesis was tested as to whether Cpn10 increased the antiviral activity of dsRNA. As shown in FIG. 35, neither RAW264.7 cells nor HeLa cells showed any difference in their antiviral resistance in the presence or absence of Cpn10 at the concentrations of polyI:C and Cpn10 tested over this three day assay measuring cell viability.

14.3 Discussion and Conclusions

In this study, Cpn10 did not influence synthetic dsRNA-induced antiviral resistance against alphavirus-induced CPE. The data presented here does not support the view that Cpn10 may influence signaling by dsRNA. dsRNA can signal via TLR3, PKR, RIG-1/mda-5 and/or ATF-2/c-Jun, although TLR3 is believed to be the major sensor of extracellular dsRNA, with the other signaling pathways triggered by cytoplasmic dsRNA.

Example 15

Recombinant Cpn10 Interacts at the Cell Surface with APC

Figure 36A:
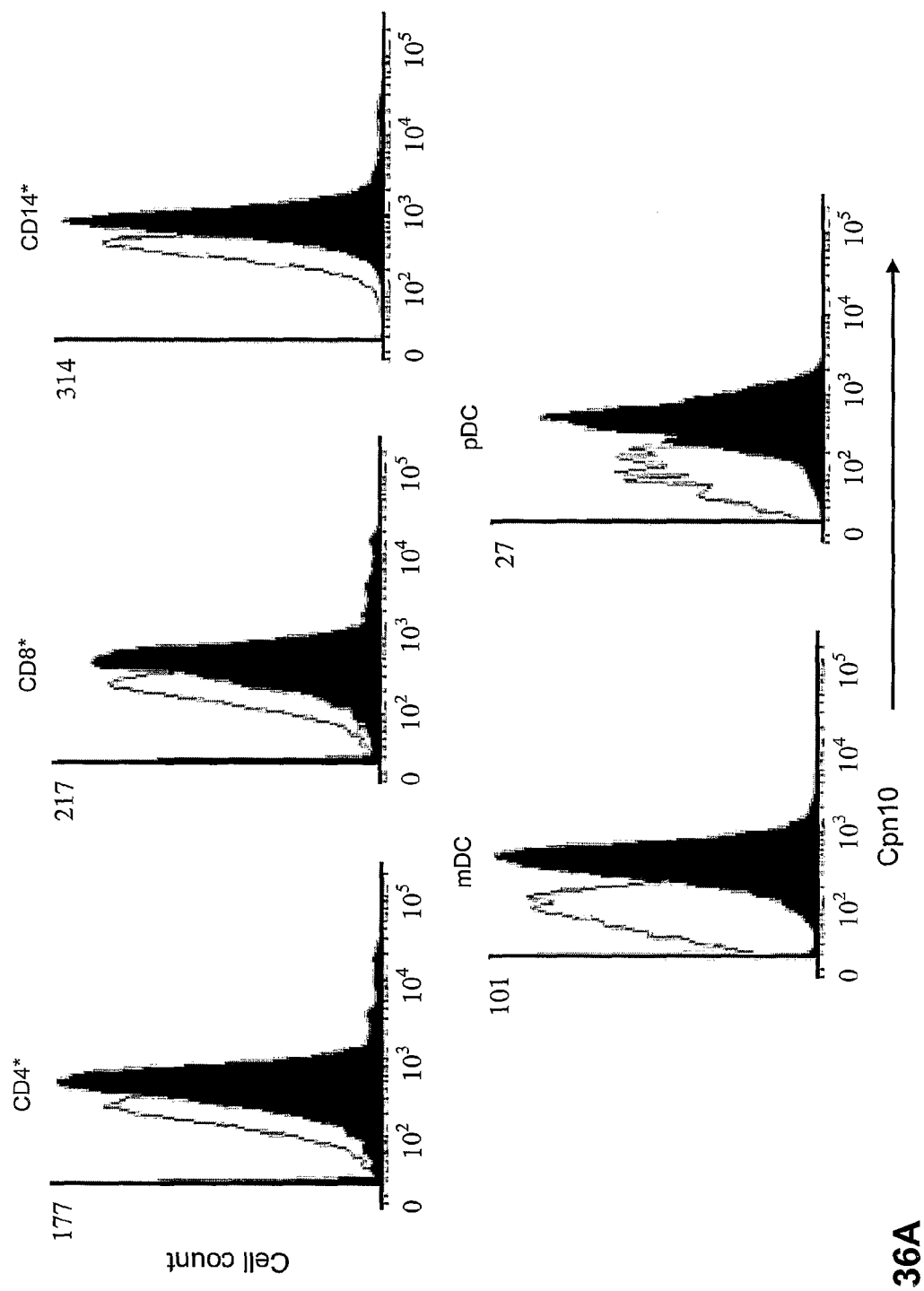
Figure 36B:
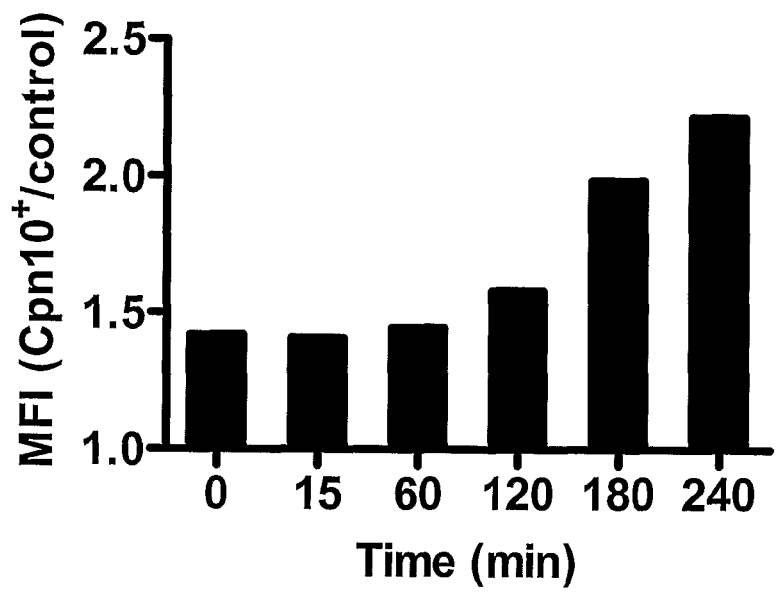

The inventors considered the means by which extracellular Cpn10 might modulate an immune response. To identify which leukocyte subpopulations of cells bind Cpn10, the inventors fluorophore-tagged Cpn10 at a C-terminal cysteine residue and demonstrated that it retained equivalent chaperone and immunomodulatory activity to wild type Cpn10 in vitro (data not shown). Upon incubation of labeled Cpn10 with PBMC at 4° C., together with a panel of antibodies to identify separate leukocyte subpopulations, it was demonstrated that Cpn10 interacts most strongly with APCs, specifically myeloid DC ($CD3^-CD4^{low}CD14^-CD11c^+$), plasmacytoid DC ($CD3^-CD4^{low}CD14^-CD11c^{low}$) and monocytes ($CD4^{low}CD14^+$), with lower affinity to T cells (FIG. 36A). When PBMC were stimulated with LTA, there was an approximate 1.6-fold increase in the level of fluorescent Cpn10 binding to the surface of $CD14^+$ cells by 4 h, by comparison with unstimulated $CD14^+$ cells (FIG. 36B). These data suggest that extracellular Cpn10 exerts its biological activity on APCs, key regulatory cells of the innate immune system.

Figure 36C:
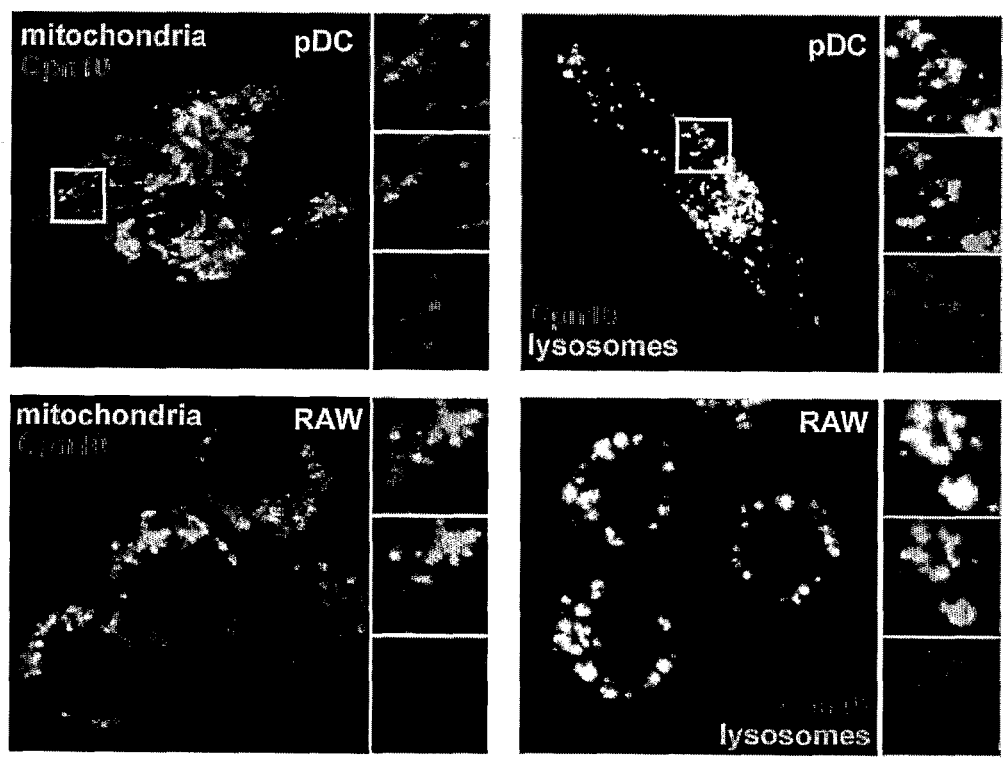

The inventors also followed the uptake pathway of fluorescent Cpn10 into immune cells by confocal microscopy. When human pDC or mouse macrophages were incubated with fluorescent Cpn10, together with reagents to identify intracellular compartments, it was demonstrated that Cpn10 was rapidly taken up and trafficked to the acidified intracellular vesicles without entering the cytosol or mitochondria (FIG. 36C). These data show that Cpn10 protein associates with immune competent cells and is concentrated in areas that signal the presence of TLR activating motifs.

Example 16

Compositions for Treatment

In accordance with the best mode of performing the invention provided herein, specific preferred compositions are outlined below. The following are to be construed as merely illustrative examples of compositions and not as a limitation of the scope of the present invention in any way.

Example 16(a)

Composition for Parenteral Administration

A composition for intramuscular injection could be prepared to contain 1 ml sterile buffered water, and 1 mg of a suitable compound.

Similarly, a composition for intravenous infusion may comprise 250 ml of sterile Ringer's solution, and 5 mg of a suitable compound.

Example 16(b)

Injectable Parenteral Composition

A composition suitable for administration by injection may be prepared by mixing 1% by weight of a suitable compound in 10% by volume propylene glycol and water. The solution is sterilised by filtration.

Example 16(c)

Capsule Composition

A composition of a suitable compound in the form of a capsule may be prepared by filling a standard two-piece hard gelatin capsule with 50 mg of the agent or compound, in powdered form, 100 mg of lactose, 35 mg of talc and 10 mg of magnesium stearate.

Example 16(d)

Eye Drop Composition

A typical composition for delivery as an eye drop is outlined below:

| Suitable compound | 0.3 g |
|---|---|
| Methyl Hydroxybenzoate | 0.005 g |
| Propyl Hydroxybenzoate | 0.06 g |
| Purified Water about to | 100.00 ml. |

The methyl and propyl hydroxybenzoates are dissolved in 70 ml purified water at 75° C., and the resulting solution is allowed to cool. The suitable compound is then added, and the solution sterilised by filtration through a membrane filter (0.22 μm pore size), and aseptically packed into sterile containers.

Example 16(e)

Composition for Inhalation Administration

For an aerosol container with a capacity of 20-30 ml: a mixture of 10 mg of a suitable compound with 0.5-0.8% by weight of a lubricating agent, such as polysorbate 85 or oleic acid, is dispersed in a propellant, such as freon, and put into an appropriate aerosol container for either intranasal or oral inhalation administration.

Example 16(f)

Ointment Composition

A typical composition for delivery as an ointment includes 1.0 g of a suitable compound, together with white soft paraffin to 100.0 g, dispersed to produce a smooth, homogeneous product.

The invention claimed is:

1. A method for modulating Toll-like receptor signaling in a subject, or in at least one cell, tissue or organ thereof, wherein said method consists of administering to the subject an effective amount of human chaperonin 10 selected from the group consisting of SEQ ID NO: 1, SEQ ID NO: 2, and SEQ ID NO:3, wherein Toll-like receptor signaling involves association of the chaperonin 10 with a Toll-like receptor and a Toll-like receptor agonist in an activation cluster, and wherein the Toll-like receptor signaling involves at least one Toll-like receptor agonist present in the subject, or in at least one cell, tissue, or organ thereof, wherein the activation cluster comprises chaperonin 10, TLR2 and lipoteichoic acid (LTA).

2. A method for modulating Toll-like receptor signaling in a subject, or in at least one cell, tissue or organ thereof, wherein said method consists of administering to the subject an effective amount of human chaperonin 10 selected from the group consisting of SEQ ID NO: 1, SEQ ID NO: 2, and SEQ ID NO:3, wherein Toll-like receptor signaling involves association of the chaperonin 10 with a Toll-like receptor and a Toll-like receptor agonist in an activation cluster, and wherein the Toll-like receptor signaling involves at least one Toll-like receptor agonist present in the subject, or in at least one cell, tissue, or organ thereof, wherein the activation cluster comprises chaperonin 10, TLR3 and double-stranded RNA.

3. A method for modulating Toll-like receptor signaling in a subject, or in at least one cell, tissue or organ thereof, wherein said method consists of administering to the subject an effective amount of chaperonin 10 selected from the group consisting of SEQ ID NO: 1, SEQ ID NO: 2, and SEQ ID NO:3, wherein Toll-like receptor signaling involves association of the chaperonin 10 with a Toll-like receptor and a Toll-like receptor agonist in an activation cluster, wherein the activation cluster comprises chaperonin 10, TLR7 and single-stranded RNA.

4. A method for modulating Toll-like receptor signaling in a subject, or in at least one cell, tissue or organ thereof, wherein said method consists of administering to the subject an effective amount of human chaperonin 10 selected from the group consisting of SEQ ID NO: 1, SEQ ID NO: 2, and SEQ ID NO:3, wherein Toll-like receptor signaling involves association of the chaperonin 10 with a Toll-like receptor and a Toll-like receptor agonist in an activation cluster, and wherein the Toll-like receptor signaling involves at least one Toll-like receptor agonist present in the subject, or in at least one cell, tissue, or organ thereof, wherein the activation cluster comprises chaperonin 10, TLR9 and DNA comprising a CpG motif.

* * * * *

SEQUENCE LISTING

```
<160> NUMBER OF SEQ ID NOS: 10

<210> SEQ ID NO 1
<211> LENGTH: 101
<212> TYPE: PRT
<213> ORGANISM: Homo sapiens

<400> SEQUENCE: 1

Ala Gly Gln Ala Phe Arg Lys Phe Leu Pro Leu Phe Asp Arg Val Leu
 1               5                  10                  15

Val Glu Arg Ser Ala Ala Glu Thr Val Thr Lys Gly Gly Ile Met Leu
            20                  25                  30

Pro Glu Lys Ser Gln Gly Lys Val Leu Gln Ala Thr Val Val Ala Val
        35                  40                  45

Gly Ser Gly Ser Lys Gly Lys Gly Gly Glu Ile Gln Pro Val Ser Val
    50                  55                  60

Lys Val Gly Asp Lys Val Leu Leu Pro Glu Tyr Gly Gly Thr Lys Val
65                  70                  75                  80

Val Leu Asp Asp Lys Asp Tyr Phe Leu Phe Arg Asp Gly Asp Ile Leu
                85                  90                  95

Gly Lys Tyr Val Asp
            100

<210> SEQ ID NO 2
<211> LENGTH: 104
<212> TYPE: PRT
<213> ORGANISM: Homo sapiens

<400> SEQUENCE: 2

Gly Ser Met Ala Gly Gln Ala Phe Arg Lys Phe Leu Pro Leu Phe Asp
 1               5                  10                  15

Arg Val Leu Val Glu Arg Ser Ala Ala Glu Thr Val Thr Lys Gly Gly
            20                  25                  30

Ile Met Leu Pro Glu Lys Ser Gln Gly Lys Val Leu Gln Ala Thr Val
        35                  40                  45

Val Ala Val Gly Ser Gly Ser Lys Gly Lys Gly Gly Glu Ile Gln Pro
    50                  55                  60
```

Val Ser Val Lys Val Gly Asp Lys Val Leu Leu Pro Glu Tyr Gly Gly
 65                  70                  75                  80

Thr Lys Val Val Leu Asp Asp Lys Asp Tyr Phe Leu Phe Arg Asp Gly
                 85                  90                  95

Asp Ile Leu Gly Lys Tyr Val Asp
            100

<210> SEQ ID NO 3
<211> LENGTH: 102
<212> TYPE: PRT
<213> ORGANISM: Homo sapiens

<400> SEQUENCE: 3

Ala Ala Gly Gln Ala Phe Arg Lys Phe Leu Pro Leu Phe Asp Arg Val
  1               5                  10                  15

Leu Val Glu Arg Ser Ala Ala Glu Thr Val Thr Lys Gly Gly Ile Met
             20                  25                  30

Leu Pro Glu Lys Ser Gln Gly Lys Val Leu Gln Ala Thr Val Val Ala
         35                  40                  45

Val Gly Ser Gly Ser Lys Gly Lys Gly Gly Glu Ile Gln Pro Val Ser
 50                  55                  60

Val Lys Val Gly Asp Lys Val Leu Leu Pro Glu Tyr Gly Gly Thr Lys
 65                  70                  75                  80

Val Val Leu Asp Asp Lys Asp Tyr Phe Leu Phe Arg Asp Gly Asp Ile
                 85                  90                  95

Leu Gly Lys Tyr Val Asp
            100

<210> SEQ ID NO 4
<211> LENGTH: 309
<212> TYPE: DNA
<213> ORGANISM: Homo sapiens

<400> SEQUENCE: 4
atggcaggac aagcgtttag aaagtttctt ccactctttg accgagtatt ggttgaaagg     60
agtgctgctg aaactgtaac caaaggaggc attatgcttc cagaaaaatc tcaaggaaaa    120
gtattgcaag caacagtagt cgctgttgga tcgggttcta aaggaaaggg tggagagatt    180
caaccagtta gcgtgaaagt tggagataaa gttcttctcc cagaatatgg aggcaccaaa    240
gtagttctag atgacaagga ttatttccta tttagagatg gtgacattct tggaaagtac    300
gtagactga                                                           309

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cggctaccac atccaaggaa                                                20

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6

-continued

```
gctggaatta ccgcggct                                              18

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
gccgaaactg taaccaaagg                                            20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
caggctcaat ctctccactc                                            20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
cctggttgtt cactccctga                                            20

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
caacagcatc acaagggttt t                                          21
```